(12) United States Patent
Blumenfeld et al.

(10) Patent No.: US 9,452,991 B2
(45) Date of Patent: Sep. 27, 2016

(54) PIPERIDINE DERIVATIVES AS HUMAN PAPILLOMA VIRUS INHIBITORS

(75) Inventors: Marta Blumenfeld, Paris (FR); Delphine Compere, Sceaux (FR); Jean-Michel Gauthier, Conflans-Sainte-Honorine (FR)

(73) Assignee: AVIRAGEN THERAPEUTICS, INC., Alpharetta, GA (US)

( * ) Notice: Subject to any disclaimer, the term of this patent is extended or adjusted under 35 U.S.C. 154(b) by 805 days.

(21) Appl. No.: 13/466,530

(22) Filed: May 8, 2012

(65) Prior Publication Data

US 2012/0220633 A1    Aug. 30, 2012

Related U.S. Application Data

(62) Division of application No. 12/300,998, filed as application No. PCT/EP2007/054843 on May 18, 2007, now Pat. No. 8,207,373.

(30) Foreign Application Priority Data

May 19, 2006  (FR) ...................................... 06 04496

(51) Int. Cl.
*A61K 31/4453*   (2006.01)
*C07D 295/145*   (2006.01)
*C07D 295/135*   (2006.01)

(52) U.S. Cl.
CPC ................. *C07D 295/135* (2013.01)

(58) Field of Classification Search
CPC .................. A61K 31/4453; C07D 295/145
See application file for complete search history.

(56) References Cited

U.S. PATENT DOCUMENTS 4,292,429 A    9/1981   Marxer

FOREIGN PATENT DOCUMENTS

| WO | WO 00/56331 | 9/2000 |
| WO | WO 2004/108673 A2 | 12/2004 |
| WO | WO 2004108673 A2 * | 12/2004 |

OTHER PUBLICATIONS

Kumar et al.; "Intralesional injection of Mycobacterium w vaccine vs imiquimod, 5%, cream in patients with anogenital warts: a randomized clinical trial"; JAMA Dermatol. Oct. 2014; 150(10): 1072-8; PubMed abstract; PMID: 25103148.*
Merito et al.; "Treatment patterns and associated costs for genital warts in Italy"; Current Medical Research and Opinion; 2008; 24(11): 3175-3783.*
Berge et al.; Pharmaceutical Salts; 1977; Journal of Pharmaceutical Sciences; 66(1): 1-19; IDS reference.*
Patani et al.; "Bioisosterism: A Rational Approach in Drug Design"; 1996; Chem. Rev.; 96: 3147-3176.*
Poirier et al., "Reduction of N-Nitrosodiphenylamine to unsym-Diphenylhydrazine by Lithium Aluminium Hydride," *J. Am. Chem. Soc.*, 1954, 74(12), p. 3192.
White et al., "Inhibition of Human Papilomavirus DNA Replication by Small Molecule Antagonists of the E1-E2 Protein Interaction," *J. Biol. Chem.*, 2003, 278(29), pp. 26765-26772.
Grell et al., "Repaglinide and Related Hypoglycemic Benzoic Acid Derivatives," *J. Med. Chem.*, 1998, 41(26), pp. 5219-5246.
Rinderknecht et al., "Oxindolylalanine," *J. Org. Chem.*, 1953, 18(8), pp. 971-982.
Poirier et al., "The Chemistry of Hydrazyl Free Radicals. III. Further Evidence of the Contribution of α-Groups Toward the Stabilization of α, α-Disubstituted-β-Picrylhydrazyl Free Radicals," *J. Org. Chem.*, 1954, 19(7), pp. 1157-1162.
Kisseljova et al., "Addition of Arylboronic Acids to Symmetrical and Unsymmetrical Azo Compounds," *Org. Lett.* 2006, 8(1), pp. 43-45.
Chiang et al., "Vrial E1 and E2 proteins support replication of homologous and heterologous papillomaviral origins," *Proc. Natl. Acad. Sci. USA*, 1992, 89, pp. 5799-5803.
Bellamy, "Selective Reduction of Aromatic Nitro Compounds with Stannous Chloride in Non Acidic and Non Aqueous Medium," *Tetrahedron Lett.*, 1984, 25(8), pp. 839-842.
Scheibye et al., "Studies on Organophosphorus Compounds XXI. The Dimer of p-Methoxyphenylthionophosphine Sulfide as Thiation Reagent," *Bull. Soc. Chim. Beig.*, 1978, 87(3), pp. 229-238.
Berge et al., "Pharmaceutical Salts," *J. Pharm. Sci.*, 1977, 66(1), pp. 1-19.
Roche, "Bioreversible Carriers in Drug Design: Theory and Application", Pergamon Press: New York, 1987, pp. 14-21.
Stella, "Pro-drugs: An Overview and Definition", *A.C.S. Symposium Series, American Society*, 1975, vol. 14, pp. 1-115.
STN: Accession No. 1981:103366; 1981.
Notice of Allowance issued in U.S. Appl. No. 12/300,998 on Feb. 10, 2012.
Office Action issued in U.S. Appl. No. 12/300,998 on Aug. 26, 2011.
Office Action issued in U.S. Appl. No. 12/300,998 on Jun. 9, 2011.
Ashby et al., "Definitive relationships among chemical structure, carcinogenicity and mutagenicity for 301 chemicals tested by U.S. NTP," Mutation Research, vol. 257, pp. 229-306, 1991.

(Continued)

*Primary Examiner* — Timothy Thomas
(74) *Attorney, Agent, or Firm* — B. Aaron Schulman, Esq.; Stites & Harbison, PLLC.

(57) ABSTRACT

HPV inhibitors with formula (I) where $G_1$ represents a hydrocarbonated bond or chain possibly substituted by one or two alkyl groups, $G_2$ represents a group (see formula Ia+Ib) or R represents a hydrogen, an alkyl, halogenoalkyl, or a prodrug radical such as carbamate, acetyl or dialkylaminomethy, G represents a bond or a hydrocarbonated chain possibly substituted by one or two alkyls, W represents an oxygen or sulphur, $R_1$ and $R_2$ each represent a group chosen from among hydrogen, halogen, hydroxyl, thio, alkoxy, halogenoalkoxy, alkylthis, halogenoalkylthio, amino, monoalkylamino, dialkylamino, cycloalkyl, alkyl or halogenoalkyl, R3 represents an acid or a prodrug radical of the acid function or a bioisotere of the acid function, A represents an aryl, cycloalkyl, cycloalkenyl or a heterocycle with 6 chains, each possibly substituted, and pharmaceutically acceptable salts.

13 Claims, No Drawings

(56) References Cited

OTHER PUBLICATIONS

Cheeseman et al., "A Tiered Approach to Threshold of Regulation," Food and Chemical Toxicology, vol. 37, pp. 387-412, 1999.

European Medicines Agency, "ICH guideline S2 (R1) on genotoxicity testing and data interpretation for pharmaceuticals intended for human use," Mar. 2008, www.ema.europa.eu/docs/en_GB/document_library/Scientific_guideline/2011/12/WC500119604.pdf (accessed Apr. 27, 2015).

AutoNom (Automatic Nomenclature)—Source: Isisdraw—Anaconda Pharma (Nov. 3, 2008), 1 pg.

STN Karlsruhe—American Chemical Society (2011), 13 pgs.

* cited by examiner

PIPERIDINE DERIVATIVES AS HUMAN PAPILLOMA VIRUS INHIBITORS

This application is a divisional of U.S. patent application Ser. No. 12/300,998, filed Nov. 14, 2008, which is a U.S. national stage of PCT/EP2007/054843, filed May 18, 2007, which claims priority to French patent application no. 0604496, filed May 19, 2006, all of which are hereby incorporated by reference in their entirety.

The present invention relates to novel antiviral compounds directed against the papilloma virus, to pharmaceutical compositions containing them, to their preparation method and synthesis intermediates as well as to their use for treating or preventing an infection by the papilloma virus.

The papilloma viruses are non-encased viruses, the genome of which is formed by double strand DNA of about 8 kb. They are very widespread in nature and cause epithelial lesions in human as well as in many animals including rabbits, horses, dogs, and bovine species. More than a hundred human papilloma viruses (HPV) have been described. They are classified depending on their infection sites. About 30 HVP have been isolated from anogenital mucosas (cervix uteri, vagina, valva, penis, anus, rectum). The other HPVs are associated with skin lesions. The HPVs with cutaneous tropism include i.a., HPV1, HPV2, HPV3, HPV4, HPV5, HPV7, HPV8, HPV9, HPV10, HPV12, HPV14, HPV15, HPV17, HPV19, HPV20, HPV21, HPV22, HPV23, HPV24, HPV25, HPV26, HPV27, HPV28, HPV29, HPV38, HPV41, HPV47, HPV49. They are associated with lesions such as warts (verruca vulgaris, verruca plantaris, myrmecia wart, surface wart, verruca plana . . .) and diseases such as epidermo-dysplasia verruciformis.

The mucogenital type HPVs are involved in laryngeal and anogenital diseases including certain cancers. They are often classified as high risk HPVs and low risk HPVs, with reference to the type of lesions with which they are associated. The low risk HPVs include, i.a., HPV6, HPV11, HPV13, HPV32, HPV34, HPV40, HPV42, HPV43, HPV44, HPV53, HPV54, HPV55, HPV57, HPV58, HPV74, HPV91.

The low risk HPVs are associated with benign lesions such as condylomas (genital warts such as acuminated condylomas and plane condylomas), laryngeal, conjunctive or buccal papillomas or other epithelial lesions such as intra-epithelial neoplasias of low grade or recurrent respiratory papillomatoses, and more rarely bowenoid papuloses or high grade intra-epithelial neoplasias or carcinomas. High risk HPVs include i.a., HPV16, HPV18, HPV31, HPV33, HPV35, HPV39, HPV45, HPV51, HPV52, HPV56, HPV59, HPV61, HPV62, HPV66, HPV67, HPV68, HPV72. They are involved in low grade intra-epithelial lesions which may develop into higher grade lesions right up to cancers, in particular cervix uteri cancer and other anogenital cancers.

Genital infections by HPVs are the most frequent sexually transmitted infections in the world, including in the developed countries with more than 20 million people infected in the United States. Prevalence of HPV infections varies from 3-42% depending on the countries and affects 10-20% of the sexually active population in industrialized countries. In part of this population, the infection persists and may lead to cancers in the case of high risk HPVs.

The prevalence of genital warts (condylomas) is estimated to be 1-2% in the sexually active population of industrialized countries, i.e. about 3,500,000 new cases every year in these countries and 28,000,000 worldwide. Genital warts may be found on parts of the body comprising the anus, vulva, vagina, cervix uteri and penis or peripheral bodies thereto.

Treatments of genital warts are based on several strategies, from physical destruction (cryotherapy, $CO_2$ laser, electro-surgery, surgical excision), application of cytotoxic agents (TCA, podophyllin, podofilox) right up to the application of immuno-modulator agents (interferon, imiquimod). However, none of these methods completely eliminates all the viral particles, and significant rates of recurrence, accompanied by severe secondary effects are observed with present therapeutic strategies. This reinforces a need for new strategies for controlling or eliminating infections by papilloma viruses.

Unlike what exists in the treatment of other viral diseases, such as those caused by HIV, herpes viruses or influenza viruses, to this day there is no antiviral treatment which specifically targets viral pathogens which the papilloma viruses are.

The papilloma viruses infect multistratified epitheliums and their viral cycle is closely related to organogenesis of theses organs and to differentiation of keratinocytes. After infection, the viral genome is present and replicated in a small number in basal cells of the epithelium. As the cells gradually differentiate, the expression of the viral genes and the number of copies of the viral genome increase until expression of the genes of the viral capsid and formation of infectious virions in totally differentiated keratinocytes.

The genome of HPVs potentially codes for about ten proteins. The earliest expressed proteins, E1 and E2, are involved in the replication of the viral genome and the regulation of the expression of the viral genes. The other early proteins of these viruses (E4, E5, E6, E7) have functions in relationship with cell proliferation or roles which are not yet completely explained. The existence of E3 and E8 proteins is still uncertain. Late proteins L1 and L2 are those which form the viral capsid.

The only 2 viral proteins required and sufficient for replicating HPVs are E1 and E2. They are capable of forming an E1/E2 complex and of binding on the replication origin (Ori) of the HPVs, a sequence contained in the viral genome and bearing close sites recognized by E1 and by E2. E2 is capable of binding with very high affinity to the E2 sites whereas E1, alone, does not have very high affinity for E1 sites. The interaction between E1 and E2 increases binding of E1 on Ori by cooperative binding to DNA. Once it is bound to DNA, E1 no longer interacts with E2 but forms a hexamer. The helicase and ATPase activities of E1 allow unfolding of the viral DNA which is then replicated by the cell replication mechanism.

The inventors have sought to develop small molecules which inhibit replication of HPVs, preferably with a low risk, by notably interfering with the formation of the complex between the E1 and E2 proteins.

A solution was found by elaborating novel derivatives.

The object of the present invention is these novel derivatives, their synthesis, as well as their use in pharmaceutical compositions capable of being used in preventing and treating pathologies related to inhibition of HPV replication, such as for example, HPV1, HPV2, HPV3, HPV4, HPV5, HPV7, HPV8, HPV9, HPV10, HPV12, HPV14, HPV15, HPV17, HPV19, HPV20, HPV21, HPV22, HPV23, HPV24, HPV25, HPV26, HPV27, HPV28, HPV29, HPV38, HPV41, HPV47, HPV49, HPV6, HPV11, HPV13, HPV32, HPV34, HPV40, HPV42, HPV43, HPV44, HPV53, HPV54, HPV55, HPV57, HPV58, HPV74, HPV91, HPV16, HPV18, HPV31, HPV33, HPV35, HPV39, HPV45, HPV51, HPV52, HPV56, HPV59, HPV61, HPV62, HPV66, HPV67, HPV68, HPV72 preferably low risk HPVs such as HPV6, HPV11, HPV13, HPV32, HPV34, HPV40, HPV42, HPV43, HPV44, HPV53, HPV54, HPV55, HPV57, HPV58, HPV74, HPV91.

The novel derivatives, objects of the present invention, are active against the papilloma virus. They are also capable of inhibiting E1/E2 interaction.

Within the scope of the present invention, the following definitions are provided:

"Alkyl" or "Alk" means a monovalent or divalent, linear or branched, saturated hydrocarbon chain, comprising 1-6 carbon atoms such as the methyl, ethyl, propyl, isopropyl, tertbutyl, methylene, ethylene, propylene group . . .

"Acyl" means a —COR group wherein R is an alkyl group as defined earlier or a phenyl group, for example an acetyl, ethylcarbonyl, benzoyl group . . .

"Acylamino" means a —NHC(O)R group wherein R is an alkyl group as defined earlier.

"Acylaminoalkyl" means a -AlkNHC(O)R group wherein Alk and R are alkyl groups as defined earlier.

"Alkoxy" means a —OAlk group wherein Alk is an alkyl group as defined earlier. Alkoxy comprises for example methoxy, ethoxy, n-propyloxy, tert-butyloxy, . . .

"Aryl" means an aromatic monocyclic or bicyclic system comprising 4-10 carbon atoms, it being understood that in the case of a bicyclic system, one of the rings has an aromatic character and the other ring is aromatic or unsaturated. Aryl comprises for example phenyl, naphthyl, indenyl, benzocyclobutenyl groups, . . .

"Heterocycle" means a saturated, unsaturated or aromatic, fused, spiro-fused or bridged monocyclic or bicyclic system with 3-12 members, comprising 1-4 heteroatoms, either identical or different, selected from oxygen, sulfur and nitrogen, and possibly containing 1 or 2 oxo or thioxo groups, it being understood that in the case of a bicyclic system, one of the rings may have an aromatic character and the other ring is aromatic or unsaturated. Heterocycle comprises for example the piperidyl, piperazyl, furyl, thienyl, pyrrolyl, pyrazolyl, imidazolyl, pyridyl, pyrimidyl, pyrazinyl, pyradizinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, [1,2,3]triazolyl, [1,2,4]triazolyl groups, . . .

"Alkylthio" means a —SAlk group wherein Alk is an alkyl group as defined earlier. Alkylthio comprises for example methylthio, ethylthio, isopropylthio, heptylthio, . . .

"Arylalkyl" means a -Alk-Ar group wherein Alk represents an alkyl group as defined earlier and Ar represents an aryl group as defined earlier.

"Halogen atom" means a fluorine, bromine, chlorine or iodine atom.

"Cycloalkyl" means a saturated, fused or bridged monocyclic or bicyclic system comprising 3-12 carbon atoms such as the cyclopropyl, cyclobutyl, cyclopentyl, cyclohexyl, cycloheptyl, cyclooctyl, adamantyl, decalinyl, norbornyl group, . . .

"Cycloalkenyl" means an unsaturated fused or bridged monocyclic or bicyclic system comprising 3-12 carbon atoms such as the cyclopropenyl, cyclobutenyl, cyclopentenyl, cyclohexenyl group, . . .

"Monoalkylamino" means a —NHAlk group wherein Alk is an alkyl group as defined earlier.

"Dialkylamino" means a —NAlkAlk' group wherein Alk and Alk' each represent independently of each other an alkyl group as defined earlier.

"Monoalkylamide" means a —C(O)NHAlk group wherein Alk is an alkyl group as defined earlier.

"Dialkylamide" means a —C(O)NAlkAlk' group wherein Alk and Alk' each represent independently of each other an alkyl group as defined earlier.

"N-cycloalkyl" means a cycloalkyl radical as defined earlier comprising a nitrogen atom, bound to the remainder of the molecule through this atom. N-cycloalkyl for example comprises the piperid-1-yl or pyrrolid-1-yl group.

"N-cycloalkenyl" means a cycloalkenyl radical as defined earlier, comprising a nitrogen atom, bound to the remainder of the molecule through this atom. N-cycloalkenyl for example comprises the tetrahydropyridin-1-yl group.

"Haloalkyl" means a linear or branched saturated hydrocarbon chain comprising 1-6 carbon atoms and substituted with 1-6 halogen atoms such as the trifluoromethyl, 2,2,2-trifluoroethyl group, . . .

"Haloalkoxy" means a branched or linear saturated hydrocarbon chain comprising 1-6 carbon atoms and substituted with 1-6 halogen atoms, said chain being bound to the compound through an oxygen atom, such as the trifluoromethoxy, 2,2,2-trifluoroethoxy group, . . .

"Haloalkylthio" means a linear or branched saturated hydrocarbon chain comprising 1-6 carbon atoms and substituted with 1-6 halogen atoms, said chain being attached through a sulfur atom, such as the trifluoromethylthio group, . . .

"Protective Group" or "protection group" means the group which selectively blocks the reactive site in a multifunctional compound so that a chemical reaction may be selectively carried out at another non-protected reactive site, in the sense conventionally associated with the latter in synthesis chemistry.

"Isomerism" means compounds which have identical molecular formulae but which differ by nature or in the binding sequence of their atoms or in the arrangement of their atoms in space. Isomers which differ in the arrangement of their atoms in space are designated by "stereoisomers". Stereoisomers which are not mirror images of each other are designated by "diastereoisomers" and stereoisomers which are non-superposable images in a mirror are designated by "enantiomers" or optical isomers. "Stereoisomers" refer to racemates, enantiomers and diastereoisomers.

"Pharmaceutically acceptable" means that which is generally secure, non-toxic, and which is not biologically undesirable, both for veterinary use and for human pharmaceutical use.

"Pharmaceutical acceptable salts" of a compound means salts which are pharmaceutically acceptable as defined herein and which have the desired pharmacological activity of the parent compound. It should be understood that all references to pharmaceutically acceptable salts comprise the solvent addition forms (solvates) or crystalline forms (polymorphous forms) such as defined herein, of the same acid or base addition salts. A review of pharmaceutically acceptable salts is notably described in *J. Pharm. Sci.*, 1977, 66, 1-19.

"Pharmaceutically acceptable acids" mean non-toxic acid salts derived from organic or mineral acids. Among pharmaceutically acceptable acids, mention may be made in a non-limiting way, of hydrochloric, hydrobromic, sulfuric, phosphonic, nitric, acetic, trifluoroacetic, lactic, pyruvic, malonic, succinic, glutaric, fumaric, tartaric, maleic, citric, ascorbic, oxalic, methane-sulfonic, camphoric, benzoic, toluenesulfonic acids, . . .

"Pharmaceutically acceptable bases" mean non-toxic basic salts derived from organic or mineral bases, formed when an acidic proton present in the parent compound is replaced by a metal ion or is coordinated to an organic base.

Among pharmaceutically acceptable bases, mention may be made in a non-limiting way to sodium hydroxide, potassium hydroxide, lithium hydroxide, calcium hydroxide, triethylamine, tertbutylamine, diethylaminoethanol, ethanolamine, ethylenediamine, dibenzylethylenediamine, piperidine, pyrrolidine, morpholine, piperazine, benzylamine, arginine, lysine, histidine, glucosamine, quaternary ammonium hydroxides, . . .

By "prodrug" is meant a chemical derivative of the compound, object of the present invention, which generates in vivo said compound by a spontaneous chemical reaction with the physiological medium, notably by an enzymatic reaction, a photolysis and/or a metabolic reaction.

By "prodrug radical of the acid function" is meant a labile functional group which will generate in vivo an acid function upon being separated from the compound, object of the present invention, by a spontaneous chemical reaction with the physiological medium, notably by enzymatic reaction, photolysis and/or metabolic reaction. The prodrug radicals with an acid function notably comprise ester, pivoyloxymethyl, acetoxymethyl, phthalidyl, indanyl, methoxymethyl or 5-R-2-oxo-1,3-dioxolen-4-ylmethyl groups. Other examples are described in T. Higuchi and V. Stella, "Prodrugs as Novel Delivery Systems", Vol. 14, A.C.S. Symposium Series, American Chemical Society (1975) and "Bioreversible Carriers in Drug Design: Theory and Application", edited by E. B. Roche, Pergamon Press: New York, 14-21 (1987).

In the present patent application, chemical compounds are named according to the IUPAC (The International Union of Pure and Applied Chemistry) nomenclature.

The object of the present invention is compounds of formula (I):

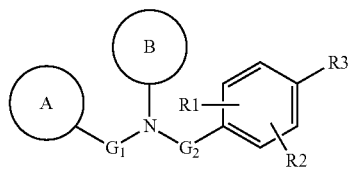

(I)

as well as their stereoisomers,
wherein:
$G_1$ represents a bond or a saturated or unsaturated, branched or linear hydrocarbon chain comprising 1-4 carbon atoms, optionally substituted with one or two alkyl groups, preferably identical,
$G_2$ represents a

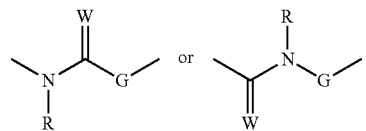

group wherein:
R represents hydrogen atom, an alkyl, haloalkyl group, or a prodrug radical such as a carbamate, acetyl, dialkylaminomethyl or —$CH_2$—O—CO-Alk,
G represents a bond or a saturated or unsaturated, linear or branched hydrocarbon chain comprising 1-4 carbon atoms, optionally substituted with one or two alkyl groups, preferably identical, W represents an oxygen, sulfur atom or NH,
$R_1$ and $R_2$ either identical or different, each represent a group selected from a hydrogen atom, a halogen atom, a hydroxyl, thio, alkoxy, haloalkoxy, alkylthio, haloalkylthio, amino, monoalkylamino, dialkylamino, cycloalkyl, alkyl or haloalkyl group,
$R_3$ represents an acid group or a prodrug radical of the acid function such as an ester, or else a bioisoster of the acid function such as a tetrazole, phosphonate, phosphonamide, sulfonate or sulfonamide,
A represents an aryl, cycloalkyl, cycloalkenyl group or a heterocycle, each optionally substituted, and
B represents an aryl group or a 6-membered heterocycle, each optionally substituted,
as well as their pharmaceutically acceptable salts,
A as defined earlier may be substituted with one or two groups, either identical or different, selected from:
a hydrogen atom, a halogen atom,
an alkoxy, alkylthio, haloalkoxy, haloalkylthio, hydroxyl, thio, cyano, amino, monoalkylamino, or dialkylamino group,
an —$SO_nR'$, —COR', —$CO_2R'$, —OCOR', —CONR'R", —NR'COR" or —$NR'SO_2R"$ group, wherein R' and R" each represent independently of each other a hydrogen atom, an alkyl, haloalkyl group, and n has the value 1 or 2,
an alkyl or haloalkyl group, the alkyl group being optionally substituted with a cyano, amino, monoalkylamino, dialkylamino or acylamino group,
an aryl, arylalkyl, —X-aryl, —X-arylalkyl or -Alk-X-aryl group wherein X represents —O—, —NH—, —N(Alk)-, —N(COCH$_3$)—, —S—, —SO—, —$SO_2$—, —CO— or —CONH—, each substituted on the aryl portion with one or two substituents, either identical or different, selected from:
a hydrogen atom or a halogen atom,
an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide group,
an —$SO_nR'$, —COR', —$CO_2R'$, —OCOR', —CONR'R", —NR' COR" or —$NR'SO_2R"$ group, wherein R' and R" each represent independently of each other a hydrogen atom, an alkyl, haloalkyl group and n has the value 1 or 2,
a heterocycle, -Alk-heterocycle, —X-heterocycle, —X-Alk-heterocycle, or -Alk-X-heterocycle group, wherein X represents —O—, —NH—, —N(Alk)-, —N(COCH$_3$)—, —S—, —SO—, —$SO_2$—, —CO—, or —CONH—, each optionally substituted on the heterocycle portion with one or two substituents either identical or different, selected from:
a hydrogen atom or a halogen atom,
an alkyl, haloalkyl, alkoxy, haloalkoxy, thio, alkylthio, haloalkylthio, hydroxyl, cyano, acyl, amino, monoalkyl- or dialkylamino, acid, ester, amide, mono- or di-alkylamide, or
a —$SO_nR'$, —COR', —$CO_2R'$, —OCOR', —CONR'R", —NR'COR" or $NR'SO_2R"$ group, wherein R' and R" each represent independently of each other a hydrogen atom, an alkyl, haloalkyl group and n has the value 1 or 2,
a cycloalkyl, -Alk-cycloalkyl, cycloalkenyl, -Alk-cycloalkenyl, —X-cycloalkyl, —X-Alk-cycloalkyl, —X-cycloalkenyl, —X-Alk-cycloalkenyl, -Alk-X-cycloalkyl, -Alk-X-cycloalkenyl group, wherein X represents —O—, —NH—, —N(Alk)-, —N(COCH₃)—, —S—, —SO—, —SO₂—, —CO— or —CONH—, each optionally substituted on the cyclic portion with one or two substituents, either identical or different, selected from:

a hydrogen atom or a halogen atom, an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide, or oxo or, —SO$_n$R', —COR', —CO₂R', —OCOR', —CONR'R", —NR'COR" or NR'SO₂R" group, wherein R' and R" each represent independently of each other a hydrogen atom, an alkyl, haloalkyl group and n has the value 1 or 2, B as defined earlier may be an aryl or 6-membered heterocycle, substituted in the ortho position with a R₄ group and optionally substituted with a R₅ group, wherein:

R₄ represents:

an alkyl, —NHAlk, —NAlkAlk', —NHcycloalkyl or —NAlkcycloalkyl group, Alk and Alk' being identical or different, a cycloalkyl, cycloalkenyl, N-cycloalkyl or N-cycloalkenyl group, each optionally substituted with one or two substituents, either identical or different, selected from a hydrogen atom, a halogen atom, an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or dialkylamide, oxo or —X-aryl group and wherein X represents —O—, —NH—, —N(Alk)-, —N(COCH₃)—, —S—, —SO—, —SO₂—, —CO— or —CONH—, or an aryl group optionally substituted with one or two substituents, either identical or different, a hydrogen atom, a halogen atom, an alkyl, haloalkyl, alkoxy, haloalkoxy, thio, alkylthio, haloalkylthio, hydroxyl, cyano, acyl, amino, monoalkylamino or dialkylamino, acid, ester, amide, mono or dialkylamide or —X-aryl group, wherein X represents —O—, —NH—, —N(Alk)-, —N(COCH₃)—, —S—, —SO—, —SO₂—, —CO— or —CONH—, R₅ represents:

a hydrogen atom or a halogen atom, a hydroxyl, alkoxy, haloalkoxy, thio, alkylthio, haloalkylthio, amino, monoalkylamino, dialkylamino, —NHacyl, cyano, acyl, acid, ester, amide, monoalkylamide or dialkylamide group, an alkyl or haloalkyl group, the alkyl group may be substituted with a cyano, hydroxyl, alkoxy, acid or ester group, a —SO$_n$Alk, —SO$_n$NH₂, —SO$_n$NHAlk or —SO$_n$NAlkAlk' group, wherein n has the value of 1 or 2 and Alk and Alk' are either identical or different, or a piperidine, oxopiperidine, morpholine group or else a piperazine group optionally substituted with an alkyl or acyl group, The preferred compounds are the compounds of formula (I) wherein:

G₁ represents a bond or a saturated or unsaturated, linear or branched hydrocarbon chain comprising 1-4 carbon atoms, optionally substituted with one or two alkyl groups, preferably identical, G₂ represents a

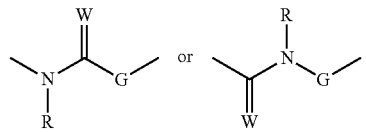

group wherein:

R represents a hydrogen atom, an alkyl, haloalkyl group, or a prodrug radical such as carbamate, acetyl, dialkylaminomethyl or —CH₂—O—CO-Alk, G represents a bond or a hydrocarbon chain comprising 1-4 carbon atoms, linear or branched, saturated or unsaturated, optionally substituted with one or two alkyl groups, preferably identical, and W represents an oxygen, sulfur atom or NH, R₁ and R₂ either identical or different, each represent a group selected from a hydrogen atom, a halogen atom, a hydroxyl, thio, alkoxy, haloalkoxy, alkylthio, haloalkylthio, amino, monoalkylamino, dialkylamino, cycloalkyl, alkyl or haloalkyl group, R₃ represents an acid group or a prodrug radical of the acid function such as ester, or else a bioisoster of the acid function such as tetrazole, phosphonate, phosphonamide, sulfonate or sulfonamide, A represents an aryl or heterocycle group, each being optionally substituted with one or two groups, either identical or different, selected from:

a hydrogen atom, a halogen atom, an alkoxy, alkylthio, haloalkoxy, haloalkylthio, hydroxyl, thio, cyano, amino, monoalkylamino or dialkylamino group, a —SO$_n$R', —COR'—, —CO₂R', —OCOR', —CONR'R", —NR'COR" or —NR'SO₂R" group, wherein R' and R" each represent independently of each other a hydrogen atom, an alkyl, haloalkyl group, and n has the value 1 or 2, an alkyl or haloalkyl group, the alkyl group being optionally substituted with a cyano, amino, monoalkylamino, dialkylamino or acylamino group, an aryl, arylalkyl, —X-aryl group, wherein X represents —O—, —NH—, —N(Alk)-, —N(COCH₃)—, —S—, —SO—, —SO₂—, —CO— or —CONH— group, each substituted on the aryl portion with one or two substituents, either identical or different, selected from:

a hydrogen atom or a halogen atom, an alkyl, haloalkyl, alkoxy, haloalkoxy, thio, alkylthio, haloalkylthio, hydroxyl, cyano, acyl, amino, monoalkylamino or di-alkylamino, acid, ester, amide, mono- or dialkylamide group, or a —SO$_n$R', —COR', —CO₂R', —OCOR', —CONR'R", —NR'COR" or —NR'SO₂R" groups, wherein R' and R" each represent independently of each other a hydrogen atom, an alkyl, haloalkyl group, and n has the value 1 or 2, a heterocycle, —X-heterocycle group wherein X represents —O—, —NH—, —N(alk)-, —N(COCH₃)—, —S—, —SO—, —SO₂—, —CO— or —CONH—, each optionally substituted on the heterocycle portion with one or two substituents, either identical or different, selected from:

a hydrogen atom or a halogen atom, an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide, or an —SO$_n$R', —COR', —CO$_2$R', —OCOR', —CONR'R", —NR' COR" or —NR'SO$_2$R" group, wherein R' and R" each represent independently of each other a hydrogen atom, an alkyl, haloalkyl group, and n has the value 1 or 2, or a cycloalkyl, cycloalkenyl, —X-cycloalkyl, —X-cycloalkenyl group where X represents —O—, —NH—, —N(Alk)-, —N(COCH$_3$)—, —S—, —SO—, —SO$_2$—, —CO— or —CONH— group, each optionally substituted on the cyclic portion with one or two substituents either identical or different selected from:
a hydrogen atom or a halogen atom,
an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide, or oxo, or
an —SO$_n$R', —COR', —CO$_2$R', —OCOR', —CONR'R", —NR'COR" or —NR'SO$_2$R" group, wherein R' and R" each represent independently of each other a hydrogen atom, an alkyl, haloalkyl group, and n has the value 1 or 2, and B represents a phenyl or pyridine group:
substituted in the ortho position with an N-cycloalkyl group such as piperidine or with a cyclohexyl, each optionally substituted with one or two substituents either identical or different, selected from a hydrogen atom, an alkyl, haloalkyl, alkoxy, haloalkoxy, —X-aryl group, where X represents —O—, —NH—, —N(Alk)-, —N(COCH$_3$)—, —S—, —SO—, —SO$_2$—, —CO— or CONH—, and/or
optionally substituted with a halogen atom or with an alkyl or haloalkyl group.

The compounds which are still more preferred are the compounds of formula (I) wherein:

G$_1$ represents a bond or a saturated or unsaturated, linear or branched, hydrocarbon chain comprising 1-4 carbon atoms, optionally substituted with one or two alkyl groups, preferably identical, G$_2$ represents

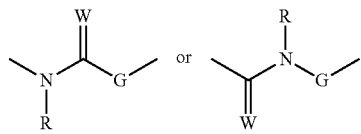

group wherein:
R represents a hydrogen atom, an alkyl, haloalkyl group or a prodrug radical such as a carbamate, acetyl, dialkylaminomethyl, or —CH$_2$—O—CO-Alk,
G represents a bond or a saturated or unsaturated, linear or branched hydrocarbon chain comprising 1-4 carbon atoms, optionally substituted with one or two alkyl groups, preferably identical, and
W represents an oxygen, sulphur atom or NH—, R$_1$ and R$_2$ either identical or different, each represent a group selected from a hydrogen atom, a halogen atom, a hydroxyl, thio, alkoxy, haloalkoxy, alkylthio, haloalkylthio, amino, monoalkylamino, dialkylamino, cycloalkyl, alkyl or haloalkyl group, R$_3$ represents an acid group or a prodrug radical of the acid function such as an ester, or else a bioisoster of the acid function such as a tetrazole, phosphonate, phosphonamide, sulfonate or sulfonamide, A represents an aryl group optionally substituted with one or two groups, either identical or different, selected from:
a hydrogen atom, a halogen atom,
an alkoxy, alkylthio, haloalkoxy, haloalkylthio, hydroxyl, thio, cyano, amino, monoalkylamino or dialkylamino group,
an —SO$_n$R', —COR', —CO$_2$R', —OCOR', —CONR'R", —NR'COR" or —NR'SO$_2$R" group, wherein R' and R" each represent independently of each other a hydrogen atom, an alkyl, haloalkyl group, and n has the value 1 or 2,
an alkyl or haloalkyl group, the alkyl group being optionally substituted with a cyano, amino, monoalkylamino, dialkylamino, or acylamino group,
an aryl, arylalkyl, —X-aryl group, wherein X represents —O—, —NH—, —N(Alk)-, —N(COCH$_3$)—, —S—, —SO—, —SO$_2$—, —CO— or —CONH—, each substituted on the aryl portion with one or two substituents, either identical or different, selected from:
a hydrogen atom or a halogen atom,
an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide group, or
an —SO$_n$R', —COR', —CO$_2$R', —OCOR', —CONR'R", —NR'COR" or —NR'SO$_2$R" group, wherein R' and R" each represent independently of each other a hydrogen atom, an alkyl, haloalkyl group, and n has the value 1 or 2,
a heterocycle, —X-heterocycle group, wherein X represents —O—, —NH—, —N(Alk)-, —N(COCH$_3$)—, —S—, —SO—, —SO$_2$—, —CO— or —CONH—, each optionally substituted on the heterocycle portion with one or two substituents, either identical or different, selected from:
a hydrogen atom or a halogen atom,
an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide, or
an —SO$_n$R', —COR', —CO$_2$R', —OCOR', —CONR'R", —NR'COR" or —NR'SO$_2$R" group, wherein R' and R" each represent independently of each other a hydrogen atom, an alkyl, haloalkyl group, and n has the value 1 or 2, or
a cycloalkyl or —X-cycloalkyl group, wherein X represents —O—, —NH—, —N(Alk)-, —N(COCH$_3$)—, —S—, —SO—, —SO$_2$—, —CO— or —CONH—, each optionally substituted on the cyclic portion with one or two substituents, either identical or different, selected from a hydrogen atom, a halogen atom, an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide or oxo group, and B represents a phenyl or pyridine group:
substituted in the ortho position with a N-cycloalkyl group such as piperidine or with a cyclohexyl, each optionally substituted with one or two substituents, either identical or different, selected from a hydrogen atom, an alkyl, haloalkyl, alkoxy, haloalkoxy, —X-aryl, wherein X represents —O—, —NH—, —N(Alk)-, —N(COCH$_3$)—, —S—, —SO—, —SO$_2$—, —CO— or —CONH— group, and/or
optionally substituted with a halogen atom or with an alkyl, or haloalkyl group.

The more preferred compounds are the compounds of formula (I) wherein:

$G_1$ represents a bond or a saturated or unsaturated, linear or branched hydrocarbon chain comprising 1-4 carbon atoms, optionally substituted with one or two alkyl groups, preferably identical, preferably a bond or a hydrocarbon chain comprising one or two carbon atoms, $G_2$ represents a

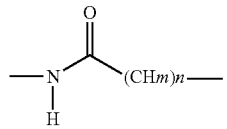

group wherein n is an integer comprised between 1 and 4 and m is an integer having the value 1 or 2, preferably n has the value 1 or 2, $R_1$ represents an alkoxy group, such as methoxy, preferably in the ortho position relatively to $R_3$, $R_2$ represents a hydrogen or halogen atom, such as chlorine or bromine, or an alkyl group, such as methyl, preferably in the meta position relatively to $R_3$, $R_3$ represents an acid or ester group, A represents an aryl group such as a phenyl, preferably substituted:
  in the meta or para position with:
    a halogen atom or an alkyl, haloalkyl, cyano, alkoxy, haloalkoxy, acylaminoalkyl group or an —XR group, wherein X represents —O—, —NH—, —N(Alk)-, —N(COCH$_3$)—, —S—, —SO—, —SO$_2$—, —CO— or —CONH— group, and R represents an arylalkyl, cycloalkyl or aryl group, each optionally substituted with one or two substituents, either identical or different, such as a halogen atom, an alkoxy, alkyl, haloalkyl, cyano, acyl, amino, monoalkylamino or dialkylamino, acid, ester, amide, mono- or di-alkylamide group, or an —SO$_n$R', —OCOR', —NR'—COR" or —NR'SO$_2$R" group, wherein R' and R" each represent independently of each other a hydrogen atom, an alkyl, haloalkyl group, and n has the value 1 or 2, or
    a cycloalkyl, aryl, arylalkyl group or heterocycle, preferably N-cycloalkyl, each optionally substituted with one or two substituents, either identical or different, such as a halogen atom, an alkoxy, alkyl, haloalkyl, cyano, acyl, amino, monoalkylamino or dialkylamino, acid, ester, amide, mono- or di-alkylamide group, or an —SO$_n$R', —OCOR', —NR'COR", or —NR'SO$_2$R''' group, wherein R' and R" each represent independently of each other a hydrogen atom, an alkyl, haloalkyl group and n has the value 1 or 2,
  and/or in the ortho or meta position with an alkyl group, and B represents an aryl group, preferably a phenyl,
  substituted in the ortho position with a heterocycle, preferably a N-cyloalkyl, such as piperidine group, and/or
  substituted in the ortho' position with an alkyl group, such as a methyl.

The more preferred compounds are the compounds of formula (I) wherein:

$G_1$ represents a bond or a saturated on unsaturated, linear or branched hydrocarbon chain comprising 1-4 carbon atoms, optionally substituted with one or two alkyl groups, preferably identical, preferably a bond or a hydrocarbon chain comprising 1 or 2 carbon atoms, $G_2$ represents a

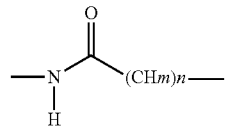

group,
wherein n is an integer comprised between 1 and 4 and m is an integer having the value 1 or 2, preferably n has the value 1 or 2, $R_1$ represents an alkoxy group, such as methoxy, preferably in the ortho position relatively to $R_3$, $R_2$ represents a hydrogen or halogen atom such as chlorine or bromine, or an alkyl group, such as methyl, preferably in the meta position relatively to $R_3$, $R_3$ represents an acid or ester group, A represents an aryl group, such as phenyl, preferably substituted:
  in the meta or para position with:
    a halogen atom or a cyano, alkoxy, haloalkoxy, acylaminoalkyl or —XR group, wherein X represents —O—, —S—, —SO—, —SO$_2$—, or —CO— and R represents an arylalkyl, cycloalkyl or aryl group, each optionally substituted with one or two substituents, either identical or different, such as a halogen atom, an alkoxy or acyl group, or
    a cycloalkyl, aryl or arlyalkyl group, each optionally substituted with one or two substituents, either identical or different, such as an acyl or alkoxy group, and
  and/or in the ortho or meta position with an alkyl group, and B represents an aryl group, preferably a phenyl,
  substituted in the ortho position with a heterocycle, preferably a N-cycloalkyl, such as a piperidine group, and/or
  substituted in the ortho' position with an alkyl group, such as a methyl.

The more preferred compounds are the compounds of formula (I) wherein:

$G_1$ represents a bond or a saturated or unsaturated, linear or branched hydrocarbon chain comprising 1-4 carbon atoms, optionally substituted with one or two alkyl groups, preferably identical, preferably a bond or a hydrocarbon chain comprising 1 or 2 carbon atoms, $G_2$ represents a

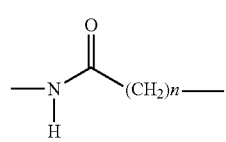

group,
wherein n is an integer comprised between 1 and 4, preferably n has the value 1, $R_1$ represents an alkoxy group, such as methoxy, preferably in the ortho position relatively to $R_3$, $R_2$ represents a hydrogen or halogen atom, such as chlorine or bromine, or an alkyl group, such as methyl, preferably in the meta position relatively to $R_3$, $R_3$ represents an acid or ester group, A represents an aryl group, such as a phenyl, preferably substituted in the meta or para position with:
- a halogen atom or a alkoxy, haloalkoxy, or —XR group, wherein X represents —O— and R represents an arylalkyl, cycloalkyl or aryl group, each optionally substituted with one or two substituents, either identical or different, such as a halogen atom, an alkoxy or acyl group, or
- a cycloalkyl, aryl or arylalkyl group, each optionally substituted with one or two substituents, either identical or different, such as an acyl group, and B represents an aryl group, preferably a phenyl,
- substituted in the ortho position with a heterocycle, preferably a N-cycloalkyl, such as a piperidine group, and/or
- substituted in the ortho' position with an alkyl group, such as a methyl.

Still more preferred compounds are grouped in Table I:

TABLE I

| | |
|---|---|
| 1 | 5-brom-2-methoxy-4-[N-(4-methoxy-phenyl)-N-(2(piperidin-1-yl-phenyl)-hydrazinocarbonyl-methyl]-benzoic acid hydrochloride |
| 2 | 5-bromo-2-methoxy-4-[N-(2-piperidin-1-yl-phenyl)-N-(4-trifluoromethoxy-phenyl)-hydrazinocarbonyl-methyl]-benzoic acid hydrochloride |
| 3 | 5-bromo-2-methoxy-4-[N-(3-methoxy-benzyl)-N-(2-piperidin1-yl-phenyl)-hydrazinocarbonylmethyl]-benzoic acid hydrochloride |
| 4 | 4-[N-(4-benzyloxy-phenyl)-N-(2-piperidin-1-yl-phenyl)hydrazinocarbonylmethyl]-5-bromo-2-methoxy-benzoic acid hydrochloride |
| 5 | 5-bromo-4-{N-[4-(4-fluoro-phenoxy)-phenyl]-N-(2-piperidin-1-yl-phenyl)-hydrazinocarbonylmethyl}-2-methoxy-benzoic acid hydrochloride |
| 6 | 5-bromo-2-methoxy-4-{N-[2-(4-methoxy-phenyl)-ethyl]-N-2-piperidin-1-yl)-phenyl]-hydrazino-carbonylmethyl}-benzoic acid hydrochloride |
| 7 | 5-bromo-2-methoxy-4-[N-(4-methoxy-phenyl)-N-(2-methyl-6-piperidin-1-yl-phenyl)-hydrazino-carbonylmethyl]-benzoic acid hydrochloride |
| 7a | Methyl 5-bromo-2-methoxy-4-[N-(4-methoxy-phenyl)-N-(2-methyl-6-piperidin-1-yl-phenyl)-hydrazino-carbonylmethyl]-benzoate |
| 8 | 5-bromo-2-methoxy-4-[N-(4-methoxy-benzyl)-N-(2-piperidin-1-yl-phenyl)-hydrazinocarbonylmethyl]-benzoic acid hydrochloride |
| 9 | 5-bromo-4-[N-(4-cyclohexyl-phenyl)-N-(2-piperidin-1-yl-phenyl)-hydrazinocarbonylmethyl]-2-methoxy-benzoic acid hydrochloride |
| 10 | 5-bromo-2-methoxy-4-[N-(2-methyl-6-piperidin-1-yl-phenyl)-N-(4-trifluoromethoxy-phenyl)-hydrazino-carbonylmethyl]-benzoic acid hydrochloride |
| 11 | 5-bromo-2-methoxy-4-[N-(4'-methoxy-biphenyl-4-yl)-N-(2-piperidin-1-yl-phenyl)-hydrazinocarbonyl-methyl]-benzoic acid hydrochloride |
| 12 | 5-bromo-4-[N-(4-cyclohexyloxy-phenyl)-N-(2-piperidin-1-yl-phenyl)-hydrazinocarbonylmethyl]-2-methoxy-benzoic acid hydrochloride |
| 13 | 5-bromo-2-methoxy-4-[N-(4-phenoxy-phenyl)-N-(2-piperidin-1-yl-phenyl)-hydrazinocarbonylmethyl]-benzoic acid hydrochloride |
| 14 | 5-bromo-4-{N-[4-(4-chloro-phenoxy)-phenyl]-N-(2-piperidin-1-yl-phenyl)-hydrazinocarbonylmethyl}-2-methoxy-benzoic acid hydrochloride |
| 15 | 4-{N-[4-(4-fluoro-phenoxy)-phenyl]-N-(2-methyl-6-piperidin-1-yl-phenyl)-hydrazinocarbonylmethyl}-2-methoxy-benzoic acid hydrochloride |
| 16 | 5-bromo-4-{N-[4-(4-fluoro-phenoxy)-phenyl]-N-(2-methyl-6-piperidin-1-yl-phenyl)-hydrazino-carbonylmethyl}-2-methoxy-benzoic acid hydrochloride |
| 16a | Methyl 5-Bromo-4-{N-[4-(4-fluoro-phenoxy)-phenyl]-N-(2-methyl-6-piperidin-1-yl-phenyl)-hydrazino-carbonyl-methyl}-2-methoxy-benzoate |
| 17 | 4-[N-(4-benzyl-phenyl)-N-(2-piperidin-1-yl-phenyl)hydrazinocarbonylmethyl]-5-bromo-2-methoxy-benzoic acid hydrochloride |
| 18 | 4-[N-(4-bromo-phenyl)-N-(2-piperidin-1-yl-phenyl)hydrazinocarbonylmethyl]-5-chloro-2-methoxy-benzoic acid hydrochloride |
| 19 | 4-[N-(3'-acetyl-biphenyl-4-yl)-N-(2-piperidin-1-yl-phenyl)-hydrazinocarbonylmethyl]-5-chloro-2-methoxy-benzoic acid hydrochloride |
| 20 | 4-[N-(4'-acetyl-biphenyl-4-yl)-N-(2-piperidin-1-yl-phenyl)-hydrazinocarbonylmethyl]-5-chloro-2-methoxy-benzoic acid hydrochloride |
| 21 | 5-bromo-2-methoxy-4-[N-(3-phenoxy)-phenyl]-N-(2 piperidin-1-yl-phenyl)-hydrazinocarbonylmethyl]-benzoic acid hydrochloride |
| 22 | 5-bromo-2-methoxy-4-[N-(4-phenylsulfanyl)-phenyl]-N-(2piperidin-1-yl-phenyl)-hydrazinocarbonylmethyl]-benzoic acid hydrochloride |
| 23 | 4-[N-(4-benzenesulfonyl-phenyl)-N-(2-piperidin-1-yl-phenyl)-hydrazinocarbonylmethyl]-5-bromo-2-methoxy-benzoic acid hydrochloride |
| 24 | 4-[N-(4-benzenesulfinyl-phenyl)-N-(2-piperidin-1-yl-phenyl)-hydrazinocarbonylmethyl]-5-bromo-2-methoxy-benzoic acid hydrochloride |
| 25 | 2-methoxy-4-{(E)-2-[N-(4-methoxy-phenyl)-N-(2-methyl-6-piperidin-1-yl-phenyl)-hydrazinocarbonyl]-vinyl}-benzoic acid hydrochloride |
| 26 | 5-bromo-2-methoxy-4-{(E)-2-[N-[4-methoxy-phenyl]-N-(2-methyl-6-piperidin-1-yl-phenyl)-hydrazino-carbonyl]-vinyl}-benzoic acid hydrochloride |
| 27 | 4-[N-(4-benzyl-phenyl)-N-(2-methyl-6-piperidin-1-yl-phenyl)-hydrazinocarbonylmethyl]-5-bromo-2-methoxy-benzoic acid hydrochloride |
| 28 | 5-bromo-2-methoxy-4-[N-(4'-methoxy-biphenyl-4-yl)-N-(2-methyl-6-piperidin-1-yl-phenyl)-hydrazino-carbonyl-methyl]-benzoic acid hydrochloride |
| 30 | 4-[N-(acetylamino-methyl)-phenyl]-N-(2-methyl-6-piperidin-1-yl-phenyl)-hydrazinocarbonylmethyl]-5-bromo-2-methoxy-benzoic acid hydrochloride |
| 31 | 5-bromo-4-[N-(4-cyano-phenyl)-N-(2-methyl-6-piperidin-1-yl-phenyl)-hydrazinocarbonylmethyl]-2-methoxy-benzoic acid hydrochloride |
| 32 | 4-[N-(4'-acetyl-phenyl)-N-(2-methyl-6-piperidin-1-yl-phenyl)-hydrazinocarbonylmethyl]-5-bromo-2-methoxy-benzoic acid hydrochloride |
| 33 | 5-bromo-2-methoxy-4-[N-(4'-methoxy-2-methyl-biphenyl-4-yl)-N-(2-methyl-6-piperidin-1-yl-phenyl)-hydrazinocarbonylmethyl]-benzoic acid hydrochloride |

The object of the present invention is also the pharmaceutical compositions comprising at least one compound of formula (I), associated with a pharmaceutically acceptable excipient.

The pharmaceutical compositions according to the invention may be compositions which may be administered into the organism via any administration route. In an non-exhaustive way, the administration route of the pharmaceutical compositions according to the invention may be topical, enteral or parenteral, preferably a buccal, conjunctive, cutaneous, endotracheal, intradermal, intra-epidermal, intramuscular, intravascular, laryngeal, nasal, ophthalmic, oral, rectal, respiratory, sub-cutaneous, transcutaneous or vaginal administration. It is generally advantageous to formulate such pharmaceutical compositions as a single dose. Each dose then comprises a predetermined amount of the active ingredient, associated with the vehicle, suitable excipients and/or adjuvants, calculated in order to obtain a given therapeutic effect. As an example of a single dose which may be administered via an oral route, mention may be made of tablets, gelatin capsules, granules, powders and oral solutions or suspensions. As an example of single dose which may be administered via a topical route (notably for local treatment of external genital and perianal warts), mention may be made of ovules, gels, creams, lotions, solutions and patches.

The suitable formulations for the selected dosage forms are known and described for example in Remington, The Science and Practice of Pharmacy, 19$^{th}$ edition, 1995, Mack Publishing Company and may therefore be easily prepared by one skilled in the art.

It is known that dosage varies from one individual to the other, depending on the nature and the intensity of the disease, the selected administration route, the weight, the age, and the sex of the patient; accordingly the effective dosages should be determined according to these parameters by the specialist in this matter. As an indication, the effective dosages may range between 1 and 500 mg daily.

The object of the present invention is also the use of the compounds of formula (I) for treating or preventing an infection by the papilloma virus, preferably in humans.

The object of the present invention is also the use of the compounds of formula (I) for inhibiting the replication of the papilloma virus by inhibiting the formation of the E1/E2 protein complex.

The object of the present invention is further the use of the compounds of formula (I) for preparing a drug intended for treating or preventing infection by the papilloma virus, preferably in humans.

The object of the present invention is in particular the use of compounds of formula (I) for preparing a drug intended for treating or preventing infection by a low risk papilloma virus, such as HPV6, HPV7, HPV11, HPV13, HPV32, HPV34, HPV40, HPV42, HPV43, HPV44, HPV53, HPV54, HPV55, HPV57, HPV58, HPV74, HPV91.

The object of the present invention is in particular the use of compounds of formula (I) for preparing a drug intended for treating or preventing an infection by HPV6 and/or HPV11.

Thus, the object of the present invention is also the use of compounds of formula (I) for preparing a drug intended for treating or preventing lesions and diseases associated with infections by the papilloma virus.

The object of the present invention is in particular the use of compounds of formula (I) for preparing a drug intended for treating and preventing anogenital warts, such as acuminated condylomas and plane condylomas, laryngeal, conjunctive or buccal papillomas and other epithelial lesions such as respiratory recurrent papillomatoses and intra-epithelial neoplasias of low grade and of high grade, bowenoid papuloses, warts (verruca vulgaris, verruca plantaris, myrmecia wart, surface warts, verruca plana . . .), epidermodysplasia verruciformis, carcinomas, in particular anogenital carcinomas, and all the lesions which are associated with the papilloma virus.

The object of the present invention is in particular the use of compounds of formula (I) for preparing a drug intended for treating or preventing anogenital warts, such as acuminated condylomas and plane condylomas, laryngeal, conjunctive or buccal papillomas and other epithelial lesions, such as respiratory recurrent papillomatoses and low grade intra-epithelial neoplasias and all the lesions which are associated with the papilloma virus.

The compounds, objects of the present invention, may be prepared according to the various synthesis routes described hereafter.

The compounds wherein $G_2$ represents the

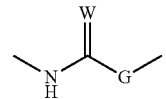

radical as defined earlier may be prepared in the following way.

When W represents an oxygen atom, ester precursors of compounds of formula (I) are obtained from intermediates of the following formulae (II) and (III):

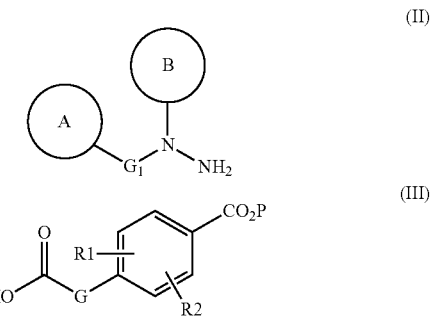

In formula (II), A, B and $G_1$, are as defined earlier. In formula (III), $R_1$, $R_2$ and G, are as defined earlier and P represents a group protecting an acid function, such as a linear or branched ($C_1$-$C_4$)alkyl.

In this case, peptide coupling is carried out between the compounds (II) and (III) for example in the presence of EDCI in a basic and apolar medium in order to lead to the compound of formula (IV):

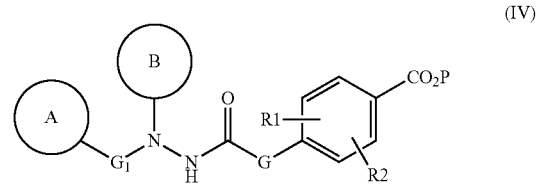

The compound (IV) may also be obtained in the following way. The compound (III) is transformed into the corresponding acid chloride of formula (V) by the action of thionyl chloride for example,

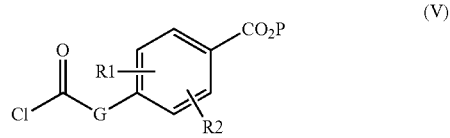

wherein $R_1$, $R_2$, G and P are as defined earlier and which are reacted on the compound (II).

Next, deprotection of the —$CO_2P$ group of the compound of formula (IV) is performed by hydrolysis, in order to obtain the compound of formula (I)

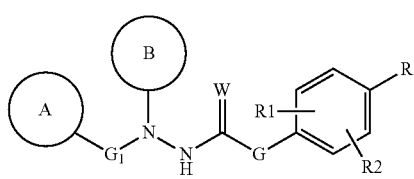
(I)

wherein W represents an oxygen atom and R₃ is as defined earlier.

If necessary, the compound of formula (I) obtained upon completion of the deprotection step or else the compound of formula (IV) is reacted with Lawesson's reagent, so that the compound of formula (VI) may be obtained:

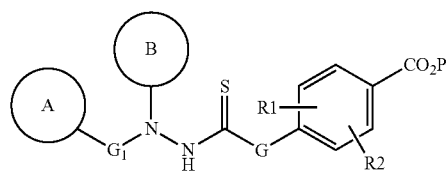
(VI)

which, after hydrolysis, corresponds to the case when W represents a sulfur atom in formula (I). Lawesson's reagent may for example be [2,4-bis(4-methoxyphenyl)1,3-dithia-2,4-diphosphetane-2,4-disulfide (Lawesson et al. *Bull. Soc. Chim Belg.* 1978, 87, 229).

In the case when $G_1$ represents a bond, the compounds of formula (II) may be obtained from compounds of formula (VII):

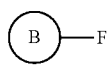
(VII)

wherein B is as defined earlier.

The compounds of formula (VII) are submitted to an aromatic nucleophilic substitution, in a basic and polar medium in the presence of compounds (VIII) of formula.

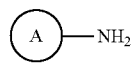
(VIII)

wherein A is as defined earlier and $G_1$ represents a bond, and compounds of formula (IX) are obtained:

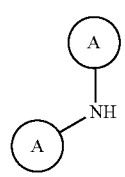
(IX)

wherein A and B are as defined earlier.

In the case when $G_1$ represents a hydrocarbon chain as defined in formula (I), the compound of formula (X) is reacted:

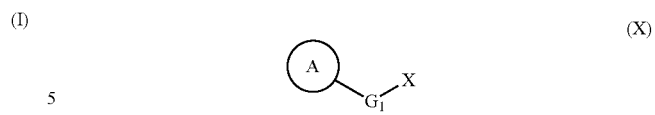
(X)

wherein A and $G_1$ are as defined earlier and X represents a halogen atom, under basic and polar conditions, with a compound of formula (XI):

(XI)

wherein B is as defined earlier, and compounds of formula (XII) are obtained:

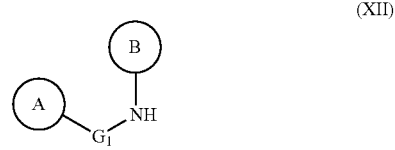
(XII)

wherein A, B and $G_1$ are as defined earlier;

The compounds of formulae (IX) and (XII) are put into the presence of sodium nitrite in an acid medium and then reduced by a hydride, for example lithium aluminium hydride (*J. Org. Chem.* 1953, 18, 971, *J. Org. Chem.* 1954, 19, 1157, and *J. Am. Chem. Soc.* 1952, 74, 3192) in order to obtain the compounds of formula (II) as defined earlier.

In the case when R₂ represents a hydrogen or bromine atom, the compounds of formula (III) may be obtained according to methods of the literature (*J. Med. Chem.* 1998, 41, 5219 or WO 0135900).

In the case when R₂ represents a chlorine atom, the compounds of formula (III) may be obtained by reacting sulfuryl chloride in an acid medium with a precursor of formula (XIII):

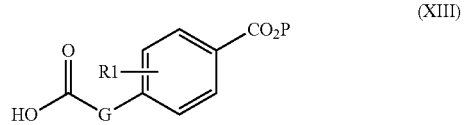
(XIII)

wherein $R_1$, G and P are as defined earlier.

The compounds of formulae (VII), (VIII), (X) and (XI) are either commercial compounds or compounds obtained according to known methods of organic synthesis easily accessible and easily understood by one skilled in the art.

In the preferred case when B is a phenyl substituted with a piperidine, compounds of formula (I) may be prepared according to the following synthesis route.

In the case when $G_1$ represents a bond, compounds of formula (II) may be obtained from compounds of formula (XIV):

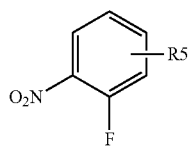

(XIV)

wherein R$_5$ is as defined earlier.

The compounds of formula (XIV) are submitted to an aromatic nuclophilic substitution in a basic and polar medium in the presence of compounds (VIII), and compounds of formula (XV) are obtained:

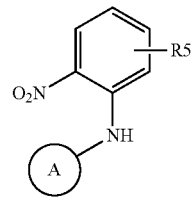

(XV)

wherein A and R$_5$ are as defined earlier.

The compounds of formula (XV) are reduced by tin chloride in a polar medium (*Tet. Lett.* 1984, 25 (8), 839) and then reacted with a dibromoalkane, for example dibromopentane in a basic and apolar medium (*Bioorg. Med. Chem. Lett.* 1996, 6 (5), 563) leading to the compounds of formula (XVI):

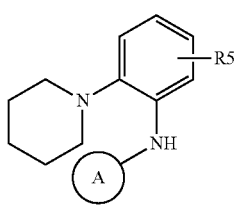

(XVI)

wherein A and R$_5$ are as defined earlier.

In the case when G$_1$ represents a hydrocarbon chain, as defined in formula (I), the compound of formula (X) is reacted under basic and polar conditions, with a compound of formula (XVII):

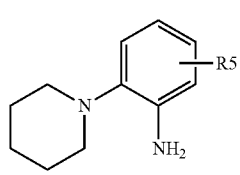

(XVII)

wherein R$_5$ is as defined earlier, and the compounds of formula (XVIII) are obtained:

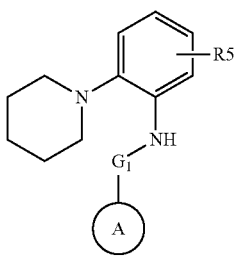

(XVIII)

wherein A, G$_1$ and R$_5$ are as defined earlier.

The compounds of formula (XVI) and (XVIII) are put into the presence of sodium nitride in an acid medium and then reduced by a hydride, for example lithium aluminium hydride in order to obtain the compounds of formula (II) as defined earlier.

In the particular case when A represents a substituted phenyl and G$_1$ is a bond, the compounds of formula (I) may be prepared according to the following synthesis route.

The compound of formula (XIX) is reacted:

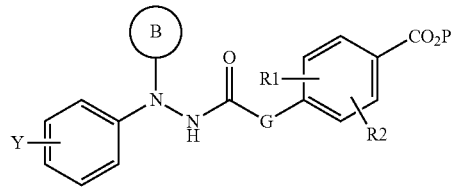

(XIX)

wherein B, G, R$_1$, R$_2$ and P are as defined earlier and Y represents a halogen such as bromine or iodine or a triflate group, under basic conditions for coupling to palladium, with a compound of formula (XX):

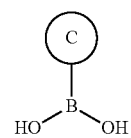

(XX)

wherein C represents an aryl or a heterocycle substituted in various ways, leading to the compound (XXI) of formula:

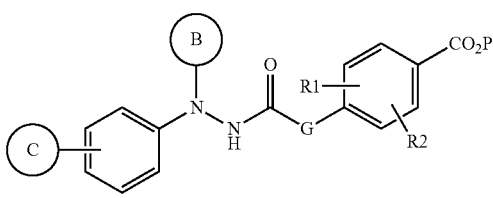

(XXI)

wherein B, C, G, R$_1$, R$_2$ and P are as defined earlier.

Next, the compound (XXI) is reacted under basic saponification conditions in order to lead to the compound of general formula (I).

The compounds wherein

G₂ represents the

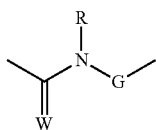

radical as defined earlier may be prepared in the following way.

The compounds of formula (IX) or (XII) as described earlier are reacted with a compound of formula (XXII):

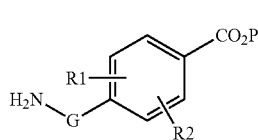

(XXII)

wherein R₁, R₂, G and P are as defined earlier,
either directly in the presence of triphosgene for example or by prior transformation of one of the precursors into carbamoyl chloride. And a final hydrolysis is then carried out.

The compound (XXII) may be obtained from the compound (XXIII) of formula:

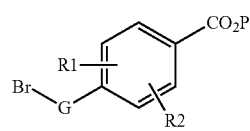

(XXIII)

wherein R₁, R₂, G and P are as defined earlier,
by reacting the compound (XXIII) in the presence of hexamethylenetetramine (HMTA) in an apolar solvent followed by acid treatment.

The compounds wherein

G₂ represents the

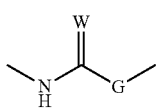

radical as defined earlier may also be prepared in the following way.

When W represents an oxygen atom, the ester precursors of the compounds of formula (I) are obtained from the following intermediates of formulae (XXIV) and (V):

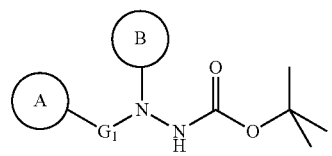

(XXIV)

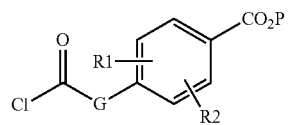

(V)

In formula (XXIV), A, B and G₁, are as defined earlier. In formula (V), R₁, R₂ and G are as defined earlier and P represents a group protecting an acid function, such as a linear or branched C₁-C₄ alkyl.

In this case, the compound (V) is reacted on the compound (XXIV) in an acid medium in order to lead to the compound of formula (IV):

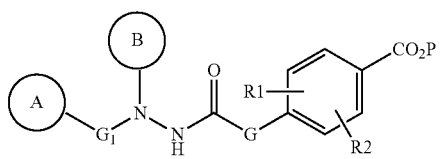

(IV)

Next, deprotection of the —CO₂P group of the compound of formula (IV) is performed by hydrolysis, in order to obtain the compound of formula (I):

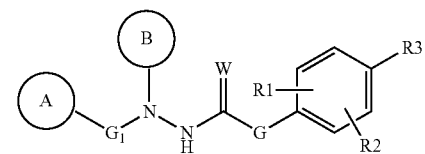

(I)

wherein W represents an oxygen atom and R₃ is as defined earlier.

In the preferred case, when B is a phenyl substituted with a piperidine and when G₁ represents a bond, the compounds of formula (XXIV) may be obtained from compounds of formula (XIV):

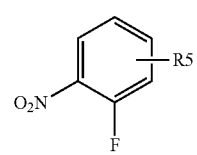

(XIV)

wherein R₅ is as defined earlier.

The compounds of formula (XIV) are submitted to an aromatic nucleophilic substitution in a polar medium in the presence of commercial Boc-hydrazine, and the compounds of formula (XXV) are obtained:

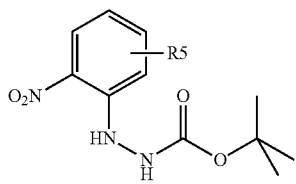
(XXV)

wherein R₅ is as defined earlier.

The compound of formula (XXV) is put into the presence of manganese oxide (*Org. Letters,* 2006, 8, 1, 43) and then submitted to an N-arylation reaction leading to the compounds of formula (XXVI):

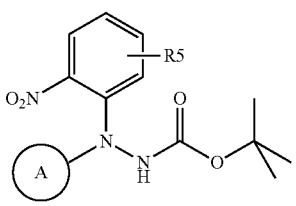
(XXVI)

wherein A and R₅ are as defined earlier.

The compounds of formula (XXVI) are reduced by catalytic hydrogenation and then reacted with a dibromoalkane or an acid chloride, for example 5-bromovaleryl chloride, in a basic and apolar medium, and then cyclized in a basic and polar medium such as by sodium hydride in dimethylformamide and finally reduced by borane, in order to lead to the compound of formula (XXVII):

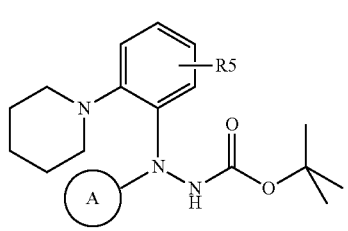
(XXVII)

wherein A and R₅ are as defined earlier.

The object of the present invention is also the synthesis intermediates corresponding to the compounds (II) grouped in the Table (II).

TABLE II

| | |
|---|---|
| a | N-(4-methoxy-phenyl)-N-(2-piperidin-1-yl-phenyl)-hydrazine |
| b | N-(2-piperidin-1-yl-phenyl)-N-(4-trifluoromethoxy-phenyl)-hydrazine |
| c | N-(3-methoxy-benzyl)-N-(2-piperidin-1-yl-phenyl)-hydrazine |
| d | N-(4-benzyloxy-phenyl)-N-(2-piperidin-1-yl-phenyl)-hydrazine |
| e | N-[4-(4-fluoro-phenoxy)-phenyl]-N-(2-piperidin-1-yl-phenyl)-hydrazine |
| f | N-[2-(4-methoxy-phenyl)-ethyl]-N-(2-piperidin-1-yl-phenyl)-hydrazine |
| g | N-(4-methoxy-phenyl)-N-(2-methyl-6-piperidin-1-yl-phenyl)-hydrazine |

TABLE II-continued

| | |
|---|---|
| h | N-(4-methoxy-benzyl)-N-(2-piperidin-1-yl-phenyl)-hydrazine |
| i | N-(4-cyclohexyl-phenyl)-N-(2-piperidin-1-yl-phenyl)-hydrazine |
| j | N-(2-methyl-6-piperidin-1-yl-phenyl)-N-(4-trifluoromethoxy-phenyl)-hydrazine |
| k | N-(4'-methoxy-biphenyl-4-yl)-N-(2-piperidin-1-yl-phenyl)-hydrazine |
| l | N-(4-cyclohexyloxy-phenyl)-N-(2-piperidin-1-yl-phenyl)-hydrazine |
| m | N-(4-phenoxy-phenyl)-N-(2-piperidin-1-yl-phenyl)-hydrazine |
| n | N-[4-(4-chloro-phenoxy)-phenyl]-N-(2-piperidin-1-yl-phenyl)-hydrazine |
| o | N-[4-(4-fluoro-phenoxy)-phenyl]-N-(2-methyl-6-piperidin-1-yl-phenyl)-hydrazine |
| p | N-(4-benzyl-phenyl]-N-(2-piperidin-1-yl-phenyl)-hydrazine |
| q | N-(4-bromo-phenyl)-N-(2-piperidin-1-yl-phenyl)-hydrazine |
| r | N-(3-phenoxy-phenyl)-N-(2-piperidin-1-yl-phenyl)-hydrazine |
| s | N-(4-phenylsulfanyl-phenyl)-N-(2-piperidin-1-yl-phenyl)-hydrazine |
| t | N-(4-benzyl-phenyl)-N-(2-methyl-6-piperidin-1-yl-phenyl)-hydrazine |
| u | N-(4'-methoxy-biphenyl-4-yl)-N-(2-methyl-6-piperidin-1-yl-phenyl)-hydrazine |
| v | N-(4-benzoyl-phenyl)-N-(2-piperidin-1-yl-phenyl)-hydrazine |
| w | N-[4'-(2-methyl-[1,3]dithian-2-yl)-biphenyl-4-yl]-N-(2-methyl-6-piperidin-1-yl-phenyl)-hydrazine |
| x | N-(4'-methoxy-2-methyl-biphenyl-4-yl)-N-(2-methyl-6-piperidin-1-yl-phenyl)hydrazine |

The following examples illustrate the invention but do not limit it by any means.

The starting products used are commercial products or products prepared according to known operating procedures from commercial compounds or known to one skilled in the art. The different preparations lead to synthesis intermediates useful for preparing the compounds of the invention.

The structures of the compounds described in the examples and in the preparations were determined according to the usual spectrophotometric techniques (nuclear magnetic resonance (NMR), mass spectrometry (MS), including electrospray (ES), melting point (MP) . . .) and purity was determined by high performance liquid chromatography (HPLC) and confirmed by elementary analysis.

Abbreviations used in the operating procedures:

AIBN: 2,2'-azobis(2-methylpropionitrile)

TLC: thin layer chromatography

EDCI: 1-(3-dimethylaminopropyl)-3-ethylcarbo-diimide hydrochloride

DMAP: 4-dimethylaminopyridine

DMSO: dimethylsulfoxide

DIPEA: N,N-diisopropylethylamine

HOBt: 1-hydroxybenzotriazole

TFA: trifluoroacetic acid

Preparation 1 methyl 4-carboxymethyl-2-methoxy-benzoate

Methyl 4-carboxymethyl-2-methoxy-benzoate may be prepared according to the method described in *J. Med. Chem.* 1998, 41, 5219 or patent WO 0135900.

Preparation 2 methyl 5-bromo-4-carboxymethyl-2-methoxy-benzoate

Methyl 5-bromo-4-carboxylmethyl-2-methoxy-benzoate is obtained from the preparation 1 according to the procedure described in WO 0135900.

Preparation 3 methyl 5-chloro-4-carboxymethyl-2-methoxy-benzoate

To 300 mg of methyl 4-carboxymethyl-2-methoxy-benzoate from preparation 1 placed in 6 mL of acetic acid, are added 110 µL of sulfuryl chloride (1 equivalent). The whole is refluxed for 6 hours. After evaporation of the solvent, the reaction crude product is purified on silica gel (petroleum ether/ethyl acetate: 80/20 then 60/40) leading to 165 mg of the desired compound.
Yield: 47%
HPLC: 96%
MS: MH$^+$ 259/261

Preparation 4 methyl 4-((E)-2-carboxy-vinyl)-2-methoxy-benzoate

Stage 1: methyl 4-bromomethyl-2-methoxy-benzoate

To 5.38 g of methyl 2-methoxy-4-methyl benzoate in 20 mL of carbon tetrachloride, are added 5.3 g of N-bromosuccinimide (1 equivalent) and 490 mg of AIBN (0.1 equivalent) away from direct light. The whole is refluxed by heating overnight. The reaction medium is evaporated under reduced pressure and then purified on silica gel (petroleum ether/ethyl acetate: 90/10) leading to 3.73 g of the desired product.
Yield: 48%
$^1$H NMR (CDCl$_3$, 300 MHz) δ (ppm): 7.76 (d, 1H), 6.99 (m, 2H), 4.46 (s, 2H), 3.92 (s, 3H), 3.88 (s, 3H)
HPLC: 96%
MS: MH$^+$ 259/261

Stage 2: methyl 4-Hydroxymethyl-2-methoxy-benzoate

To 1.5 g of the product obtained in the previous stage in 25 mL of dioxane is added a suspension of 2.55 g (4.4 equivalents) of calcium carbonate in 25 mL of water. The whole is heated for 6 hours at 100° C. After evaporation of the reaction medium, the crude product is taken up in dichloromethane, acidified with a 1 N hydrochloric acid solution. The reaction medium is extracted several times with dichloromethane, the collected organic phases are then dried on magnesium sulfate, filtered and evaporated under reduced pressure, leading to 1.10 g of the desired product.
Yield: 96%
$^1$H NMR (CDCl$_3$, 300 MHz) δ (ppm): 7.78 (d, 1H), 7.01 (m, 1H), 6.93 (d, 1H), 4.73 (s, 2H), 3.91 (s, 3H), 3.88 (s, 3H)

Stage 3: methyl 4-formyl-2-methoxy-benzoate

To 1.10 g of the product obtained in the previous stage in 20 mL of dioxane are added 4.87 g of activated manganese oxide (10 equivalents). The whole is stirred at room temperature for 24 hours, and then filtered on celite. The filtrate is evaporated under reduced pressure and the obtained residue is purified by chromatography on silica gel (petroleum ether/ethyl acetate: 90/10 and then 80/20) leading to 540 mg of the desired product.
Yield: 50%
$^1$H NMR (CDCl$_3$, 300 MHz) δ (ppm): 10.02 (s, 1H), 7.89 (d, 1H), 7.48 (m, 2H), 3.97 (s, 3H), 3.92 (s, 3H)

Stage 4: methyl 4-((E)-2-tert-butoxycarbonyl-vinyl)-2-methoxy-benzoate

To 720 µL of tert-butyl diethylphosphonoacetate (1.1 equivalents) in 3 mL of tetrahydrofurane cooled to 0° C. under an inert atmosphere are added 307 mg of sodium tert-butanolate (1.15 equivalents). The whole is stirred for 30 minutes at 0° C. and then for 1 hour at room temperature. A solution cooled to 0-4° C. of 540 mg of aldehyde obtained in stage 3 in 1 ml of tetrahydrofurane is added dropwise to the previous mixture also cooled to 0° C. Stirring is maintained at this temperature for 30 minutes before letting the temperature rise back to room temperature for 2 hours. The medium is hydrolyzed with a saturated solution of ammonium chloride and extracted with ethyl acetate several times. The collected organic phases are washed with water, and then dried on magnesium sulfate, filtered and evaporated under reduced pressure. The reaction crude product is purified by chromatography on silica gel (petroleum ether/ethyl acetate: 95/5) leading to 500 mg of the expected product.
Yield: 61%
$^1$H NMR (DMSO, 300 MHz) δ (ppm): 7.48-7.66 (bulk aromatic, 3H), 6.70 (d, 1H), 3.87 (s, 3H), 3.79 (s, 3H), 1.49 (s, 9H)
HPLC: 93%
MS: MH$^+$ 293

Stage 5: methyl 4-((E)-2-carboxy-vinyl)-2-methoxy-benzoate

To 100 mg of diester obtained in the previous stage in 1.6 mL of dichloromethane are added 0.8 mL of trifluoroacetic acid. The whole is stirred for one hour at room temperature and then evaporated under reduced pressure with a toluene and dichloromethane mixture as co-solvents.
Yield: 99%
$^1$H NMR (DMSO, 300 MHz) δ (ppm): 7.57-7.67 (m, 2H), 7.47 (s, 1H), 7.32 (d, 1H), 6.67 (d, 1H), 3.87 (s, 3H), 3.79 (s, 3H)
HPLC: 90%

Preparation 5 methyl 5-bromo-4-((E)-2-carboxy-vinyl)-2-methoxy-benzoate

Stage 1: methyl 5-bromo-4-bromomethyl-2-methoxy-benzoate

To 2.5 g of methyl 2-methoxy-4-methyl benzoate in 15 mL of acetic acid are added dropwise 550 µL of bromine (1.1 equivalents) at room temperature. The whole is stirred for one night, until complete disappearance of the starting product (tracked by TLC). The reaction medium, hydrolyzed by a 1 N soda solution, is extracted with ethyl acetate. The organic phases are dried on magnesium sulfate and then concentrated under reduced pressure, leading to 2.72 g of a pale yellow oil which crystallizes.
Yield: 83%
$^1$H NMR (CDCl$_3$, 300 MHz) δ (ppm): 7.98 (s, 1H), 7.06 (s, 1H), 4.55 (s, 2H), 3.92 (s, 3H), 3.89 (s, 3H)
HPLC: 85%
MS: MH$^+$ 336/338/340

Stage 2: methyl 5-bromo-4-hydroxymethyl-2-methoxy-benzoate

The product (880 mg) is obtained according to the method of stage 2 of preparation 4 from 1.3 g of product from the previous stage in the presence of 1.7 g of calcium carbonate.
Yield: 83%
$^1$H NMR (CDCl$_3$, 300 MHz) δ (ppm): 7.96 (s, 1H), 7.20 (s, 1H), 4.75 (s, 2H), 3.92 (s, 3H), 3.88 (s, 3H)
HPLC: 96%
MS: MH$^+$ 275/277

Stage 3: methyl 5-bromo-4-formyl-2-methoxy-benzoate

The product (725 mg) is obtained according to the method of stage 3 of preparation 4, by using 875 mg of the previous alcohol in the presence of 2.8 g of activated manganese oxide.
Yield: 83%
$^1$H NMR (CDCl$_3$, 300 MHz) δ (ppm): 10.33 (s, 1H), 8.01 (s, 1H), 7.49 (s, 1H), 3.95 (s, 3H), 3.92 (s, 3H)
HPLC: 96%
MS: MH$^+$ 273/275

Stage 4: methyl 5-bromo-4-((E)-2-tert-butoxycarbonyl-vinyl)-2-methoxy-benzoate The product (860 mg) is obtained according to the method of stage 4 of preparation 4, by using 725 mg of the previous aldehyde in the presence of 688 μL of tert-butyl diethylphosphonoacetate and 293 mg of sodium tert-butanolate.
Estimated yield: 87%
$^1$H NMR (CDCl$_3$, 300 MHz) δ (ppm): 8.00 (s, 1H), 7.89 (d, 1H), 7.13 (s, 1H), 6.34 (d, 1H), 3.92 (s, 3H), 3.89 (s, 3H), 1.55 (s, 9H)
HPLC: 63%
MS: MH$^+$ 371/373

Stage 5: methyl 5-bromo-4-((E)-2-carboxy-vinyl)-2-methoxy-benzoate

The product (489 mg) is obtained according to the method of stage 5 of preparation 4, by using 860 mg of the previous cinnamic ester in the presence of 5 mL of trifluoroacetic acid.
Yield: 67%
$^1$H NMR (DMSO, 300 MHz) δ (ppm): 7.88 (s, 1H), 7.75 (d, 1H), 7.57 (s, 1H), 6.83 (d, 1H), 3.90 (s, 3H), 3.80 (s, 3H)
HPLC: 89%
MS: MH$^+$ 315/317

Example 1

5-bromo-2-methoxy-4-[N-(4-methoxy-phenyl)-N-(2-piperidin-1-yl-phenyl)-hydrazinocarbonylmethyl]-benzoic acid hydrochloride (1)

Stage 1: (4-methoxy-phenyl)-(2-nitro-phenyl)-amine

To 3.7 mL of 2-fluoro-nitrobenzene are added 8.73 g of 4-methoxyaniline (2 equivalents). The whole is heated to 110° C. overnight. The medium is taken up in ethyl acetate, successively washed with water, a saturated solution of sodium bicarbonate and then with a saturated solution of sodium chloride. The organic phase is dried on magnesium sulfate, filtered and then concentrated under reduced pressure. With silica gel chromatography of the residue (petroleum ether/ethyl acetate: 90/10) 8.63 g of the desired product are isolated.
Yield: 99%
$^1$H NMR (DMSO, 300 MHz) δ (ppm): 9.35 (s, 1H), 8.10 (d, 1H), 7.45 (t, 1H), 7.25 (d, 2H), 6.98 (m, 3H), 6.79 (t, 1H), 3.78 (s, 3H)
HPLC: 100%

Stage 2: N-(4-methoxy-phenyl)-benzene-1,2-diamine

To a solution of 4 g of the product obtained in the previous stage in 80 mL of ethanol are added 18.5 g of tin chloride hydrate (5 equivalents). The whole is refluxed for 5 hrs and then stirred at room temperature overnight. The medium is hydrolyzed under cold conditions, adjusted to a pH of 8 with a saturated solution of sodium bicarbonate and extracted with ethyl acetate several times. The collected organic phases are dried on magnesium sulfate, filtered and evaporated in vacuo. The obtained residue is purified by silica gel chromatography (toluene and then toluene/ethyl acetate: 95/5) leading to 2.9 g of the expected product.
Yield: 82%
$^1$H NMR (DMSO, 300 MHz) δ (ppm): 6.89 (d, 1H), 6.75 (m, 7H), 6.50 (t, 1H), 4.67 (s, 2H), 3.67 (s, 3H)
HPLC: 100%

Stage 3: (4-methoxy-phenyl)-(2-piperidin-1-yl-phenyl)-amine

To a solution de 2.5 g of aniline obtained earlier in 15 mL of toluene, are successively added 2.47 g of de sodium carbonate (2 equivalents) and 1.6 mL of dibromopentane (1 equivalent). The whole is refluxed for 24 hrs. After returning to room temperature, the sodium carbonate is removed by filtration and rinsed with dichloromethane. The filtrate is evaporated under reduced pressure. The obtained residue is purified by silica gel chromatography (petroleum ether, petroleum ether/ethyl acetate: 98/2) leading to 1.72 g of the desired product.
Yield: 52%
$^1$H NMR (CDCl$_3$, 300 MHz) δ (ppm): 7.10 (m, 4H), 6.92 (m, 3H), 6.78 (m, 1H), 6.52 (s, 1H), 3.81 (s, 3H), 2.86 (m, 4H), 1.71 (m, 4H), 1.60 (m, 2H)
HPLC: 100%

Stage 4: N-(4-methoxy-phenyl)-N-(2-piperidin-1-yl-phenyl)-hydrazine (a)

806 mg of the product obtained in the previous stage are solubilized in 10 mL of acetic acid. To this solution cooled between 5 and 15° C. is added dropwise a solution of 1.14 g of sodium nitride in 3 mL of water (5.8 equivalents). After 10 minutes of stirring, ice is added into the reaction medium, the formed precipitate is filtered, washed with water and then dried in vacuo.

A brown powder corresponding to the nitroso intermediate is obtained (followed by TLC and NMR).

This non-purified intermediate, taken up in 8 mL of diethyl ether, is directly cooled to 10° C. To this solution is added a suspension of 119 mg of lithium aluminium hydride (1.1 equivalents) in 2 mL of diethyl ether. The whole is stirred for 1 hr until complete disappearance of the starting product (tracked by TLC). The reaction medium is poured onto a 1 N soda solution and extracted several times with diethyl ether. The organic phase is dried, filtered and evaporated under reduced pressure leading to a residue which is purified by chromatography (petroleum ether/ethyl acetate: 95/5). 382 mg of product corresponding to hydrazine are obtained as pink oil.

Yield: 45%

$^1$H NMR (CDCl$_3$, 300 MHz) δ (ppm): 7.08 (m, 5H), 6.95 (m, 1H), 6.81 (m, 2H), 3.78 (s, 3H), 3.04 (m, 4H), 1.73 (m, 4H), 1.57 (m, 2H)

Stage 5: methyl 5-bromo-2-methoxy-4-[N-(4-methoxy-phenyl)-N-(2-piperidin-1-yl-phenyl)-hydrazinocarbonyl-methyl]-benzoate To a solution of 367 mg of the previous compound in 10 mL of dichloromethane are added 412 mg of the acid of the preparation 2 (1.1 equivalents), 260 mg of EDCI (1.1 equivalents) and 45 mg of DMAP (0.3 equivalent). The reaction medium is stirred at room temperature, and if necessary heated, until complete disappearance of the starting hydrazine (time >15 hrs) and then hydrolyzed and extracted with dichloromethane several times. The organic phases are washed with a 1 N soda solution and then with a saturated solution of sodium chloride, dried on magnesium sulfate, filtered and evaporated under reduced pressure. The obtained residue is purified by silica gel chromatography (petroleum ether/ethyl acetate: 72/25 and then 70/30) leading to 546 mg of the expected product.

Yield: 76%

$^1$H NMR (DMSO, 300 MHz) δ (ppm): 10.65 (s, 1H), 7.81 (s, 1H), 7.30 (m, 2H), 6.99 (m, 4H), 6.72 (m, 4H), 3.79 (2s broad, 8H), 3.69 (s, 3H), 2.50 (s broad, 4H), 1.12 (m, 6H)HPLC: 96%

Stage 6: 5-bromo-2-methoxy-4-[N-(4-methoxy-phenyl)-N-(2-piperidin-1-yl-phenyl)-hydrazino-carbonyl-methyl]-benzoic acid hydrochloride (1)

To a solution of 100 mg of the product obtained in stage 5, in 2 mL of dioxane are added 343 μL of a 1 N soda solution (2 equivalents). The reaction medium is stirred at room temperature for 4 hrs and then concentrated under reduced pressure. The obtained solid is taken up in a minimum of water and acidified with a 1 N hydrochloric acid solution up to a pH of 1. In the present case, extraction with dichloromethane allows the reaction crude product to be isolated. After evaporation, the residue is taken up in ether. A precipitate is formed which is filtered and washed leading to 52 mg of the expected product as a hydrochloride.

Yield: 50%

MP: 109° C. (decomposition)

Elementary analysis calculated for C$_{28}$H$_{30}$BrN$_3$O$_5$.1HCl.1.5H$_2$O: C, 53.22; H, 5.42; N, 6.65. Found: C, 52.84; H, 5.08; N, 6.24.

HPLC: 97%

MS: MH$^+$ 568/570

Example 2

5-bromo-2-methoxy-4[N-(2-piperidin-1-yl-phenyl)-N(4-trifluoromethoxy-phenyl)-hydrazinocarbonylmethyl]-benzoic acid hydrochloride(2)

Stage 1: (2-Nitro-phenyl)-(4-trifluoromethoxy-phenyl)-amine

To 374 μL of 2-fluoro-nitrobenzene in 2 mL of DMSO are added 962 μL of 4-trifluoromethoxyaniline (2 equivalents) and 636 mg of potassium tert-butanolate (1.6 equivalents). The whole is heated to 110° C. for 3 hrs. Once the reaction is completed, the medium taken up in a minimum of dichloromethane is hydrolyzed and then extracted. The organic phase is successively washed with water and then with a saturated solution of sodium chloride, dried on magnesium sulfate, filtered and concentrated under reduced pressure. A silica gel chromatography of the residue (cyclohexane and then cyclohexane/ethyl acetate: 99/1) allows 575 mg of the desired product to be isolated.

Yield: 54%

$^1$H NMR (CDCl$_3$, 300 MHz) δ (ppm): 9.43 (s, 1H), 8.22 (d, 1H), 7.43 (t, 1H), 7.25-7.38 (m, 4H), 7.19 (d, 1H), 6.83 (t, 3H)

HPLC: 97%

MS: MH$^+$ 299

Stage 2: N—-(4-Trifluoromethoxy-phenyl)-benzene-1,2-diamine

The product (600 mg) is obtained according to the method of stage 2 of Example 1, by using 570 mg of the previous derivative as a starting product and 2.16 g of tin chloride hydrate in 10 mL of ethanol.

Yield: quantitative $^1$H NMR (CDCl$_3$, 300 MHz) δ (ppm): 7.01-7.12 (m, 4H), 6.73-6.86 (m, 2H), 6.70 (m, 2H), 5.30 (s broad, 1H)

HPLC: 96%

MS: MH$^+$ 269

Stage 3: (2-Piperidin-1-yl-phenyl)-(4-trifluoromethoxy-phenyl)-amine

The product (350 mg) is obtained according to the method of stage 3 of Example 1, by using 513 mg of the previous aniline as substrate and 261 μL of dibromopentane in the presence of 405 mg of sodium carbonate in 5 mL of toluene.

Yield: 54%

$^1$H NMR (CDCl$_3$, 300 MHz) δ (ppm): 7.28 (m, 2H), 7.13 (s, 3H), 7.09 (d, 1H), 7.01 (t, 1H), 6.88 (t, 1H), 6.70 (s, 1H), 2.83 (m, 4H), 1.71 (m, 4H), 1.59 (m, 2H)

Stage 4: N-(2-Piperidin-1-yl-phenyl)-N-(4-trifluoromethoxy-phenyl)-hydrazine (b)

The product (180 mg) is obtained according to the method of stage 4 of Example 1 by using 345 mg of the previous derivative as a starting product and 410 mg of sodium nitrite in 4 mL of acetic acid leading to the nitroso intermediate which is reduced by 28 mg of lithium aluminium hydride in 4 mL of diethyl ether.

Yield: 50%

$^1$H NMR (CDCl$_3$, 300 MHz) δ (ppm): 7.04-7.22 (bulk aromatic, 8H), 3.09 (m, 4H), 1.83 (m, 4H), 1.59 (m, 2H)

MS: MH$^+$ 352

Stage 5: methyl 5-bromo-2-methoxy-4-[N-(2-piperidin-1-yl-phenyl)-N-(4-trifluoromethoxy-phenyl)-hydrazino-carbonylmethyl]-benzoate The product (250 mg) is obtained according to the method of stage 5 of Example 1, by using 176 mg of the preceding hydrazine as substrate and 167 mg of the acid of the preparation 2 as a co-substrate in the presence of 106 mg of EDCI and 18 mg of DMAP.

Yield: 78%

$^1$H NMR (CDCl$_3$, 300 MHz) δ (ppm): 9.32 and 9.35 (2s in proportions 70/30, 1H), 7.93 and 7.99 (2s in proportions 30/70, 1H), 6.74-7.50 (m, 9H), 3.70-4.07 (3s, 8H), 2.67 (m, 4H), 1.43-1.56 (m, 6H)
HPLC: 98%
MS: MH$^+$ 636/638

Stage 6: 5-bromo-2-methoxy-4[N-(2-piperidin-1-yl-phenyl)-N-(4-trifluoromethoxy-phenyl)-hydrazinocarbonylmethyl]-benzoic acid hydrochloride (2)

To a solution of 100 mg of the product obtained in stage 5 in 2 mL of dioxane is added 1.6 mL of a 1 N soda solution (10 equivalents). The reaction medium is stirred at room temperature for 4 hrs and then concentrated under reduced pressure. The obtained solid is taken up in a minimum of water and acidified with a 1 N hydrochloric acid solution up to a pH of 1. A precipitate is formed, which is filtered, taken up in ether and washed leading to 52 mg of the expected product as a hydrochloride.
Yield: 69%
MP: 157° C. (decomposition)
Elementary analysis calculated for C$_{28}$H$_{27}$BrF$_3$N$_3$O$_5$.1HCl.1H$_2$O: C, 49.68; H, 4.47; N, 6.21. Found: C, 50.01; H, 4.62; N, 5.91.
HPLC: 98%
MS: MH$^+$ 622/624

Example 3

5-bromo-2-methoxy-4-EN-(3-methoxy-benzyl)-N-(2-piperidin-1-yl-phenyl)-hydrazinocarbonylmethyl)-benzoic acid hydrochloride (3)

Stage 1: (3-methoxy-benzyl)-(2-piperidin-1-yl-phenyl)-amine

To 1 g of 2-piperidinoaniline in 10 mL of DMF are added 795 μL of 3-methoxybenzyl bromide (1 equivalent) and 1.57 g of potassium carbonate (2 equivalents). The whole is heated to 100° C. for 2-3 hrs, until disappearance of the starting aniline. The medium is poured onto ice and then extracted with ethyl acetate. The organic phase washed with water is dried on magnesium sulfate, filtered and evaporated under reduced pressure. By silica gel chromatography of the residue (cyclohexane/ethyl acetate: 99/1) 1.46 g of the desired product may be isolated.
Yield: 87%
$^1$H NMR (CDCl$_3$, 300 MHz) δ (ppm): 7.26 (m, 1H), 6.99 (m, 4H), 6.81 (d, 1H), 6.68 (t, 1H), 6.57 (d, 1H), 4.35 (s, 2H), 3.80 (s, 3H), 2.86 (s broad, 4H), 1.69 (s broad, 6H)
HPLC: 97%
MS: MH$^+$ 297

Stage 2: N-(3-Methoxy-benzyl)-N-(2-piperidin-1-yl-phenyl)-hydrazine (c)

According to the method of stage 4 of Example 1, the nitroso intermediate (376 mg) is obtained by extraction with ethyl acetate from the reaction medium buffered to pH 7 by using 353 mg of the previous derivative as starting product, and 477 mg of sodium nitrite in 3 mL of acetic acid. A suspension of 180 mg of lithium aluminium hydride (4 equivalents) in 5 mL of diethyl ether applied to this intermediate for 2 h30 with reflux leads to 138 mg of hydrazine after purification.
Yield: 37%

$^1$H NMR (CDCl$_3$, 300 MHz) δ (ppm): 7.26 (m, 1H), 6.91-7.11 (bulk aromatic, 6H), 6.80 (dd, 1H), 4.56 (s, 2H), 3.80 (s, 3H), 3.12 (m, 4H), 1.59-1.79 (m, 6H)

Stage 3: methyl 5-bromo-2-methoxy-4-[N-(3-methoxy-benzyl)-N-(2-piperidin-1-yl-phenyl)-hydrazinocarbonyl-methyl]-benzoate The product (183 mg) is obtained according to the method of stage 5 of Example 1, by using 137 mg of the previous hydrazine as a substrate and 160 mg of the acid of preparation 2 as a co-substrate in the presence of 101 mg of EDCI and 16 mg of DMAP.
Yield: 70%
HPLC: 100%
MS: MH$^+$ 596/598

Stage 4: 5-bromo-2-methoxy-4-[N-(3-methoxy-benzyl)-N-(2-piperidin-1-yl-phenyl)-hydrazinocarbonyl-methyl]-benzoic acid hydrochloride (3)

The product (152 mg) is obtained as a hydrochloride according to the method of stage 6 of Example 2, by using as a substrate the product obtained in the previous stage.
Yield: 82%
MP: 109-112° C.
Elementary analysis calculated for C$_{29}$H$_{32}$BrN$_3$O$_5$.1HCl.1.5H$_2$O: C, 53.92; H, 5.62; N, 6.50. Found: C, 54.08; H, 5.67; N, 5.79.
HPLC: 100%
MS: MH$^+$ 582/584

Example 4

4-[N(4-benzyloxy-phenyl)-N(2-piperidin-1-yl-phenyl)-hydrazinocarbonylmethyl]-5-bromo-2-methoxy-benzoic acid hydrochloride (4)

Stage 1: (4-Benzyloxy-phenyl)-(2-nitro-phenyl)-amine

To 600 μL of 2-fluoro-nitrobenzene, 6 mL of DMSO are added 1.7 g of 4-(benzyloxy)aniline (1.5 equivalents) and 1.02 g of potassium tert-butanolate (1.6 equivalents). The whole is heated to 110° C. for 1 h30. The medium is then hydrolyzed and extracted several times with ethyl acetate. The organic phases are washed with a saturated solution of sodium chloride, dried on magnesium sulfate, filtered and then concentrated under reduced pressure. A silica gel chromatography of the residue (cyclohexane/ethyl acetate: 99/1) allows 754 mg of the desired product to be isolated.
Yield: 41% $^1$H NMR (CDCl$_3$, 300 MHz) δ (ppm): 9.40 (s broad, 1H), 8.18 (d, 1H), 7.23-7.45 (m, 6H), 7.17-7.21 (m, 2H), 7.05 (m, 3H), 6.71 (t, 1H), 5.09 (s, 2H) MS: MH$^+$ 321

Stage 2: N-(4-Benzyloxy-phenyl)-benzene-1,2-diamine

The product (653 mg) is obtained according to the method of stage 2 of Example 1, by using 754 mg of the previous derivative as a starting product and 2.66 g of tin chloride hydrate in 12 mL of ethanol.
Yield: 95%
$^1$H NMR (CDCl$_3$, 300 MHz) δ (ppm): 6.68-7.37 (bulk aromatic, 13H), 5.01 (s, 2H)
HPLC: 82%
MS: MH$^+$ 291

Stage 3: (4-benzyloxy-phenyl)-(2-piperidin-1-yl-phenyl)-amine

To a solution of 653 mg of aniline obtained previously in 4 mL of toluene, are successively added 940 µL of DIPEA (2.4 equivalents) and 305 µL of dibromopentane (1 equivalent). The whole is refluxed for 2 hrs until complete disappearance of the starting aniline. After returning to room temperature, the reaction medium is hydrolyzed and extracted several times with ethyl acetate. The organic phases are washed with water, dried on magnesium sulfate, filtered and evaporated under reduced pressure. The obtained residue is purified by silica gel chromatography (cyclohexane and then cyclohexane/ethyl acetate: 99.5/0.5) leading to 480 mg of the desired product.

Yield: 60%
$^1$H NMR (CDCl$_3$, 300 MHz) δ (ppm): 7.31-7.41 (m, 5H), 7.05-7.15 (m, 4H), 6.95 (m, 3H), 6.78 (t, 3H), 6.53 (s broad, 1H), 5.06 (s, 2H)
HPLC: 94%
MS: MH$^+$ 359

Stage 4: N-(4-benzyloxy-phenyl)-N-(2-piperidin-1-yl-phenyl)-hydrazine (d)

The product (202 mg) is obtained according to the method of stage 4 of Example 1, by using 488 mg of the previous derivative as a starting product, and 545 mg of sodium nitrite in 5 mL of acetic acid leading to the nitroso intermediate which is reduced by 74 mg of lithium aluminium hydride (2 equivalents) in 5 mL of diethyl ether.

Yield: 40%
$^1$H NMR (CDCl$_3$, 300 MHz) δ (ppm): 6.73-7.40 (bulk aromatic, 13H), 4.94 (s, 2H), 2.90 (m, 4H), 1.61 (m, 4H), 1.43 et 1.50 (m, 2H)

Stage 5: methyl 4-[N-(4-benzyloxy-phenyl)-N-(2-piperidin-1-yl-phenyl)-hydrazinocarbonyl methyl]-5-bromo-2-methoxy-benzoate The product (193 mg) is obtained according to the method of stage 5 of Example 1, by using 202 mg of the previous hydrazine as a substrate and 180 mg of the acid from preparation 2 as a co-substrate in the presence of 114 mg of EDCI and 20 mg of DMAP.

Yield: 54%
$^1$H NMR (CDCl$_2$, 300 MHz) δ (ppm): 9.37 (s broad, 1H), 7.98 (d, 1H), 7.30-7.37 (m, 5H), 7.05-7.30 (m, 2H), 6.70-6.84 (m, 5H), 4.99 (d, 2H), 3.68-4.08 (3s, 8H), 2.66 (m, 4H), 1.43-1.63 (m, 6H)

Stage 6: 4-[N-(4-benzyloxy-phenyl)-N-(2-piperidin-1-yl-phenyl)-hydrazinocarbonylmethyl]-5-bromo-2-methoxy-benzoic acid hydrochloride (4)

The product is obtained according to the method of stage 6 of Example 2, by using as a substrate the product obtained in the previous stage. With a purification by reversed phase chromatography (conditions: C18 column, 21.2×150 mm, isocratic mode 30% acetonitrile/H$_2$O+0.05% TFA, flow rate: 15 mL/min, wavelengths: 220 and 254 nm) followed by a treatment with a 1 N hydrochloric acid solution, the desired product was able to be isolated as a hydrochloride (40 mg).

Yield: 21%
MP: 114° C.
HPLC: 98%
MS: MH$^+$ 644/646

Example 5

5-bromo-4-{N[4-(4-fluoro-phenoxy)-phenyl]-N(2-piperidin-1-yl-phenyl)-hydrazinocarbonylmethyl}-2-methoxy-benzoic acid hydrochloride (5)

Stage 1: 1-Nitro-4-(4-fluoro-phenoxy)-benzene

To a solution of 1.5 mL of 4-fluoronitrobenzene in 28 mL of dimethylformamide are successively added 1.75 g of 4-fluoronitrobenzene (1.1 equivalents) and 2.15 g of potassium carbonate (1.1 equivalents). The whole is heated to 150° C. for 4 h30. After returning to room temperature, the medium is poured on ice and put under stirring for 30 min. A precipitate is formed which is filtered, rinsed with water and then dried (3.02 g).

Yield: 91%
$^1$H NMR (CDCl$_3$, 300 MHz) δ (ppm): 8.20 (d, 2H), 6.97-7.16 (bulk aromatic, 6H)

Stage 2: 4-(4-fluoro-phenoxy)-phenylamine

To a solution of 3.02 of the product obtained in the previous stage in 50 mL of ethanol are added 14.6 g of tin chloride hydrate (5 equivalents). The whole is refluxed for 1 hr. After returning to room temperature, the medium is poured on ice, basified to a pH of 10 by means of a 4 N soda solution and extracted with ethyl acetate several times. The collected organic phases are dried on magnesium sulfate, filtered and evaporated under reduced pressure leading to 2.6 g of the expected product.

Yield: quantitative
$^1$H NMR (CDCl$_3$, 300 MHz) δ (ppm): 6.82-7.03 (bulk aromatic, 6H), 6.71-6.79 (m, 2H)
MS: MH$^+$ 204

Stage 3: [4-(4-fluoro-phenoxy)-phenyl]-(2-nitro-phenyl)-amine

The product (790 mg) is obtained according to the method of stage 1 of Example 4, by using 900 µL of 2-fluoro-nitrobenzene and 2.6 g of the product obtained in the previous stage in the presence of 1.53 g of potassium tert-butanolate in 9 mL of DMSO.

Yield: 28%
$^1$H NMR (CDCl$_3$, 300 MHz) δ (ppm): 9.46 (s broad, 1H), 8.25 (d, 1H), 7.42 (t, 1H), 7.28 (m, 2H), 7.05-7.19 (bulk aromatic, 7H), 6.77 (t, 1H)
HPLC: 92%
MS: MH$^+$ 325

Stage 4: N-[4-(4-fluoro-phenoxy)-phenyl]-benzene-1,2-diamine

The product (637 mg) is obtained according to the method of stage 2 of Example 1, by using 750 mg of the previous derivative as a starting product and 2.61 g of tin chloride hydrate in 12 mL of ethanol.

Yield: 93%
$^1$H NMR (CDCl$_3$, 300 MHz) δ (ppm): 6.17-7.13 (bulk aromatic, 12H)
HPLC: 92%
MS: MH$^+$ 295

Stage 5: [4-(4-fluoro-phenoxy)-phenyl]-(2-piperidin-1-yl-phenyl)-amine

The product (715 mg) is obtained according to the method of stage 3 of Example 4, by using 635 mg of the previous derivative as a starting product, 294 μM of dibromopentane and 905 μL of DIPEA in 4 mL of toluene.

Yield: 91%

$^1$H NMR (CDCl$_3$, 300 MHz) δ (ppm): 6.79-7.26 (bulk aromatic, 12H), 6.63 (s broad, 1H), 2.84 (m, 4H), 1.74 (m, 4H), 1.60 (m, 2H)

HPLC: 98%

MS: MH$^+$ 363

Stage 6: N-[4-(4-fluoro-phenoxy)-phenyl]-N-(2-piperidin-1-yl-phenyl)-hydrazine (e)

The product (275 mg) is obtained according to the method of stage 4 of Example 1, by using 715 mg of the previous derivative as a starting product and 791 mg of sodium nitrite in 7 mL of acetic acid leading to the nitroso intermediate which is reduced by 150 mg of lithium aluminiun hydride (2 equivalents) in 7 mL of diethyl ether.

Yield: 37%

$^1$H NMR (CDCl$_3$, 300 MHz) δ (ppm): 6.83-7.19 (bulk aromatic, 12H), 3.00 (m, 4H), 1.73 (m, 4H), 1.58 (m, 2H)

Stage 7: methyl 5-Bromo-4-{N-[4-(4-fluoro-phenoxy)-phenyl]-N-(2-piperidin-1-yl-phenyl)-hydrazinocarbonylmethyl}-2-methoxy-benzoate The product (336 mg) is obtained according to the method of stage 5 of Example 1, by using 275 mg of the previous hydrazine as a substrate and 243 mg of the acid of preparation 2 as a co-substrate in the presence of 154 mg of EDCI and 27 mg of DMAP.

Yield: 69%

$^1$H NMR (CDCl$_3$, 300 MHz) δ (ppm): 9.35 (s broad, 1H), 7.98 (d, 1H), 6.73-7.50 (bulk aromatic, 13H), 3.69-4.13 (3s, 8H), 2.72 (m, 4H), 1.46-1.60 (m, 6H)

HPLC: 95%

MS: MH$^+$ 662/664

Stage 8: 5-bromo-4-{N-[4-(4-fluoro-phenoxy)-phenyl]-N-(2-piperidin-1-yl-phenyl)-hydrazinocarbonylmethyl}-2-methoxy-benzoic acid hydrochloride (5)

The product is obtained according to the method of stage 6 of Example 2, by using as a substrate the product obtained in the previous stage. With a purification by reversed phase chromatography of a fraction (conditions: C18 column, 21.2×150 mm, isocratic mode 30% acetonitrile/H$_2$O+0.05% TFA, flow rate: 15 mL/min, wave lengths 220 and 254 nm) followed by a treatment with a 1 N hydrochloric acid solution, the expected product was able to be isolated as a hydrochloride (43 mg).

Estimated yield: 44%

MP: 224-231° C.

Elementary analysis calculated for C$_{33}$H$_{31}$BrFN$_3$O$_5$.1HCl.1H$_2$O: C, 56.38; H, 4.88; N, 5.98. Found: C, 56.28; H, 4.91; N, 5.78.

HPLC: 98%

MS: MH$^+$ 648/650

Example 6

5-bromo-2-methoxy-4-{N-[2-(4-methoxyphenyl)-ethyl]-N-(2-piperidin-1-yl-phenyl)-hydrazinocarbonyl-methyl}-benzoic acid hydrochloride (6)

Stage 1: [2-(4-Methoxy-phenyl)-ethyl]-(2-piperidin-1-yl-phenyl)-amine

To 1 g of 2-piperidinoaniline in 10 mL of DMF are added 1.72 mL of 4-methoxyphenethyl chloride (2 equivalents) and 2.35 g of potassium carbonate (3 equivalents). The whole is heated to 100° C. for 60 hrs and then poured on ice and extracted with ethyl acetate. The organic phase washed with a saturated solution of sodium chloride is dried on magnesium sulfate, filtered and evaporated under reduced pressure. With several silica gel chromatographies of the residue (petroleum ether, petroleum ether/ethyl acetate: 98/2), 255 mg of the desired product were able to be isolated.

Yield: 14%

$^1$H NMR (CDCl$_3$, 300 MHz) δ (ppm): 7.17 (d, 2H), 6.99 (m, 2H), 6.86 (m, 2H), 6.66 (m, 2H), 4.77 (s broad, 1H), 3.80 (s, 3H), 3.36 (t, 2H), 2.90 (t, 2H), 2.72 (s broad, 4H), 1.57 (m, 6H)

Stage 2: N-[2-(4-methoxy-phenyl)-ethyl]-N-(2-piperidin-1-yl-phenyl)-hydrazine (f)

The product (160 mg) is obtained according to the method of stage 4 of Example 1, by using 250 mg of the previous derivative as a starting product and 322 mg of sodium nitrite in 3 mL of acetic acid leading to the nitroso intermediate which is reduced by 103 mg of lithium aluminium hydride (4 equivalents) in 3 mL of tetrahydrofurane with reflux.

Yield: 61%

$^1$H NMR (CDCl$_3$, 300 MHz) δ (ppm): 6.80-7.38 (bulk aromatic, 8H), 3.77 (s, 3H), 3.42 (t, 2H), 3.08 (t, 2H), 2.93 (m, 4H), 1.55-1.70 (m, 6H)

HPLC: 88%

MS: MH$^+$ 326

Stage 3: methyl 5-Bromo-2-methoxy-4-{N-[2-(4-methoxy-phenyl)-ethyl]-N-(2-piperidin-1-yl-phenyl)-hydrazino-carbonylmethyl}-benzoate To a solution of 160 mg of the previous compound in 3 mL of dimethylformamide, are added 164 mg of the acid of preparation 2 (1.1 equivalents), 104 mg of EDCI (1.1 equivalents) and 73 mg of HOBt (1.1 equivalents). The reaction medium is stirred at room temperature for 30 min and then heated to 40° C. for 1 h30. The reaction crude product is poured on ice and extracted with ethyl acetate several times. The collected organic phases are dried on magnesium sulfate, filtered and evaporated under reduced pressure. A first silica gel chromatography of the residue (petroleum ether/ethyl acetate: 95/5, 80/20 and then 50/50) was able to isolate the product which is then purified by reversed phase chromatography (conditions: C18 column, 21.2×150 mm, isocratic mode 30% acetonitrile/H$_2$O+0.05% TFA, flow rate: 15 mL/min, wavelengths: 220 and 254 nm) leading to 90 mg of the desired product as a TFA salt.

Yield: 25%

$^1$H NMR (DMSO, 300 MHz) δ (ppm): 12.15 (s broad, 1H), 11.53 (s, 1H), 8.06 (d, 1H), 7.92 (s, 1H), 7.54 (t, 1H), 7.42 (m, 1H), 7.32 (d, 1H), 7.03 (d, 3H), 6.76 (d, 2H), 3.86 and 3.83 (2s, 10H), 3.73 (s, 2H), 3.47 (s, 3H), 2.98 (m, 2H), 2.85 (t, 2H), 1.79 (m, 4H), 1.34 (m, 2H)

HPLC: 99%

MS: MH⁺ 610/612

Stage 4: 5-bromo-2-methoxy-4-{N-[2-(4-methoxy-phenyl)-ethyl]-N-(2-piperidin-1-yl-phenyl)-hydrazinocarbonyl-methyl}-benzoic acid hydrochloride (6)

The product (63 mg) is obtained as a hydrochloride according to the method of stage 6 of Example 2, by using as a substrate the product obtained in the previous stage.

Yield: 68%

MP: 162-176° C.

Elementary analysis calculated for: $C_{30}H_{34}BrN_3O_5 \cdot 1HCl \cdot 1.5H_2O$: C, 54.59; H, 5.80; N, 6.37. Found: C, 54.65; H, 5.31; N, 5.85.

HPLC: 90%

MS: MH⁺ 596/598

Example 7

5-bromo-2-methoxy-4-[N-(4-methoxy-phenyl)-N-(2-methyl-6-piperidin-1-yl-phenyl)-hydrazinocarbonyl-methyl]-benzoic acid hydrochloride (7)

Stage 1: (4-methoxy-phenyl)-(2-methyl-6-nitro-phenyl)-amine

The product (487 mg) is obtained according to the method of stage 1 of Example 4, by using 1 g of 2-fluoro-3-methyl-nitrobenzene and 1.19 g of 4-methoxyaniline in the presence of 1.16 g of potassium tert-butanolate in 9 mL of DMSO.

Yield: 29%

¹H NMR (CDCl₃, 300 MHz) δ (ppm): 7.99 (d, 1H), 7.37 (m, 1H), 6.96 (t, 1H), 6.78 (m, 4H), 3.78 (s, 3H), 1.99 (s, 3H)

Stage 2: N²-(4-methoxy-phenyl)-3-methyl-benzene-1,2-diamine

The product (428 mg) is obtained according to the method of stage 2 of Example 1, by using 487 mg of the previous derivative as a starting product and 2.13 g of tin chloride hydrate in 6 mL of ethanol.

Yield: 99%

¹H NMR (CDCl₃, 300 MHz) δ (ppm): 6.99 (t, 1H), 6.75 (m, 2H), 6.65 (d, 2H), 6.52 (m, 2H), 3.74 (s, 3H), 2.17 (s, 3H)

Stage 3: (4-methoxy-phenyl)-(2-methyl-6-piperidin-1-yl-phenyl)-amine

The product (250 mg) is obtained according to the method of stage 3 of Example 4, by using 425 mg of the previous derivative as a starting product, 253 μL of dibromopentane and 778 μL of DIPEA in 8 mL of toluene.

Yield: 45%

¹H NMR (CDCl₃, 300 MHz) δ (ppm): 6.95 (m, 3H), 6.78 (m, 2H), 6.67 (m, 2H), 3.77 (s, 3H), 2.73 (m, 4H), 2.10 (s, 3H), 1.59 (m, 6H)

Stage 4: N-(4-methoxy-phenyl)-N-(2-methyl-6-piperidin-1-yl-phenyl)-hydrazine (g)

According to the method of stage 4 of Example 1, the nitroso intermediate (270 mg) is obtained by extraction with dichloromethane from the reaction medium buffered to pH 7 by using 250 mg of the previous derivative as a starting product and 337 mg of sodium nitrite in 3 mL of acetic acid. A suspension of 126 mg of lithium aluminium hydride (4 equivalents) in 3 mL of tetrahydrofurane applied to this intermediate for 1 hr with reflux is able to lead to 129 mg of hydrazine after purification.

Yield: 49%

MS: MH⁺ 312

Stage 5: methyl 5-bromo-2-methoxy-4-[N-(4-methoxy-phenyl)-N-(2-methyl-6-piperidin-1-yl-phenyl)-hydrazino-carbonylmethyl]-benzoate (7a)

To a solution of 129 mg of the acid obtained in preparation 2 (1.1 equivalents) in 4 mL of dichloromethane are added 100 μL of thionyl chloride (3.3 equivalents) and 1 drop of dimethylformamide. The whole is stirred for 1 hr at room temperature and then evaporated under reduced pressure. To the thereby obtained acid chloride, taken up in 4 mL of toluene, are successively added a solution of 129 mg of the previous hydrazine in 3 mL of toluene and 65 of triethylamine (1.1 equivalents). The medium is heated overnight to 40° C. and then after returning to room temperature, hydrolyzed and extracted with ethyl acetate several times. The collected organic phases are washed with water, dried on magnesium sulfate, filtered and evaporated under reduced pressure. The obtained residue is purified by reversed phase chromatography (conditions: C18 column, 21.2×150 mm, isocratic mode 35% acetonitrile/H₂O+0.05% TFA, flow rates: 15 mL/min, wavelengths: 220 and 254 nm) leading to 110 mg of the expected product as a TFA salt.

Yield: 37%

¹H NMR (CDCl₃, 300 MHz) δ (ppm): 12.52 (s broad, 1H), 11.12 (s, 1H), 7.98 (s, 1H), 7.51 (m, 2H), 7.36 (d, 1H), 7.13 (s, 1H), 6.79 (d, 2H), 6.56 (d, 2H), 4.03 (m, 2H), 3.89 (s, 6H), 3.75 (s, 3H), 3.42 (m, 3H), 3.06 (m, 1H), 2.26 (s, 3H), 1.79-2.01 (m, 5H), 1.50 (m, 1H)

HPLC: 93%

MS: MH⁺ 596/598

Stage 6: 5-bromo-2-methoxy-4-[N-(4-methoxy-phenyl)-N-(2-methyl-6-piperidin-1-yl-phenyl)-hydrazinocarbonyl-methyl]-benzoic acid hydrochloride (7)

The product (61 mg) is obtained as a hydrochloride according to the method of stage 6 of Example 2, by using as a substrate the product obtained in the previous stage.

Yield: 53%

MP: 155-168° C.

Elementary analysis calculated for $C_{29}H_{32}BrN_3O_5 \cdot 1HCl \cdot 1.75H_2O$: C, 53.55; H, 5.66; N, 6.46. Found: C, 53.28; H, 5.69; N, 6.12.

HPLC: 100%

MS: MH⁺ 582/584

Example 8

5-bromo-2-methoxy-4-[N-(4-methoxy-benzyl)-N-(2-piperidin-1-yl-phenyl)-hydrazinocarbonylmethyl]-benzoic acid hydrochloride (8)

Stage 1: (4-methoxy-benzyl)-(2-piperidin-1-yl-phenyl)-amine

The product (644 mg) is obtained according to the method of stage 1 of Example 3, by using 1 g of 2-piperidinoaniline, 982 µL of 4-methoxybenzyl bromide (1.2 equivalents) and 1.6 g of potassium carbonate (2 equivalents) in 10 mL of DMF.

Yield: 40%

$^1$H NMR (CDCl$_3$, 300 MHz) δ (ppm): 7.42 (d, 2H), 7.11 (m, 2H), 7.01 (d, 2H), 6.81 (td, 1H), 6.75 (dd, 1H), 4.41 (s, 2H), 3.88 (s, 3H), 2.99 (s broad, 4H), 1.82 (m, 6H)

HPLC: 100%

MS: MH$^+$ 297

Stage 2: N-(4-Methoxy-benzyl)-N-(2-piperidin-1-yl-phenyl)-hydrazine (h)

The product (275 mg) is obtained according to the method of stage 4 of Example 1, by using 290 mg of the previous derivative as a starting product and 392 mg of sodium nitrite in 3 mL of acetic acid leading to the nitroso intermediate which is reduced by 140 mg of lithium aluminium hydride (4 equivalents) in 4 mL of tetrahydrofuran with reflux.

Yield: 90%

$^1$H NMR (CDCl$_3$, 300 MHz) δ (ppm): 7.23 (m, 2H), 7.10 (m, 1H), 7.00 (m, 3H), 6.87 (m, 2H), 4.47 (s, 2H), 3.82 (s, 3H), 3.10 (m, 4H), 1.59-1.77 (m, 6H)

HPLC: 96%

MS: MH$^+$ 312

Stage 3: methyl 5-bromo-2-methoxy-4-[N-(4-methoxy-benzyl)-N-(2-piperidin-1-yl-phenyl)-hydrazinocarbonylmethyl]-benzoate The product is obtained according to the method of stage 5 of Example 7, by using 161 mg of the acid of preparation 2 and 116 µL of thionyl chloride in the presence of a drop of dimethylformamide for forming the acid chloride and 150 mg of the previous hydrazine in the presence of 74 µL of triethylamine for coupling. With a purification by reversed phase chromatography (conditions: C18 column, 21.2×150 mm, isocratic mode 35% acetonitrile/H$_2$O+0.05% TFA, flow rate: 15 mL/min, wavelengths: 220 and 254 nm) 80 mg of the expected product was able to be isolated as a TFA salt.

Yield: 23%

$^1$H NMR (CDCl$_3$, 300 MHz) δ (ppm): 11.90 (s broad), 10.57 (s, 1H), 8.13 (d, 1H), 7.87 (s, 1H), 7.63 (t, 1H), 7.48 (t, 1H), 7.34 (d, 1H), 7.12 (d, 2H), 6.76 (m, 3H), 4.47 (m, 2H), 3.89 (m, 1H), 3.78, 3.86 and 3.89 (3s, 9H), 3.64 (s, 2H), 2.95-3.15 (m, 3H), 1.93 and 2.09 (2m, 5H), 1.49 (m, 1H)

HPLC: 93%

MS: MH$^+$ 596/598

Stage 4: 5-bromo-2-methoxy-4-[N-(4-methoxy-benzyl)-N-(2-piperidin-1-yl-phenyl)-hydrazinocarbonylmethyl]-benzoic acid hydrochloride (8)

The product (36 mg) is obtained as a hydrochloride according to the method of stage 6 of Example 2, by using as a substrate the product obtained in the previous stage.

Yield: 43%

MP: 140-171° C.

Elementary analysis calculated for C$_{29}$H$_{32}$BrN$_3$O$_5$.1HCl.1.75H$_2$O: C, 53.55; H, 5.66; N, 6.46. Found: C, 53.52; H, 5.58; N, 5.97.

HPLC: 98%

MS: MH$^+$ 582/584

Example 9

5-bromo-4-[N-(4-cyclohexyl-phenyl)-N-(2-piperidin-1-yl-phenyl)-hydrazinocarbonylmethyl]-2-methoxy-benzoic acid hydrochloride (9)

Stage 1: (4-cyclohexyl-phenyl)-(2-nitro-phenyl)-amine

The product (280 mg) is obtained according to the method of stage 1 of Example 4, by using 400 µL of 2-fluoro-nitrobenzene and 1 g of 4-cyclohexylaniline in the presence of 683 mg of potassium tert-butanolate in 4 mL of DMSO.

Yield: 25%

$^1$H NMR (CDCl$_3$, 300 MHz) δ (ppm): 9.47 (s broad, 1H), 8.19 (d, 1H), 7.71 (d, 1H), 7.45 (t, 1H), 7.34 (t, 1H), 7.10-7.24 (m, 3H), 6.71 (t, 1H), 2.53 (m, 1H), 1.35-1.95 (2m, 10H)

HPLC: 87%

MS: MH$^+$ 297

Stage 2: N-(4-cyclohexyl-phenyl)-benzene-1,2-diamine

The product (154 mg) is obtained according to the method of stage 2 of Example 1, by using 280 mg of the previous derivative as starting product and 1.07 g of tin chloride hydrate in 4 mL of ethanol.

Yield: 61%

$^1$H NMR (CDCl$_3$, 300 MHz) δ (ppm): 6.95-7.12 (m, 4H), 6.68-6.82 (m, 4H), 2.40 (m, 1H), 1.40 and 1.80 (2m, 10H)

HPLC: 91%

MS: MH$^+$ 267

Stage 3: (4-cyclohexyl-phenyl)-(2-piperidin-1-yl-phenyl)-amine

The product (395 mg) is obtained according to the method of stage 3 of Example 4, by using 700 mg of the preceding derivative as a starting product, 357 µL of dibromopentane and 1.1 mL of DIPEA in 10 mL of toluene.

Yield: 45%

$^1$H NMR (CDCl$_3$, 300 MHz) δ (ppm): 7.30 (m, 1H), 7.05-7.16 (m, 5H), 6.97 (t, 1H), 6.80 (t, 1H), 6.64 (s broad, 1H), 2.82 (m, 4H), 2.45 (m, 1H), 1.35-1.90 (m, 16H)

Stage 4: N-(4-Cyclohexyl-phenyl)-N-(2-piperidin-1-yl-phenyl)-hydrazine (i)

The product (80 mg) is obtained according to the method of stage 4 of Example 1, by using 200 mg of the preceding derivative as starting product and 240 mg of sodium nitrite in 3 mL of acetic acid leading to the nitroso intermediate which is reduced by 181 mg of lithium hydride and aluminium (8 equivalents) in 3 mL of tetrahydrofurane in reflux.

Yield: 38%

$^1$H NMR (CDCl$_3$, 300 MHz) δ (ppm): 6.75-7.25 (bulk aromatic, 8H), 4.75 (s broad), 2.97 (m, 4H), 2.42 (m, 1H), 1.25-1.90 (bulk aliphatic, 16H)

MS: MH$^+$ 350

Stage 5: methyl 5-bromo-4-[N-(4-cyclohexyl-phenyl)-N-(2-piperidin-1-yl-phenyl)-hydrazino carbonylmethyl]-2-methoxy-benzoate The product is obtained according to the method of stage 3 in Example 6, by using 70 mg of the previous hydrazine and 67 mg of the acid of the preparation 2 in the presence of 42 mg of EDCI and 30 mg of HOBt in 3 mL of dimethylformamide. With a purification by reversed phase chromatography (conditions: C18 column, 21.2×150 mm, isocratic mode 50% acetonitrile/$H_2O$+0.05% TFA, flow rate: 15 mL/min, wavelengths: 220 and 254 nm) 32 mg of the expected product were able to be isolated as a TFA salt.

Yield: 21%
HPLC: 93%
MS: MH$^+$ 634/636

Stage 6: 5-bromo-4-[N-(4-cyclohexyl-phenyl)-N-(2-piperidin-1-yl-phenyl)-hydrazinocarbonylmethyl]-2-methoxy-benzoic acid hydrochloride (9)

The product (22 mg) is obtained as a hydrochloride according to the method of stage 6 of Example 2, by using as a substrate the obtained product from the previous stage.

Yield: 68%
MP: 163-181° C.
Elementary analysis calculated for $C_{33}H_{38}BrN_3O_4 \cdot 1HCl \cdot 0.75H_2O$: C, 59.11; H, 6.09; N, 6.27. Found: C, 59.23; H, 6.25; N, 6.03.
HPLC: 93%
MS: MH$^+$620/622

Example 10

5-bromo-2-methoxy-4-[N-(2-methyl-6-piperidin-1-yl-phenyl)-N-(4-trifluoromethoxy-phenyl)-hydrazinocarbonylmethyl]-benzoic acid hydrochloride (10)

Stage 1: (2-methyl-6-nitro-phenyl)-(4-trifluoromethoxy-phenyl)-amine

The product (1.92 g) is obtained as a hydrochloride according to the method of stage 1 of Example 4, by using 1 g of 2-fluoro-3-methyl-nitrobenzene and 1.3 mL of 4-trifluoromethoxy-aniline in the presence of 1.16 g of potassium tert-butanolate in 10 mL of DMSO.

Yield: 95%
$^1$H NMR (CDCl$_3$, 300 MHz) δ (ppm): 8.19 (s broad), 7.97 (d, 1H), 7.45 (d, 1H), 7.10 (m, 3H), 6.74 (d, 2H), 2.11 (s, 3H)
HPLC: 75%
MS: MH$^+$ 313

Stage 2: 3-methyl-N$^2$-(4-trifluoromethoxy-phenyl)-benzene-1,2-diamine

The product (901 mg) is obtained according to the method of stage 2 of Example 1, by using 1.92 g of the preceding derivative as a starting product and 6.94 g of tin chloride hydrate in 25 mL of ethanol.

Yield: 52%
$^1$H NMR (CDCl$_3$, 300 MHz) δ (ppm): 7.07 (m, 3H), 6.73 (m, 2H), 6.53 (d, 2H), 5.10 (s broad, 1H), 3.99 (s broad, 2H), 2.18 (s, 3H)
HPLC: 90%
MS: MH$^+$ 283

Stage 3: (2-methyl-6-piperidin-1-yl-phenyl)-(4-trifluoromethoxy-phenyl)-amine The product (890 mg) is obtained according to the method of stage 3 in Example 4, by using 900 mg of the preceding derivative as starting product, 433 μL of dibromopentane and 1.3 mL of DIPEA in 15 mL of toluene.

Yield: 79%
$^1$H NMR (CDCl$_3$, 300 MHz) δ (ppm): 7.04 (m, 3H), 6.95 (d, 2H), 6.66 (d, 2H), 6.19 (s broad, 1H), 2.72 (m, 4H), 2.11 (s, 3H), 1.56 (m, 6H)
HPLC: 96%
MS: MH$^+$ 351

Stage 4: N-(2-methyl-6-piperidin-1-yl-phenyl)-N-(4-trifluoromethoxy-phenyl)-hydrazine (j)

The product (270 mg)—contaminated by the starting amine—is obtained according to stage 4 of Example 1, by using 450 mg of the preceding derivative as a starting product and 514 mg of sodium nitrite in 4 mL of acetic acid leading to the nitroso intermediate which is reduced by 355 mg of lithium aluminium hydride (8 equivalents) in 4 mL of tetrahydrofurane with reflux.

Estimated yield: 23%
MS: MH$^+$ 366

Stage 5: methyl 5-bromo-2-methoxy-4-[N-(2-methyl-6-piperidin-1-yl-phenyl)-N-(4-trifluoromethoxy-phenyl)-hydrazinocarbonylmethyl]-benzoate The product is obtained according to the method of stage 3 of Example 6, by using 400 mg of the preceding hydrazine and 365 mg of the acid of preparation 2 in the presence of 231 mg of EDCI and 163 mg of HOBt in 4 mL of dimethylformamide. With purification by reversed phase chromatography (conditions: C18 column, 21.2×150 mm, isocratic mode 35% acetonitrile/$H_2O$+0.05% TFA, flow rate: 15 mL/min, wavelengths: 220 and 254 nm) it was possible to isolate 260 mg of the expected product as a TFA salt.

Yield: 36%
$^1$H NMR (CDCl$_3$, 300 MHz) δ (ppm): 12.26 (s broad, 1H), 11.42 (s, 1H), 7.94 (s, 1H), 7.50 (m, 3H), 7.09 (m, 3H), 6.62 (d, 2H), 4.02 (m, 2H), 3.87 (s, 6H), 3.60 (m, 1H), 3.31 (m, 2H), 3.15 (m, 1H), 2.24 (s, 3H), 2.14 (m, 1H), 1.79-1.94 (m, 4H), 1.52 (m, 1H)
HPLC: 95%
MS: MH$^+$ 650/652

Stage 6: 5-bromo-2-methoxy-4-[N-(2-methyl-6-piperidin-1-yl-phenyl)-1-N-(4-trifluoromethoxy-phenyl)-hydrazino-carbonylmethyl]-benzoic acid hydrochloride (10)

The product (166 mg) is obtained as a hydrochloride according to the method of stage 6 of Example 2, by using as a substrate the product obtained in the previous stage.

Yield: 62%
MP: 128° C. (decomposition)
Elementary analysis calculated for $C_{29}H_{29}BrF_3N_3O_5 \cdot 1HCl \cdot 1H_2O$: C, 50.41; H, 4.67; N, 6.08. Found: C, 50.02; H, 4.68; N, 5.82.
HPLC: 96%
MS: MH$^+$ 636/638

Example 11

5-bromo-2-methoxy-4-[N-(4'-methoxy-biphenyl-4-yl)-N-(2-piperidin-1-yl-phenyl)-hydrazino-carbonyl-methyl]-benzoic acid hydrochloride (11)

Stage 1: (4-bromo-phenyl)-(2-nitro-phenyl)-amine

The product (6.49 g) is obtained according to the method of stage 1 of Example 4, by using 3.73 mL of 2-fluoronitrobenzene and 7.31 g of 4-bromoaniline in the presence of 6.36 g of potassium tert-butanolate in 120 mL of DMSO.
Yield: 62%
$^1$H NMR (CDCl$_3$, 300 MHz) δ (ppm): 9.38 (s broad, 1H), 8.19 (d, 1H), 7.51 (d, 2H), 7.38 (t, 1H), 7.17 (t, 3H), 6.81 (t, 1H)
HPLC: 99%
MS: MH$^+$ 293/295

Stage 2: N-(4-bromo-phenyl)-benzene-1,2-diamine

The product (571 mg) is obtained according to the method of stage 2 of Example 1, by using 723 mg of the previous derivative as a starting product and 2.78 g of tin chloride hydrate in 7 mL of ethanol.
Yield: 88%
$^1$H NMR (CDCl$_3$, 300 MHz) δ (ppm): 7.26 (d, 2H), 7.05 (m, 2H), 6.78 (m, 2H), 6.60 (d, 1H)
HPLC: 97%
MS: MH$^+$ 263/265

Stage 3: (4-bromo-phenyl)-(2-piperidin-1-yl-phenyl)-amine

The product (1.03 g) is obtained according to the method of stage 3 of Example 4, by using 1.35 g of the previous derivative as a starting product, 698 μL of dibromopentane and 2.1 mL of DIPEA in 13 mL of toluene.
Yield: 61%
$^1$H NMR (CDCl$_3$, 300 MHz) δ (ppm): 7.36 (m, 2H), 7.26 (m, 1H), 7.01-7.10 (m, 4H), 6.89 (m, 1H), 6.56 (s broad, 1H), 2.82 (t, 4H), 1.57-1.74 (m, 6H)
HPLC: 100%
MS: MH$^+$ 331/33

Stage 4: (4'-methoxy-biphenyl-4-yl)-(2-piperidin-1-yl-phenyl)-amine

To a solution of 554 mg of the brominated derivative obtained previously in 14 mL of a 50:50 methanol/toluene mixture are successively added 380 mg of phenylboronic acid (1.5 equivalents), 96 mg of palladium tetrakis (0.05 equivalents), 212 mg of lithium chloride (3 equivalents) and 4.17 mL of a 1 molar solution of calcium carbonate. The whole is refluxed for 2 hrs. The reaction crude product is extracted with ethyl acetate several times; the collected organic phases are washed with water, and then dried on magnesium sulfate, filtered and evaporated under reduced pressure.

The obtained residue is purified by silica gel chromatography (petroleum ether and then petroleum ether/ethyl acetate: 99/1) leading to 260 mg of the expected product.
Yield: 43%
$^1$H NMR (CDCl$_3$, 300 MHz) δ (ppm): 7.53 (m, 4H), 7.38 (dd, 1H), 7.25 (m, 2H), 7.12 (dd, 1H), 6.97-7.10 (m, 3H), 6.88 (td, 1H), 6.76 (s broad, 1H), 3.86 (s, 3H), 2.87 (t, 4H), 1.52-1.78 (m, 6H)
HPLC: 80%
MS: MH$^+$ 359

Stage 5: N-(4'-methoxy-biphenyl-4-yl)-N-(2-piperidin-1-yl-phenyl)-hydrazine (k)

The product (141 mg) is obtained according to the method of stage 4 of Example 1, by using 203 mg of the previous derivative as a starting product and 226 mg of sodium nitrite in 1.5 mL of acetic acid leading to the nitroso intermediate which is reduced by 179 mg of lithium aluminium hydride (8 equivalents) in 4 mL of tetrahydrofurane with reflux.
Yield: 64%
$^1$H NMR (CDCl$_3$, 300 MHz) δ (ppm): 7.49 (d, 2H), 7.38 (d, 2H), 7.14 (m, 2H), 6.93 (m, 4H), 6.87 (d, 2H), 3.84 (s, 3H), 2.92 (m, 4H), 1.39 (m, 6H)
HPLC: 90%
MS: MH$^+$ 374

Stage 6: methyl 5-bromo-2-methoxy-4-[N-(4'-methoxy-biphenyl-4-yl)-N-(2-piperidin-1-yl-phenyl)-hydrazino-carbonylmethyl]-benzoate The product is obtained according to the method of stage 3 of Example 6, by using 141 mg of the previous hydrazine and 126 mg of the acid of preparation 2 in the presence of 79 mg of EDCI and 56 mg of HOBt in 6 mL of dimethylformamide. With a purification by reversed phase chromatography (conditions C18 column, 21.2×150 mm, isocratic mode 50% acetonitrile/H$_2$O+0.05% TFA, flow rate: 15 mL/min, wavelengths: 220 and 254 nm), 9 mg of the expected product were able to be isolated as a TFA salt.
Yield (non-optimized): 3%
HPLC: 75%
MS: MH$^+$ 658/660

Stage 7: 5-bromo-2-methoxy-4-[N-(4'-methoxy-biphenyl-4-yl)-N-(2-piperidin-1-yl-phenyl)-hydrazino-carbonyl-methyl]-benzoic acid hydrochloride (11)

The product (7.3 mg) is obtained as a hydrochloride according to the method of stage 6 or Example 2, by using as a substrate the product obtained in the previous stage.
Yield: 92%
HPLC: 80%
MS: MH$^+$ 644/646

Example 12

5-bromo-4-[N-(4-cyclohexyloxy-phenyl)-N-(2-piperidin-1-yl-phenyl)-hydrazino-carbonylmethyl]-2-methoxy-benzoic acid hydrochloride (12)

Stage 1:1-cyclohexyloxy-4-nitro-benzene

To 3.9 g of cyclohexanol (1.1 equivalents) put into the presence of 2.12 g of sodium hydride (1.5 equivalents) under stirring for 10 min, is added a solution of 5 g of 4-fluoronitrobenzene in 75 mL of dimethylformamide. The whole is heated to 60° C. for 5 hrs. After returning to room temperature, the medium is hydrolyzed and the reaction crude product is extracted with ethyl acetate several times. The organic phases are dried on magnesium sulfate, filtered and evaporated under reduced pressure. With a silica gel chromatography of the residue (cyclohexane and then cyclohexane/ethyl acetate: 98/2 and 90/10) 6.06 g of the desired product are able to be isolated.
Yield: 78%

¹H NMR (CDCl₃, 300 MHz) δ (ppm): 8.16 (d, 2H), 6.92 (d, 2H), 4.37 (m, 1H), 1.98 (m, 2H), 1.81 (m, 2H), 1.35-1.65 (m, 6H)
HPLC: 98%
MS: [M+Na]⁺ 244

Stage 2: 4-cyclohexyloxy-phenylamine

The product (4.48 g) is obtained according to the method of stage 2 of Example 5, by using 6.06 g of the previous derivative as a starting product and 30.9 g of tin chloride hydrate in 59 mL of ethanol.
Yield: 87%
¹H NMR (CDCl₃, 300 MHz) δ (ppm): 6.76 (d, 2H), 6.62 (d, 2H), 4.06 (m, 1H), 3.42 (s broad, 2H), 1.95 (m, 2H), 1.78 (m, 2H), 1.28-1.60 (m, 6H)
HPLC: 88%
MS: MH⁺ 192

Stage 3: (4-cyclohexyloxy-phenyl)-(2-nitro-phenyl)-amine

The product (4.27 g) is obtained according to the method of stage 1 of Example 4, by using 2.95 mL of 2-fluoronitrobenzene and 4.48 g of the product obtained in the previous stage in the presence of 4.18 g of potassium tert-butanolate in 108 mL of DMSO.
Yield: 59%
¹H NMR (CDCl₃, 300 MHz) δ (ppm): 9.40 (s broad, 1H), 8.20 (d, 1H), 7.35 (m, 1H), 7.18 (m, 2H), 6.95-7.05 (m, 3H), 6.72 (m, 1H), 4.06 (m, 1H), 2.05 (m, 2H), 1.82 (m, 2H), 1.35-1.60 (m, 6H)
HPLC: 86%
MS: MH⁺ 313

Stage 4: N-(4-cyclohexyloxy-phenyl)-benzene-1,2-diamine

The product (3.43 g) is obtained according to the method of stage 2 of Example 1, by using 4.27 g of the previous derivative as a starting product and 15.42 g of tin chloride hydrate in 27 mL of ethanol.
Yield: 88%
¹H NMR (CDCl₃, 300 MHz) δ (ppm): 7.04 (d, 1H), 6.94 (m, 1H), 6.72-6.84 (m, 6H), 4.14 (m, 1H), 1.97 (m, 2H), 1.80 (m, 2H), 1.30-1.60 (m, 6H) HPLC: 92%
MS: MH⁺ 283

Stage 5: (4-cyclohexyloxy-phenyl)-(2-piperidin-1-yl-phenyl)-amine

The product (1.55 g) is obtained according to the method of stage 3 of Example 4, by using 3.43 g of the previous derivative as a starting product, 1.65 mL of dibromopentane and 5.1 mL of DIPEA in 49 ml of toluene.
Yield: 36%
¹H NMR (CDCl₃, 300 MHz) δ (ppm): 7.07 (m, 4H), 6.80-6.98 (m, 3H), 6.78 (m, 1H), 6.52 (s broad, 1H), 4.21 (m, 1H), 2.86 (m, 4H), 1.35-2.05 (m, 16H)
HPLC: 99%
MS: MH⁺ 351

Stage 6: N-(4-cyclohexyloxy-phenyl)-N-(2-piperidin-1-yl-phenyl)-hydrazine (I)

The product (118 mg) is obtained according to the method of stage 4 of Example 1, by using 500 mg of the previous derivative as a starting product and 571 mg of sodium nitrite in 4 mL of acetic acid leading to the nitroso intermediate which is reduced by 431 mg of lithium aluminium hydride (8 equivalents) in 4 mL of tetrahydrofurane with reflux.
Yield: 23%
¹H NMR (CDCl₃, 300 MHz) δ (ppm): 7.00-7.18 (m, 5H), 6.94 (m, 1H), 6.90 (m, 2H), 4.77 (s broad, 1H), 4.09 (m, 1H), 2.98 (m, 4H), 2.00 (m, 2H), 1.80 (m, 2H), 1.24-1.67 (m, 12H)
HPLC: 94%
MS: MH⁺ 366

Stage 7: methyl 5-bromo-4-[N-(4-cyclohexyloxy-phenyl)-N-(2-piperidin-1-yl-phenyl)-hydrazinocarbonylmethyl]-2-methoxy-benzoate The product is obtained according to the method of stage 3 of Example 6, by using 50 mg of the previous hydrazine and 46 mg of the acid of preparation 2 in the presence of 29 mg of EDCI and 20 mg of HOBt in 1.5 mL of dimethylformamide. With a purification by reversed phase chromatography of a fraction (conditions; C18 column, 21.2×150 mm, isocratic mode 45% acetonitrile/H₂O+0.05% TFA, flow rate: 15 mL/min, wavelengths: 220 and 254 nm) 57 mg of the expected product were able to be isolated as a TFA salt.
Estimated yield: 54%
HPLC: 92%
MS: MH⁺ 650/652

Stage 8: 5-bromo-4-[N-(4-cyclohexyloxy-phenyl)-N-(2-piperidin-1-yl-phenyl)-hydrazinocarbonylmethyl]-2-methoxy-benzoic acid hydrochloride (12)

The product (61 mg) is obtained as a hydrochloride according to the method of stage 6 of Example 2, by using as a substrate the product obtained in the previous stage.
Yield: 85%
MP: 145-180° C.
HPLC: 91%
MS: MH⁺ 636/638

Example 13

5-bromo-2-methoxy-4-[N-(4-phenoxy-phenyl)-N-(2-piperidin-1-yl-phenyl)-hydrazinocarbonyl-methyl]-benzoic acid hydrochloride (13)

Stage 1: (2-nitro-phenyl)-(4-phenoxy-phenyl)-amine

The product (2.03 g) is obtained according to the method of stage 1 of Example 4, by using 3.7 mL of 2-fluoronitrobenzene and 7.88 g of 4-phenoxyaniline in the presence of 6.36 g of potassium tert-butanolate in 34 mL of DMSO.
Yield: 18%
¹H NMR (CDCl₃, 300 MHz) δ (ppm): 9.44 (s broad, 1H), 8.20 (d, 1H), 7.37 (m, 3H), 7.25 (m, 2H), 7.05-7.18 (m, 6H), 6.76 (m, 1H)
HPLC: 80%
MS: MH⁺ 307

Stage 2: N-(4-phenoxy-phenyl)-benzene-1,2-diamine

The product (709 mg) is obtained by catalytic hydrogenation in the presence of 203 mg of 10% palladium on charcoal in 40 mL of ethanol.
Yield: 38%

¹H NMR (CDCl₃, 300 MHz) δ (ppm): 7.30 (m, 2H), 6.90-7.12 (m, 7H), 6.70-6.85 (m, 4H)
HPLC: 100%
MS: MH⁺ 277

Stage 3: (4-phenoxy-phenyl)-(2-piperidin-1-yl-phenyl)-amine

The product (799 mg) is obtained according to the method of stage 3 of Example 4, by using 709 mg of the previous derivative as a starting product, 350 μL of dibromopentane and 1.07 mL of DIPEA in 10 mL of toluene.
Yield: 82%
¹H NMR (DMSO, 300 MHz) δ (ppm): 7.40 (d, 1H), 7.25 (m, 4H), 7.03 (m, 4H), 6.95 (m, 4H), 3.37 (m, 4H), 1.90 (m, 4H), 1.61 (m, 2H)
HPLC: 100%
MS: MH⁺ 345

Stage 4: N-(4-phenoxy-phenyl)-N-(2-piperidin-1-yl-phenyl)-hydrazine (m)

The product (185 mg) is obtained according to the method of stage 4 of Example 1, by using 400 mg of the previous derivative as a starting product and 420 mg of sodium nitrite in 3 mL of acetic acid leading to the nitroso intermediate which is reduced by 319 mg of lithium aluminium hydride (8 equivalents) in 3 mL of tetrahydrofurane with reflux.
Yield: 49%
¹H NMR (CDCl₃, 300 MHz) δ (ppm): 6.92-7.26 (m, 13H), 4.82 (s broad, 2H), 2.97 (m, 4H), 1.55-1.69 (2m, 6H)
HPLC: 97%
MS: MH⁺ 360

Stage 5: methyl 5-bromo-2-methoxy-4-[N-(4-phenoxy-phenyl)-N-(2-piperidin-1-yl-phenyl)-hydrazinocarbonyl-methyl]-benzoate The product (270 mg) is obtained according to the method of stage 3 of Example 6, by using 185 mg of the previous hydrazine and 172 mg of the acid of the preparation 2 in the presence of 108 mg of EDCI and 76 mg of HOBt in 3 mL of dimethylformamide.
Yield: 81%
¹H NMR (CDCl₃, 300 MHz) δ (ppm): 9.35 (s broad, 1H), 7.97 (d, 1H), 6.75-7.50 (bulk aromatic, 14H), 3.70-3.94 (3s, 8H), 2.68 (m, 4H), 1.46-1.59 (m, 6H)
HPLC: 77%
MS: MH⁺ 644/646

Stage 6: 5-bromo-2-methoxy-4-[N-(4-phenoxy-phenyl)-N-(2-piperidin-1-yl-phenyl)-hydrazinocarbonyl-methyl]-benzoic acid hydrochloride (13)

The product is obtained according to the method of stage 6 of Example 2, by using as a substrate the product obtained in the previous stage. With purification by reversed phase chromatography of a fraction (conditions: C18 column, 21.2×150 mm, isocratic mode 35% acetonitrile/H₂O+0.05% TFA, flow rate: 15 mL/min, wavelengths: 220 and 254 nm) followed by a treatment with a 1 N hydrochloric acid solution, the expected product was able to be isolated as a hydrochloride (89 mg).
Yield: 32%
MP: 232-235° C.

Elementary analysis calculated for C₃₃H₃₂BrN₃O₅.1HCl.1H₂O: C, 57.86; H, 5.15; N, 6.13. Found: C, 57.74; H, 5.01; N, 5.89.
HPLC: 97%
MS: MH⁺ 630/632

Example 14

5-bromo-4-{N-[4-(4-chloro-phenoxy)-phenyl]-N-(2-piperidin-1-yl-phenyl)-hydrazinocarbonylmethyl}-2-methoxy-benzoic acid hydrochloride (14)

Stage 1: [4-(4-chloro-phenoxy)-phenyl]-(2-nitro-phenyl)-amine

The product (609 mg) is obtained according to the method of stage 1 of Example 4, by using 840 μL of 2-fluoro-nitrobenzene and 2.1 g of 4-(chlorophenoxy)-aniline in the presence of 1.43 g of potassium tert-butanolate in 20 mL of DMSO.
Yield: 22%
¹H NMR (CDCl₃, 300 MHz) δ (ppm): 8.21 (d, 1H), 7.24-7.40 (m, 5H), 6.97-7.14 (m, 5H), 6.77 (t, 1H)
HPLC: 97%
MS: MH⁺ 341/343

Stage 2: N-[4-(4-chloro-phenoxy)-phenyl]-benzene-1,2-diamine

The product (524 mg) is obtained according to the method of stage 2 of Example 1, by using 609 mg of the previous derivative as a starting product and 2 g of tin chloride hydrate in 10 mL of ethanol.
Yield: 94%
¹H NMR (CDCl₃, 300 MHz) δ (ppm): 6.73-7.38 (bulk aromatic, 12H)
HPLC: 100%
MS: MH⁺ 311/313

Stage 3: [4-(4-Chloro-phenoxy)-phenyl]-(2-piperidin-1-yl-phenyl)-amine

The product (596 mg) is obtained according to the method of stage 3 of Example 4, by using 684 mg of the previous derivative as a starting product, 300 μL of dibromopentane and 920 μL of DIPEA in 15 mL of toluene.
Yield: 71%
¹H NMR (CDCl₃, 300 MHz) δ (ppm): 6.80-7.28 (bulk aromatic, 12H), 6.66 (s broad, 1H), 2.86 (m, 4H), 1.72 (m, 4H), 1.61 (m, 2H)
HPLC: 99%
MS: MH⁺ 379/381

Stage 4: N-[4-(4-chloro-phenoxy)-phenyl]-N-(2-piperidin-1-yl-phenyl)-hydrazine (n)

The product (80 mg) is obtained according to the method of stage 4 of Example 1, by using 300 mg of the previous derivative as a starting product and 317 mg of sodium nitrite in 3 mL of acetic acid leading to the nitroso intermediate which is reduced by 120 mg of lithium aluminium hydride (4 equivalents) in 5 mL of tetrahydrofurane.
Yield: 26%
¹H NMR (CDCl₃, 300 MHz) δ (ppm): 6.86-7.25 (bulk aromatic, 12H), 2.98 (m, 4H), 1.70 (m, 4H), 1.56 (m, 2H)
HPLC: 83%
MS: MH⁺ 394/396

Stage 5: methyl 5-bromo-4-{N-[4-(4-chloro-phenoxy)-phenyl]-N-(2-piperidin-1-yl-phenyl)-hydrazinocarbonyl-methyl}-2-methoxy-benzoate The product (86 mg) is obtained according to the method of stage 3 of Example 6, by using 80 mg of the previous hydrazine and 68 mg of the acid of preparation 2 in the presence of 43 mg of EDCI and 30 mg of HOBt in 3 mL of dimethylformamide.
Yield: 62%
$^1$H NMR (CDCl$_3$, 300 MHz) δ (ppm): 9.35 (s broad, 1H), 7.97 (d, 1H), 6.75-7.52 (bulk aromatic, 13H), 3.67-3.91 (3s, 8H), 2.68 (m, 4H), 1.42-1.59 (m, 6H)
HPLC: 94%
MS: MH$^+$ 678/680

Stage 6: 5-bromo-4-{N-[4-(4-chloro-phenoxy)-phenyl]-N-(2-piperidin-1-yl-phenyl)-hydrazino-carbonylmethyl}-2-methoxy-benzoic acid hydrochloride (14)

The product (52 mg) is obtained as a hydrochloride according to the method of stage 6 of Example 2, by using as a substrate the product obtained in the previous stage.
Yield: 62%
MP: 153.5-163.5° C.
HPLC: 95% MS: MH$^+$ 664/666

Example 15

4-{N-[4-(4-fluoro-phenoxy)-phenyl]-N-(2-methyl-6-piperidin-1-yl-phenyl)-hydrazinocarbonyl-methyl}-2-methoxy-benzoic acid hydrochloride (15)

Stage 1: [4-(4-fluoro-phenoxy)-phenyl]-(2-methyl-6-nitro-phenyl)-amine

The product (790 mg) is obtained according to the method of stage 1 of Example 4, by using 900 μL of 2-fluoro-3-methyl-nitrobenzene and 2.6 g of 4-(4-fluoro-phenoxy)-phenylamine obtained in stage 2 of Example 5 in the presence of 2.36 g of potassium tert-butanolate in 80 mL of DMSO.
Yield: 40%
$^1$H NMR (CDCl$_3$, 300 MHz) δ (ppm): 8.38 (s broad, 1H), 1.98 (d, 1H), 7.40 (d, 1H), 6.87-7.06 (bulk aromatic, 7H), 6.76 (d, 2H), 2.08 (s, 3H)
HPLC: 84%
MS: MH$^+$ 339

Stage 2: N$^2$-[4-(4-fluoro-phenoxy)-phenyl]-3-methyl-benzene-1,2-diamine

The product (1.58 g) is obtained by hydrogenation according to the method of stage 2 of Example 13.
Yield: 87%
$^1$H NMR (CDCl$_3$, 300 MHz) δ (ppm): 6.83-7.01 (bulk aromatic, 7H), 6.67 (d, 2H), 6.55 (d, 2H), 4.92 (s broad, 1H), 3.89 (s broad, 2H), 2.18 (s, 3H)
HPLC: 98%
MS: MH$^+$ 309

Stage 3: [4-(4-fluoro-phenoxy)-phenyl]-(2-methyl-6-piperidin-1-yl-phenyl)-amine

The product (1.16 g) is obtained according to the method of stage 3 of Example 4, by using 1.58 g of the previous derivative as a starting product, 700 μL of dibromopentane and 2.14 mL of DIPEA in 30 mL of toluene.
Yield: 60%
$^1$H NMR (CDCl$_3$, 300 MHz) δ (ppm): 6.84-7.01 (bulk aromatic, 9H), 6.70 (d, 2H), 6.18 (s broad, 1H), 2.74 (m, 4H), 2.13 (s, 3H), 1.58 (m, 6H)
HPLC: 98%
MS: MH$^+$ 377

Stage 4: N-[4-(4-fluoro-phenoxy)-phenyl]-N-(2-methyl-6-piperidin-1-yl-phenyl)-hydrazine (o)

The product (198 mg) is obtained according to the method of stage 4 of Example 1, by using 525 mg of the previous derivative as a starting product and 558 mg of sodium nitrite in 4 mL of acetic acid leading to the nitroso intermediate which is reduced by 208 mg of lithium aluminium hydride (4 equivalents) in 4 mL of tetrahydrofurane.
Yield: 36%
$^1$H NMR (CDCl$_3$, 300 MHz) δ (ppm): 6.83-7.18 (bulk aromatic, HH), 4.87 (s broad, 2H), 2.68 and 2.94 (4H, 2m), 2.12 (s, 3H), 1.50-1.64 (m, 6H)
HPLC: 76%
MS: MH$^+$ 392

Stage 5: methyl 4-{N-[4-(4-fluoro-phenoxy)-phenyl]-N-(2-methyl-6-piperidin-1-yl-phenyl)-hydrazinocarbonyl-methyl}-2-methoxy-benzoate The product (141 mg) is obtained according to the method of stage 3 of Example 6, by using 95 mg of the previous hydrazine and 60 mg of the acid of the preparation 1 in the presence of 51 mg of EDCI and 36 mg of HOBt in 1.5 mL of dimethylformamide.
Yield: 97%
$^1$H NMR (CDCl$_3$, 300 MHz) δ (ppm): 9.76 (s broad, 1H), 7.74 (d, 1H), 6.50-7.22 (bulk aromatic, 13H), 3.87 (s, 3H), 3.70 (m, 5H), 2.72 (m, 2H), 2.44 (s, 3H), 2.30 (m, 2H), 1.30-1.42 (2m, 6H)
HPLC: 97%
MS: MH$^+$ 598

Stage 6: 4-{N-[4-(4-fluoro-phenoxy)-phenyl]-N-(2-methyl-6-piperidin-1-yl-phenyl)-hydrazinocarbonyl-methyl}-2-methoxy-benzoic acid hydrochloride (15)

The product (131 mg) is obtained as a hydrochloride according to the method of stage 6 of Example 2, by using as a substrate the product obtained in the previous stage.
Yield: 90%
MP: 155-168° C.
HPLC: 100%
MS: MH$^+$ 584

Example 16

5-bromo-4-{N-[4-(4-fluoro-phenoxy)-phenyl]-N-(2-methyl-6-piperidin-1-yl-phenyl)-hydrazino-carbonylmethyl}-2-methoxy-benzoic acid hydrochloride (16)

Stage 1: methyl 5-bromo-4-{N-[4-(4-fluoro-phenoxy)-phenyl]-N-(2-methyl-6-piperidin-1-yl-phenyl)-hydrazino-carbonylmethyl}-2-methoxy-benzoate (16a)

The product (154 mg) is obtained according to the method of stage 3 of Example 6, by using 95 mg of the hydrazine of stage 4 of Example 15 and 81 mg of the acid of preparation 2 in the presence of 51 mg of EDCI and 36 mg of HOBt in 1.5 mL of dimethylformamide.
Yield: 94%
$^1$H NMR (CDCl$_3$, 300 MHz) δ (ppm): 9.86 (s broad, 1H), 7.98 (s, 1H), 6.84-7.23 (bulk aromatic, 10H), 6.57 (d, 2H), 3.87 (s, 3H), 3.76 (s, 2H), 3.71 (s, 3H), 2.80 (m, 2H), 2.44 (s, 5H), 1.37-1.48 (2m, 6H)
HPLC: 91%
MS: MH$^+$ 676/678

Stage 2: 5-bromo-4-{N-[4-(4-fluoro-phenoxy)-phenyl]-N-(2-methyl-6-piperidin-1-yl-phenyl)-hydrazinocarbonyl-methyl}-2-methoxy-benzoic acid hydrochloride (16)

The product (116 mg) is obtained as a hydrochloride according to the method of stage 6 of Example 2, by using as a substrate the product obtained in the previous stage.
Yield: 73%
MP: 155-168° C.
Elementary analysis calculated for C$_{34}$H$_{33}$BrFN$_3$O$_5$.1HCl.1.5H$_2$O: C, 56.25; H, 5.14; N, 5.79. Found: C, 56.31; H, 5.04; N, 5.61.
HPLC: 98%
MS: MH$^+$ 662/664

Example 17

4-[N-(4-benzyl-phenyl)-N-(2-piperidin-1-yl-phenyl)-hydrazinocarbonylmethyl]-5-bromo-2-methoxy-benzoic acid hydrochloride (17)

Stage 1: (4-benzyl-phenyl)-(2-nitro-phenyl)-amine

The product (621 mg) is obtained according to the method of stage 1 of Example 4, by using 958 μL of 2-fluoronitrobenzene and 2 g of 4-benzylaniline in the presence of 1.63 of potassium tert-butanolate in 30 mL of DMSO.
Yield: 22%
$^1$H NMR (CDCl$_3$, 300 MHz) δ (ppm): 9.46 (s broad, 1H), 8.19 (d, 1H), 7.71 (d, 1H), 7.44 (m, 1H), 7.10-7.40 (bulk aromatic, 9H), 6.74 (m, 1H), 4.01 (s, 2H)
HPLC: 78%
MS: [M+Na]$^+$ 327

Stage 2: N-(4-benzyl-phenyl)-benzene-1,2-diamine

The product (291 mg) is obtained by hydrogenation according to the method of stage 2 of Example 13.
Yield: 52%
HPLC: 100%
MS: MH$^+$ 275

Stage 3: (4-benzyl-phenyl)-(2-piperidin-1-yl-phenyl)-amine

The product (213 mg) is obtained according to the method of stage 3 of Example 4, by using 291 mg of the previous derivative as a starting product, 144 μL of dibromopentane and 444 μL of DIPEA in 4 mL of toluene.
Yield: 59%
$^1$H NMR (CDCl$_3$, 300 MHz) δ (ppm): 6.79-7.32 (bulk aromatic, 13H), 6.63 (s broad, 1H), 3.94 (s, 2H), 2.83 (m, 4H), 1.70 (m, 4H), 1.58 (m, 2H)
HPLC: 96%
MS: MH$^+$ 343

Stage 4: N-(4-benzyl-phenyl)-N-(2-piperidin-1-yl-phenyl)-hydrazine (p)

The product (60 mg) is obtained according to the method of stage 4 of Example 1, by using 213 mg of the previous derivative as a starting product and 249 mg of sodium nitrite in 3 mL of acetic acid leading to the nitroso intermediate which is reduced by 189 mg of lithium aluminium hydride (8 equivalents) in 3 mL of tetrahydrofurane.
Yield: 27%
$^1$H NMR (CDCl$_3$, 300 MHz) δ (ppm): 6.92-7.31 (bulk aromatic, 13H), 4.75 (s broad, 1H), 3.91 (s, 2H), 2.96 (m, 4H), 1.66 (m, 4H), 1.54 (m, 2H)
HPLC: 100%
MS: MH$^+$ 358

Stage 5: methyl 4-[N-(4-benzyl-phenyl)-N-(2-piperidin-1-yl-phenyl)-hydrazinocarbonylmethyl]-5-bromo-2-methoxy-benzoate The product (64 mg) is obtained according to the method of stage 3 of Example 6, by using 60 mg of the previous hydrazine and 56 mg of the acid of preparation 2 in the presence of 35 mg of EDCI and 25 mg of HOBt in 1 mL of dimethylformamide.
Yield: 59%
$^1$H NMR (CDCl$_3$, 300 MHz) δ (ppm): 9.33 (s broad, 1H), 7.98 (d, 1H), 6.71-7.51 (bulk aromatic, 14H), 3.95 (s, 6H), 3.70 and 3.76 (2s, 4H), 2.74 (m, 4H), 1.28-1.60 (m, 6H)
HPLC: 90%
MS: MH$^+$ 642/644

Stage 6: 4-[N-(4-benzyl-phenyl)-N-(2-piperidin-1-yl-phenyl)-hydrazinocarbonylmethyl]-5-bromo-2-methoxy-benzoic acid hydrochloride (17)

The product (58 mg) is obtained as a hydrochloride according to the method of stage 6 of Example 2, by using as a substrate the product obtained in the previous stage.
Yield: 88%
MP: 137.5-162° C.
HPLC: 97%
MS: MH$^+$ 628/630

Example 18

4-[N-(4-bromo-phenyl)-[N-(2-piperidin-1-yl-phenyl)-hydrazinocarbonylmethyl]-5-chloro-2-methoxy-benzoic acid hydrochloride (18)

Stage 1: N-(4-bromo-phenyl)-N-(2-piperidin-1-yl-phenyl)-hydrazine (q)

The product (370 mg) is obtained according to the method of stage 4 of Example 1, by using 500 mg of the derivative obtained in stage 3 of Example 11 as a starting product and 604 mg of sodium nitrite in 3 mL of acetic acid leading to the nitroso intermediate which is reduced by 458 mg of lithium aluminium hydride (8 equivalents) in 3 mL of tetrahydrofurane.
Yield: 71%
$^1$H NMR (CDCl$_3$, 300 MHz) δ (ppm): 6.98-7.25 (bulk aromatic, 8H), 4.77 (s broad, 2H), 2.92 (m, 4H), 1.66 (m, 4H), 1.55 (m, 2H)
HPLC: 88%
MS: MH$^+$ 346/348

Stage 2: methyl 4-[N-(4-bromo-phenyl)-N-(2-piperidin-1-yl-phenyl)-hydrazinocarbonylmethyl]-5-chloro-2-methoxy-benzoate The product (64 mg) is obtained according to the method of stage 3 of Example 6, by using 370 mg of the previous hydrazine and 304 mg of the acid of preparation 3 in the presence of 225 mg of EDCI and 159 mg of HOBt in 5 mL of dimethylformamide.
Yield: 89%
$^1$H NMR (CDCl$_3$, 300 MHz) δ (ppm): 9.34 (s broad, 1H), 7.78 (d, 1H), 6.63-7.49 (bulk aromatic, 9H), 3.87 (2s, 6H), 3.70 (s, 2H), 2.75 (m, 4H), 1.28 et 1.60 (2m, 6H)
HPLC: 96%
MS. MH$^+$ 586/588

Stage 3: 4-[N-(4-bromo-phenyl)-N-(2-piperidin-1-yl-phenyl)-hydrazinocarbonylmethyl]-5-chloro-2-methoxy-benzoic acid hydrochloride (18)

The product (39 mg) is obtained as a hydrochloride according to the method of stage 6 of Example 2, by using as a substrate the product obtained in the previous stage.
Yield: 75%
MP: 177.2-189° C.
HPLC: 95%
MS: MH$^+$ 572/574

Example 19

4-[N-(3'-acetyl-biphenyl-4-yl)-N-(2-piperidin-1-yl-phenyl)-hydrazinocarbonylmethyl]-5-chloro-2-methoxy-benzoic acid hydrochloride (19)

Stage 1: methyl 4-[N-(3'-Acetyl-biphenyl-4-yl)-N-(2-piperidin-1-yl-phenyl)-hydrazinocarbonylmethyl]-5-chloro-2-methoxy-benzoate To a solution of 200 mg of the brominated derivative obtained in stage 2 of Example 18 in 2 mL of a 50:50 methanol/toluene mixture are successively added 84 mg of 3-acetylphenylboronic acid (1.5 equivalents), 20 mg of palladium tetrakis (0.05 equivalents) and 85 μL of 1 molar solution of sodium carbonate. The whole is refluxed for 3 hrs. The reaction crude product taken up in water is extracted with ethyl acetate several time, the collected organic phases are washed with a 1 molar solution of soda, and then dried on magnesium sulfate, filtered and evaporated under reduced pressure. The obtained residue is purified by silica gel chromatography (petroleum ether/ethyl acetate: 90/10 and then 80/20 right up to 50/50) leading to 110 mg of the expected product.
Yield: 51%
$^1$H NMR (CDCl$_3$, 300 MHz) δ (ppm): 9.35 (s, 1H), 8.04 (d, 1H), 7.74 (m, 3H), 6.94-7.62 (bulk aromatic, 8H), 6.80 (m, 2H), 2.79-3.62 (3s, 8H), 2.56 (m, 4H), 2.05 (s, 3H), 1.18-1.53 (m, 6H)
HPLC: 92%
MS: MH$^+$ 626/628

Stage 2: 4-[N-(3'-acetyl-biphenyl-4-yl)-N-(2-piperidin-1-yl-phenyl)-hydrazinocarbonylmethyl]-5-chloro-2-methoxy-benzoic acid hydrochloride (19)

The product (69 mg) is obtained as a hydrochloride according to the method of stage 6 of Example 2, by using as a substrate the product obtained in the previous stage.

Yield: 66%
MP: 140.2-165.3° C.
HPLC: 91%
MS: MH$^+$ 612/614

Example 20

4-(N-(4'-acetyl-biphenyl-4-yl)-N-(2-piperidin-1-yl-phenyl)-hydrazinocarbonylmethyl)-5-chloro-2-methoxy-benzoic acid hydrochloride (20)

Stage 1: methyl 4-[N-(4'-Acetyl-biphenyl-4-yl)-N-(2-piperidin-1-yl-phenyl)-hydrazinocarbonylmethyl]-5-chloro-2-methoxy-benzoate The product (167 mg) is obtained according to the method of stage 1 of Example 19, by using as a substrate the product obtained in stage 2 of Example 18 and as a co-substrate 4-acetylphenylboronic acid.
Yield: 78%
$^1$H NMR (CDCl$_3$, 300 MHz) δ (ppm): 9.35 (s, 1H), 6.70-7.91 (bulk aromatic, 14H), 3.61-3.78 (3s, 8H), 2.60 (m, 4H), 2.28 (s, 3H), 1.20-1.51 (m, 6H)
HPLC: 87%
MS: MH$^+$ 626/628

Stage 2: 4-[N-(4'-acetyl-biphenyl-4-yl)-N-(2-piperidin-1-yl-phenyl)-hydrazinocarbonylmethyl]-5-chloro-2-methoxy-benzoic acid hydrochloride (20)

The product (82 mg) is obtained as a hydrochloride according to the method of stage 6 of Example 2, by using as a substrate the product obtained in the previous stage.
Yield: 47%
MP: 165.3-190.1° C.
HPLC: 100%
MS: MH$^+$ 612/614

Example 21

5-bromo-2-methoxy-4-[N-(3-phenoxy-phenyl)-N-(2-piperidin-1-yl-phenyl)-hydrazinocarbonylmethyl]-benzoic acid hydrochloride (21)

Stage 1: (2-nitro-phenyl)-(3-phenoxy-phenyl)-amine

The product (2.08 g) is obtained according to the method of stage 1 of Example 4, by using 1.23 mL of 2-fluoronitrobenzene and 3.3 g of 3-phenoxyaniline in the presence of 2.13 g of potassium tert-butanolate in 10 mL of DMSO.
Yield: 57%
$^1$H NMR (CDCl$_3$, 300 MHz) δ (ppm): 9.38 (s broad, 1H), 8.12 (d, 1H), 7.63 (d, 1H), 6.70-7.43 (m, 11H)
HPLC: 79%
MS: MH$^+$ 307

Stage 2: N-(3-phenoxy-phenyl)-benzene-1,2-diamine

The product (1.88 g) is obtained by catalytic hydrogenation in the presence of 210 mg of 10% palladium on charcoal in 40 mL of an ethyl acetate/ethanol (1:1) mixture.
Yield: quantitative
HPLC: 91%
MS: MH$^+$ 277

Stage 3: (3-Phenoxy-phenyl)-(2-piperidin-1-yl-phenyl)-amine

The product (1.22 g) is obtained according to the method of stage 3 of Example 4, by using 1.88 g of the previous derivative as a starting product, 925 µL of dibromopentane and 2.84 mL of DIPEA in 40 mL of toluene.
Yield: 52%
$^1$H NMR (CDCl$_3$, 300 MHz) δ (ppm): 6.83-7.19 (bulk aromatic, 11H), 6.72 (s, 1H), 6.53 (dd, 1H), 2.81 (m, 4H), 1.50-1.74 (m, 6H)
HPLC: 100%
MS: MH$^+$ 345

Stage 4: N-(3-phenoxy-phenyl)-N-(2-piperidin-1-yl-phenyl)-hydrazine (r)

The product (99 mg) is obtained according to the method of stage 4 of Example 1, by using 400 mg of the previous derivative as a starting product and 465 mg of sodium nitrite in 3 mL of acetic acid leading to the nitroso intermediate which is reduced by 159 mg of lithium aluminium hydride (4 equivalents) in 4 mL of tetrahydrofurane with reflux.
Yield: 24% $^1$H NMR (CDCl$_3$, 300 MHz) δ (ppm): 6.70-7.25 (bulk aromatic, 12H), 6.28 (dd, 1H), 4.68 (s broad, 2H), 2.85 (m, 4H), 1.46-1.63 (m, 6H)
HPLC: 76%
MS: MH$^+$ 360

Stage 5: methyl 5-bromo-2-methoxy-4-[N-(3-phenoxy-phenyl)-N-(2-piperidin-1-yl-phenyl)-hydrazinocarbonyl-methyl]-benzoate The product (168 mg) is obtained according to the method of stage 3 of Example 6, by using 99 mg of the previous hydrazine and 92 mg of the acid of preparation 2 in the presence of 58 mg of EDCI and 41 mg of HOBt in 1 mL of dimethylformamide.
Yield: 95%
$^1$H NMR (CDCl$_3$, 300 MHz) δ (ppm): 9.35 and 9.40 (2 s broad, 1H), 7.98 (2s, 1H), 6.41-7.40 (bulk aromatic, 14H), 3.70-3.95 (3s, 8H), 2.68 (m, 4H), 1.46-1.59 (m, 6H)
HPLC: 96%
MS: MH$^+$ 644/646

Stage 6: 5-bromo-2-methoxy-4-[N-(3-phenoxy-phenyl)-N-(2-piperidin-1-yl-phenyl)-hydrazinocarbonyl-methyl]-benzoic acid hydrochloride (21)

The product (124 mg) is obtained as a hydrochloride according to the method of stage 6 of Example 2, by using as a substrate the product obtained in the previous stage.
Yield: 71%
MP: 142-159° C.
Elementary analysis calculated for C$_{33}$H$_{32}$BrN$_3$O$_5$.0.75HCl: C, 60.25; H, 5.02; N, 6.39. Found: C, 59.98; H, 5.11; N, 6.27.
HPLC: 96%
MS: MH$^+$ 630/632

Example 22

5-bromo-2-methoxy-4-[N-(4-phenylsulfanyl-phenyl)-N-(2-piperidin-1-yl-phenyl)-hydrazinocarbonyl-methyl]-benzoic acid hydrochloride (22)

Stage 1: 4-phenylsulfanyl-phenylamine

To a solution of 5 g of 4-nitrophenyl sulfure in 100 mL of an ethanol/ethyl acetate mixture (1:1) are added 500 mg of 10% palladium on charcoal. The whole is placed under a hydrogen atmosphere (P=10 bars) for one night.
The whole is filtered on celite, rinsed and the filtrate is concentrated under reduced pressure leading to 3.57 g of the expected product.
Yield: 82%
$^1$H NMR (CDCl$_3$, 300 MHz) δ (ppm): 7.10-7.35 (bulk aromatic, 7H), 6.69 (d, 2H), 3.98 (s broad, 2H)
HPLC: 86%
MS: MH$^+$ 202

Stage 2: (2-nitro-phenyl)-(4-phenylsulfanyl-phenyl)-amine

The product (2.50 g) is obtained according to the method of stage 1 of Example 4, by using 1.25 mL of 2-fluoro-nitrobenzene and 3.57 g of the obtained product of the previous stage in the presence of 2.12 g of potassium tert-butanolate in 10 mL of DMSO.
Yield: 66%
$^1$H NMR (CDCl$_3$, 300 MHz) δ (ppm): 9.48 (s broad, 1H), 8.22 (d, 1H), 7.11-7.42 (bulk aromatic, 11H), 6.83 (m, 1H),
HPLC: 96%
MS: [M+Na]$^+$ 345

Stage 3: N-[4-phenylsulfanyl-phenyl]-benzene-1,2-diamine

The product (2 g) is obtained by catalytic hydrogenation by using 2.50 g of the derivative obtained previously in the presence of 250 mg of 10% palladium on charcoal in 30 mL of an ethanol/ethyl acetate mixture (1:1).
Yield: 88%
HPLC: 92%
MS: MH$^+$ 293

Stage 4: (4-phenylsulfanyl-phenyl)-(2-piperidin-1-yl-phenyl)-amine

The product (1.37 g) is obtained according the method of stage 3 of Example 4, by using 2 g of the previous derivative as starting product, 932 µL of dibromopentane and 2.86 mL of DIPEA in 40 mL of toluene.
Yield: 55%
$^1$H NMR (CDCl$_3$, 300 MHz) δ (ppm): 6.87-7.41 (bulk aromatic, 13H), 6.78 (s broad, 1H), 2.84 (m, 4H), 1.74 (m, 4H), 1.60 (m, 2H)
HPLC: 98%
MS: MH$^+$ 361

Stage 5: N-(4-phenylsulfanyl-phenyl)-N-(2-piperidin-1-yl-phenyl)-hydrazine (s)

The product (300 mg) is obtained according to the method of stage 4 of Example 1, by using 800 mg of the previous derivative as starting product and 888 mg of sodium nitrite in 5 mL of acetic acid leading to the nitroso intermediate which is reduced by 316 mg of lithium aluminium hydride (4 equivalents) in 5 mL of tetrahydrofurane.
Yield: 36%
$^1$H NMR (CDCl$_3$, 300 MHz) δ (ppm): 6.92-7.26 (bulk aromatic, 13H), 4.71 (s broad, 2H), 2.84 (m, 4H), 1.58 (m, 4H), 1.47 (m, 2H)
HPLC: 90%
MS: MH$^+$ 376

Stage 6: methyl 5-bromo-2-methoxy-4-[N-(4-phenyl-sulfanyl-phenyl)-N-(2-piperidin-1-yl-phenyl)-hydrazino-carbonylmethyl]-benzoate The product (340 mg) is obtained according to the method of stage 3 of Example 6, by using 300 mg of the previous hydrazine as substrate and 266 mg of the acid of preparation 2 as a co-substrate in the presence of 168 mg of EDCI and 118 mg of HOBt in 2.5 mL of dimethylformamide.
Yield: 640
$^1$H NMR (CDCl$_3$, 300 MHz) δ (ppm): 9.34 (s broad, 1H), 7.99 (2s, 1H), 6.79-7.53 (bulk aromatic, 14H), 3.70-3.92 (3s, 8H), 2.71 (m, 4H), 1.48 and 1.60 (2m, 6H)
HPLC: 91%
MS: MH$^+$ 660/662

Stage 7: 5-bromo-2-methoxy-4-[N-(4-phenylsulfanyl-phenyl)-N-(2-piperidin-1-yl-phenyl)-hydrazinocarbonyl-methyl]-benzoic acid hydrochloride (22)

The product (108 mg) is obtained as a hydrochloride according to the method of stage 6 of Example 2, by using as a substrate the product obtained at the previous stage.
Yield: 83%
MP: 158-166° C.
Elementary analysis calculated for C$_{33}$H$_{32}$BrN$_3$O$_4$S.1HCl.1H$_2$O: C, 56.54; H, 5.03; N, 5.99. Found: C, 56.59; H, 4.96; N, 5.84.
HPLC: 95%
MS: MH$^+$ 646/648

Examples 23 AND 24

4-[N-(4-benzenesulfonyl-phenyl)-N-(2-piperidin-1-yl-phenyl)-hydrazinocarbonylmethyl]-5-bromo-2-methoxy-benzoic acid hydrochloride (23) and 4-[N-(4-benzenesulfinyl-phenyl)-N-(2-piperidin-1-yl-phenyl)-hydrazinocarbonylmethyl]-5-bromo-2-methoxy-benzoic acid hydrochloride (24)

Stage 1: methyl 4-[N-(4-benzenesulfonyl-phenyl)-N-(2-piperidin-1-yl-phenyl)-hydrazinocarbonylmethyl]-5-bromo-2-methoxy-benzoate and methyl 4-[N-(4-benzene-sulfinyl-phenyl)-N-(2-piperidin-1-yl-phenyl)-hydrazino-carbonylmethyl]-5-bromo-2-methoxy-benzoate To a solution of 100 mg of the obtained product of stage 6 of Example 22 in 3 mL of dichloromethane is added an excess of metachloroperbenzoic acid (2 equivalents and 2 other equivalents over time) until total disappearance of the starting product (tracked by TLC). The reaction crude production is filtered, the filtrate is washed with a saturated solution of sodium sulfite and then sodium bicarbonate. The collected organic phases are dried on magnesium sulfate and then evaporated under reduced pressure leading to a mixture which is purified by silica gel chromatography (petroleum ether/ethyl acetate 60:40). 35 mg of each of the esters are obtained—sulfonyl and sulfinyl forms respectively—.
Yield (sulfonyl): 33%
HPLC: 83%
MS: MH$^+$ 692/694
Yield (sulfynyl): 34%
HPLC: 83%
MS: MH$^+$ 676/778

Stage 2: 4-[N-(4-benzenesulfonyl-phenyl)-N-(2-piperidin-1-yl-phenyl)-hydrazinocarbonylmethyl]-5-bromo-2-methoxy-benzoic acid hydrochloride (23)

The product (20 mg) is obtained as a hydrochloride according to the method of stage 6 of Example 2, by using as a substrate the sulfonyl derivative obtained in the previous stage.
Yield: 55%
Elementary analysis calculated for C$_{33}$H$_{32}$BrN$_3$O$_6$S.0.75HCl: C, 56.15; H, 4.68; N, 5.95. Found: C, 56.09; H, 4.65; N, 5.67.
HPLC: 84%
MS: MH$^+$ 678/680

Stage 2: 4-[N-(4-benzenesulfinyl-phenyl)-N-(2-piperidin-1-yl-phenyl)-hydrazinocarbonylmethyl]-5-bromo-2-methoxy-benzoic acid hydrochloride (24)

The product (23 mg) is obtained as hydrochloride according to the method of stage 6 of Example 2, by using as a substrate the sulfinyl obtained in the previous stage.
Yield: 63%
Elementary analysis calculated for C$_{33}$H$_2$BrN$_3$O$_5$S.1HCl.1.5H$_2$O: C, 54.59; H, 5.00; N, 5.79. Found: C, 54.56; H, 4.91; N, 5.54.
HPLC: 85%
MS: MH$^+$ 662/664

Example 25

2-methoxy-4-{(E)-2-[N-(4-methoxy-phenyl)-N-(2-methyl-6-piperidin-1-yl-phenyl)-hydrazinocarbonyl]-vinyl}-benzoic acid hydrochloride (25)

Stage 1: methyl 2-methoxy-4-{(E)-2-[N-(4-methoxy-phenyl)-N-(2-methyl-6-piperidin-1-yl-phenyl)-hydrazino-carbonyl]-vinyl}-benzoate The product (200 mg) is obtained according to the method of stage 3 of Example 6, by using 150 mg of the hydrazine of Example 7 as a substrate and 125 mg of the acid of preparation 4 as co-substrate in the presence of 102 mg of EDCI and 72 mg of HOBt in 1.5 mL of dimethylformamide.
Yield: 78%
$^1$H NMR (CDCl$_3$, 300 MHz) δ (ppm): 10.47 and 10.10 (2s broad, 1H), 7.95 (m, 2H), 7.20-7.48 (m, 6H), 6.65-7.10 (m, 4H), 4.11 (2s, 6H), 3.98 (s, 3H), 2.91 and 3.11 (m, 3H), 2.61 (m, 4H), 1.85 (m, 6H)
HPLC: 98%
MS: MH$^+$ 530

Stage 2: 2-methoxy-4-{(E)-2-[N-(4-methoxy-phenyl)-N-(2-methyl-6-piperidin-1-yl-phenyl)-hydrazinocarbonyl]-vinyl}-benzoic acid hydrochloride (25)

The product (149 mg) is obtained as a hydrochloride according to the method of stage 6 of Example 2, by using as a substrate the product obtained in the previous stage.
Yield: 71%
Elementary analysis calculated for C$_{30}$H$_{33}$N$_3$O$_5$.1HCl.1.5H$_2$O: C, 62.22; H, 6.44; N, 7.26. Found: C, 62.45; H, 6.34; N, 7.12.
HPLC: 94%
MS: MH$^+$ 516

Example 26

5-bromo-2-methoxy-4-{(E)-2-[N-(4-methoxy-phenyl)-N-(2-methyl-6-piperidin-1-yl-phenyl)-hydrazino-carbonyl]-vinyl}-benzoic acid hydrochloric (26)

Stage 1: methyl 5-bromo-2-methoxy-4-{(E)-2-[N-(4-methoxy-phenyl)-N-(2-methyl-6-piperidin-1-yl-phenyl)-hydrazinocarbonyl]-vinyl}-benzoate The product (234 mg) is obtained according the method of stage 3 of Example 6, by using 120 mg of hydrazine of Example 7 as a substrate and 134 mg of the acid of preparation 5 as a co-substrate in the presence of 81 mg of EDCI and 57 mg of HOBt in 2 mL of dimethylformamide.
Yield: quantitative
$^1$H NMR (CDCl$_3$, 300 MHz) δ (ppm): 10.37 and 9.95 (2s broad, 1H), 8.02 (m, 2H), 7.00-7.29 (m, 5H), 6.43-6.88 (m, 4H), 3.95 (3s, 9H), 2.70 and 2.90 (m, 3H), 2.40 (m, 4H), 1.60 (m, 6H)
HPLC: 870
MS: MH$^+$ 608/610

Stage 2: 5-bromo-2-methoxy-4-{(E)-2-[N-(4-methoxy-phenyl)-N-(2-methyl-6-piperidin-1-yl-phenyl)-hydrazinocarbonyl]-vinyl}-benzoic acid hydrochloride (26)

The product (217 mg) is obtained as a hydrochloride according to the method of stage 6 of Example 2, by using as a substrate the product obtained in the previous stage.
Yield: 86%
MP: 192-206° C.
Elementary analysis calculated for C$_{30}$H$_{32}$BrN$_3$O$_5$.1HCl.1H$_2$O: C, 55.52; H, 5.44; N, 6.47. Found: C, 55.43; H, 5.51; N, 6.37.
HPLC: 91%
MS: MH$^+$ 594/596

Example 27

4-[N-(4-benzyl-phenyl)-[N-(2-methyl-6-piperidin-1-yl-phenyl)-hydrazinocarbonylmethyl]-5-bromo-2-methoxy-benzoic acid hydrochloride (27)

Stage 1: (4-benzyl-phenyl)-(2-methyl-6-nitro-phenyl)-amine

The product (1.01 g) is obtained according to the method of stage 1 of Example 4, by using 1.13 g of 2-fluoro-3-methyl-nitrobenzene and 2 g of 4-benzyl-aniline in the presence of 1.31 g of potassium tert-butanolate in 30 mL of DMSO.
Estimated yield: 35%
$^1$H NMR (CDCl$_3$, 300 MHz) δ (ppm): 8.32 (s broad, 1H), 7.96 (d, 2H), 6.68-7.51 (bulk aromatic, 10H), 3.93 (s, 2H), 2.06 (s, 3H)
HPLC: 79%
MS: MH$^+$ 319

Stage 2: N$^2$-(4-benzyl-phenyl)-3-methyl-benzene-1,2-diamine

The product (530 mg) is obtained by hydrogenation according to the method of stage 2 of Example 13.
Yield: 58%
$^1$H NMR (CDCl$_3$, 300 MHz) δ (ppm): 6.99-7.32 (bulk aromatic, 8H), 6.68 (d, 2H), 6.52 (d, 2H), 3.89 (s, 2H), 2.18 (s, 3H)

Stage 3: (4-benzyl-phenyl)-(2-methyl-6-piperidin-1-yl-phenyl)-amine

The product (460 mg) is obtained according the method of stage 3 of Example 4, by using 525 mg of the previous derivative as a starting product, 247 μL of dibromopentane and 760 μL of DIPEA in 10 mL of toluene.
Yield: 710%
$^1$H NMR (CDCl$_3$, 300 MHz) δ (ppm): 6.92-7.31 (bulk aromatic, 10H), 6.62 (d, 2H), 6.17 (s broad, 1H), 3.90 (s, 2H), 2.72 (m, 4H), 2.10 (s, 3H), 1.56 (m, 6H)
HPLC: 98%
MS: MH$^+$ 357

Stage 4: N-(4-benzyl-phenyl)-N-(2-methyl-6-piperidin-1-yl-phenyl)-hydrazine (t)

The product (102 mg) is obtained according the method of stage 4 of Example 1, by using 450 mg of the previous derivative as a starting product and 505 mg of sodium nitrite in 3 mL of acetic acid leading to the nitroso intermediate which is reduced by 192 mg of lithium aluminium hydride (4 equivalents) in 5 mL of tetrahydrofurane.
Estimated yield: 22%
$^1$H NMR (CDCl$_3$, 300 MHz) δ (ppm): 7.12-7.29 (bulk aromatic, 6H), 6.97 (dd, 4H), 6.75 (d, 2H), 3.88 (s, 2H), 2.80 (m, 4H), 2.08 (s, 3H), 1.52 (m, 6H)
HPLC: 64%
MS: MH$^+$ 372

Stage 5: methyl 4-[N-(4-benzyl-phenyl)-N-(2-methyl-6-piperidin-1-yl-phenyl)-hydrazinocarbonylmethyl]-5-bromo-2-methoxy-benzoate The product (91 mg) is obtained according to the method of stage 3 of Example 6, by using 101 mg of the previous hydrazine and 91 mg of the acid of preparation 2 in the presence of 58 mg of EDCI and 41 mg of HOBt in 4 mL of dimethylformamide.
Yield: 51%
$^1$H NMR (CDCl$_3$, 300 MHz) δ (ppm): 9.97 and 9.79 (s broad, 1H), 7.97 (s, 1H), 6.75-7.27 (bulk aromatic, 11H), 6.51 (d, 2H), 3.87 (s, 6H), 3.72 (s, 4H), 2.74 (m, 2H), 2.37 (s, 3H), 2.36 (m, 2H), 1.40 (m, 6H)
HPLC: 96%
MS: MH$^+$ 656/658

Stage 6: 4-[N-(4-benzyl-phenyl)-N-(2-methyl-6-piperidin-1-yl-phenyl)-hydrazinocarbonylmethyl]-5-bromo-2-methoxy-benzoic acid hydrochloride (27)

The product (74 mg) is obtained as a hydrochloride according to the method of stage 6 of Example 2, by using as a substrate the product obtained in the previous stage.
Yield: 84%
MP: 173-187° C.
Elementary analysis calculated for C$_{35}$H$_{36}$BrN$_3$O$_4$.1HCl.1H$_2$O: C, 60.31; H, 5.64; N, 6.03. Found: C, 60.36; H, 5.62; N, 5.99.
HPLC: 98%
MS: MH$^+$ 642/644

Example 28

5-bromo-2-methoxy-4-[N-(4'-methoxy-biphenyl-4-yl)-N-(2-methyl-6-piperidin-1-yl-phenyl)-hydrazinocarbonylmethyl]-benzoic acid hydrochloride (28)

Stage 1: (4-bromo-phenyl)-(2-methyl-6-nitro-phenyl)-amine

The product (2.44 g) is obtained according to the method of stage 1 of Example 4, by using 1.8 g of 2-fluoro-3-methyl-nitrobenzene and 3 g of 4-bromo-aniline in the presence of 2.09 g of potassium tert-butanolate in 20 mL of DMSO.

Yield: 68%
$^1$H NMR (CDCl$_3$, 300 MHz) δ (ppm): 8.15 (s broad, 1H), 7.96 (d, 1H), 7.07-7.51 (bulk aromatic, 4H), 6.61 (d, 2H), 2.09 (s, 3H)
HPLC: 90%
MS: MH$^+$ 307/309

Stage 2: N$^2$-(4-bromo-phenyl)-3-methyl-benzene-1,2-diamine

The product (2.2 g) is obtained according to the method of stage 2 of Example 1, by using 2.44 g of the previous derivative as a starting product and 9 g of tin chloride hydrate in 30 mL of ethanol.

Yield: quantitative
$^1$H NMR (CDCl$_3$, 300 MHz) δ (ppm): 7.22 (s, 1H), 7.02 (t, 1H), 6.45 (m, 3H), 6.43 (d, 2H), 4.98 (s broad, 1H), 2.14 (s, 3H)
HPLC: 99%
MS: MH$^+$ 277/279

Stage 3: (4-bromo-phenyl)-(2-methyl-6-piperidin-1-yl-phenyl)-amine

The product (2 g) is obtained according to the method of stage 3 of Example 4, by using 2.2 g of the previous derivative as a starting product, 1.08 mL of dibromopentane and 3.3 mL of DIPEA in 40 mL of toluene.

Yield: 73%
$^1$H NMR (CDCl$_3$, 300 MHz) δ (ppm): 7.26 (m, 2H), 7.03 (t, 1H), 6.94 (d, 2H), 6.56 (d, 2H), 6.14 (s broad, 1H), 2.70 (m, 4H), 2.10 (s, 3H), 1.55 (m, 6H)
HPLC: 99%
MS: MH$^+$ 345/347

Stage 4: (4'-methoxy-biphenyl-4-yl)-(2-methyl-6-piperidin-1-yl-phenyl)-amine The product (248 mg) is obtained according to the method of stage 4 of Example 11, by using 300 mg of the previous derivative as a starting product, 198 mg of phenylboronic acid, 50 mg of palladium tetrakis, 110 mg of lithium chloride in the presence of 2.17 mL of a 1 M calcium carbonate solution in 6 mL of a methanol/toluene mixture (1:1).

Yield: 76%
$^1$H NMR (CDCl$_3$, 300 MHz) δ (ppm): 7.48 (d, 2H), 7.39 (d, 2H), 6.92-7.03 (m, 5H), 6.74 (d, 2H), 6.24 (s broad, 1H), 3.84 (s, 3H), 2.74 (m, 4H), 2.16 (s, 3H), 1.56 (m, 6H)
HPLC: 81%
MS: MH$^+$ 373

Stage 5: N-(4'-methoxy-biphenyl-4-yl)-N-(2-methyl-6-piperidin-1-yl-phenyl)-hydrazine (u)

The product (92 mg) is obtained according to the method of stage 4 of Example 1, by using 247 mg of the previous derivative as a starting product and 265 mg of sodium nitrite in 3 mL of acetic acid leading to the nitroso intermediate which is reduced with 101 mg of lithium aluminium hydride (4 equivalents) in 5 mL of tetrahydrofurane with reflux.

Yield: 35%
$^1$H NMR (CDCl$_3$, 300 MHz) δ (ppm): 7.48 (d, 2H), 7.38 (d, 2H), 7.17 (t, 1H), 6.86-7.03 (m, 6H), 4.90 (s broad, 2H), 3.83 (s, 3H), 2.95 (m, 2H), 2.69 (m, 2H), 2.11 (s, 3H), 1.51-1.66 (m, 6H)
HPLC: 95%
MS: MH$^+$ 388

Stage 6: methyl 5-bromo-2-methoxy-4-[N-(4'-methoxy-biphenyl-4-yl)-N-(2-methyl-6-piperidin-1-yl-phenyl)-hydrazinocarbonylmethyl]-benzoate The product (24 mg) is obtained according to the method of stage 3 of Example 6, by using 92 mg of the previous hydrazine and 79 mg of the acid of preparation 2 in the presence of 50 mg of EDCI and 35 mg of HOBt in 2.5 mL of dimethylformamide.

Yield: 15%
$^1$H NMR (CDCl$_3$, 300 MHz) δ (ppm): 8.00 (s, 1H), 6.85-7.51 (bulk aromatic, 10H), 6.62 (d, 2H), 3.72-3.88 (m, 11H), 2.81 (m, 2H), 2.43 (m, 5H), 1.25-1.56 (m, 6H)
HPLC: 87%
MS: MH$^+$ 672/674

Stage 7: 5-bromo-2-methoxy-4-[N-(4'-methoxy-biphenyl-4-yl)-N-(2-methyl-6-piperidin-1-yl-phenyl)-hydrazino-carbonylmethyl]-benzoic acid hydrochloride (28)

The product (13 mg) is obtained as a hydrochloride according to the method of stage 6 of Example 2, by using as a substrate the product obtained in the previous stage.

Yield: 52%
Elementary analysis calculated for $C_{35}H_{36}BrN_3O_5 \cdot 1HCl \cdot 1.5H_2O$: C, 58.22; H, 5.58; N, 5.82. Found: C, 58.06; H, 5.63; N, 5.58.
HPLC: 82%
MS: MH$^+$ 658/660

Example 29

5-bromo-4-[N-cyano-phenyl)-N-(2-methyl-6-piperidin-1-yl-phenyl)-hydrazinocarbonylmethyl]-2-methoxy benzoic acid hydrochloride (29)

Stage 1: tert-butyl N-(2-methyl-6-nitro-phenyl)-hydrazino-carboxylate

To 250 mg of 2-fluoro-3-methyl-nitrobenzene in 5 mL of DMSO are added 1.065 g of commercial tert-butoxycarbonylhydrazine (5 equivalents). The whole is brought to 100° C. for 10 min under microwave heating. The medium is hydrolyzed and then extracted with ethyl acetate several times. The organic phases are collected, dried on magnesium sulfate, filtered and evaporated under reduced pressure leading to a residue which is purified by chromatography on silica gel (cyclohexane/ethyl acetate: 80/20). 342 mg of product corresponding to the expected product are obtained.

Yield: 80%

¹H NMR (CDCl₃, 250 MHz) δ (ppm): 7.86 (d, 1H), 7.35 (d, 1H), 6.97 (t, 1H), 6.40 (s broad, 1H), 1.34 (s broad, 9H)
HPLC: 98%

Stage 2: tert-butyl N-(4-cyano-phenyl)-N-(2-methyl-6-nitro-phenyl)-hydrazinocarboxylate To 1.5 g of the product obtained in the previous stage in 10 mL of dichloromethane are added at 0° C., 2.45 g of activated manganese oxide (5 equivalents). The whole is stirred at room temperature for 30 min, until complete disappearance of the starting product (tracked by TLC). The oxidized intermediate is filtered on celite, rinsed with dichloromethane and then concentrated under reduced pressure without any other form of purification. The thereby obtained tert-butyl azocarboxylate derivative is immediately taken up in 10 mL of methanol to which are successively added 1.27 g of 4-cyanophenylboronic acid (1.6 equivalents) and 54 mg of copper acetate hydrate (0.05 equivalents). The whole is refluxed for 24 hrs until complete disappearance of the oxidized intermediate. The reaction medium is hydrolyzed and then extracted with ethyl acetate several times. The organic phases are washed with water, then with brine and finally dried on magnesium sulfate, filtered and evaporated under reduced pressure. The obtained residue is purified by silica gel chromatography (dichloromethane/cyclohexane: 1/1) leading to 1.13 g of the expected product.
Yield: 57%
¹H NMR (CDCl₃, 300 MHz) δ (ppm): 7.98 (d, 1H), 7.67 (t, 2H), 7.49 (m, 3H), 6.60 (d, 2H), 2.49 (s, 3H), 1.48 (s, 9H)
HPLC: 78%

Stage 3: tert-butyl N-(2-amino-6-methyl-phenyl)-N-(4-cyano-phenyl)-hydrazinocarboxylate 982 mg of the product are obtained by catalytic hydrogenation in the presence of 110 mg of 5% palladium on charcoal in 50 mL of ethanol from 1.13 g of the product obtained in the previous stage.
Yield: 97%
¹H NMR (CDCl₃, 300 MHz) δ (ppm): 7.48 (d, 2H), 7.09 (m, 1H), 6.62 (m, 4H), 4.78 (s broad, 2H), 4.40 (s broad, 1H), 2.02 (s, 3H), 1.50 (s, 9H)
HPLC: 80%

Stage 4: tert-butyl N-[2-(5-bromo-pentanoylamino)-6-methylphenyl]-N-(4-cyano-phenyl)-hydrazinocarboxylate To 980 mg of the obtained product of the previous stage in 8 mL of dichloromethane in the presence of 820 μL of DIPEA (2 equivalents) are added dropwise and at room temperature 388 μL of 5-bromovaleryl chloride. After 20 minutes, the reaction crude product hydrolyzed by a 1 N hydrochloric acid solution is extracted with dichloromethane several times. The organic phases are dried on magnesium sulfate, filtered and concentrated under reduced pressure leading to 1.4 g of the expected product.
Yield (estimation): 96%
¹H NMR (CDCl₃, 300 MHz) δ (ppm): 10.03 (s, 1H), 8.28 (d, 1H), 7.49 (d, 1H), 7.34 (t, 2H), 6.95-7.20 (m, 3H), 3.43 (m, 2H), 3.30 (t, 2H), 2.51 (t, 2H), 2.34 (m, 2H), 2.07 (s, 3H), 1.53 (s, 9H)
HPLC: 56%

Stage 5: tert-butyl M-(4-cyano-phenyl)-N-[2-methyl-6-(2-oxo-piperidin-1-yl)-phenyl]-hydrazinocarboxylate To 1.4 g of the obtained previous product in 5 mL of DMF are added 225 mg of sodium hydride (2 equivalents) at 0° C. After 20 minutes at room temperature, the reaction crude product is hydrolyzed and then extracted with ethyl acetate several times. The collected organic phases are washed with water and then with brine and finally dried on magnesium sulfate, filtered and concentrated under reduced pressure leading to 1.1 g of the expected product.
Yield (estimation): quantitative Stage 6: tert-butyl N-[4-(amino-methyl)-phenyl]-N-(2-methyl-6-piperidin-1-yl-phenyl)-hydrazinocarboxylate To 440 mg of the product obtained from the previous stage in 3 mL of THF are added 493 μL of borane dimethylsulfide (5 equivalents). The whole is refluxed for 1 hr. The reaction crude product is hydrolyzed and extracted with ethyl acetate several times. The organic phases are collected, washed with water and then with a 1 N hydrochloric acid solution. The aqueous phase is taken up with a saturated solution of sodium bicarbonate and then extracted with ethyl acetate. The organic phases are collected, dried on magnesium sulfate, filtered and concentrated under reduced pressure leading to 308 mg of the expected product.
Yield (estimation): 710%

Stage 7: tert-butyl N-[4-(acetylamino-methyl)-phenyl]-N-(2-methyl-6-piperidin-1-yl-phenyl)-hydrazino-carboxylate To a solution of 300 mg of the product obtained from the previous stage in 10 mL of tetrahydrofurane under an inert atmosphere are added 267 μL of DIPEA (2 equivalents) and 76 μL of acetic anhydride (1.4 equivalents). The whole is stirred at room temperature for 30 minutes until complete disappearance of the starting product (tracked with TLC). The reaction medium taken up in ethyl acetate is hydrolyzed with a 1 N hydrochloric acid solution and extracted several times. The aqueous phase is then taken up again with a sodium bicarbonate solution until a pH of 8 and extracted with ethyl acetate. The organic phases are collected, dried on magnesium sulfate, filtered and evaporated under reduced pressure. The obtained residue is purified by silica gel chromatography (ether and then dichloromethane) leading to 165 mg of the expected product.
Yield (estimation): 51%
¹H NMR (CDCl₃, 300 MHz) δ (ppm): 8.92 (s broad, 1H), 7.18 (d, 1H), 7.07 (m, 4H), 6.62 (d, 2H), 5.60 (s broad, 1H), 4.32 (m, 2H), 2.80 (m, 2H), 2.65 (m, 2H), 2.31 (s, 3H), 2.01 (s, 3H), 1.60 (m, 6H), 1.44 (s, 9H)

Stage 8: methyl 4-{N-[4-(acetylamino-methyl)-phenyl]-N-(2-methyl-6-piperidin-1-yl-phenyl)-hydrazinocarbonyl-methyl}-5-bromo-2-methoxy-benzoate To a solution of 51 mg of the acid obtained in preparation 2 (2 equivalents) in 2 mL of dichloromethane are added 14.4 μL of oxalyl chloride (2 equivalents) and 1 drop of dimethylformamide. The whole is stirred for 20 min at room temperature and then evaporated under reduced pressure. To the thereby obtained acid chloride, taken up again in 1 mL of acetonitrile, are successively added a solution of 38 mg of the previous ester in 1 mL of acetonitrile and 1 mL of 4 N hydrochloric acid in dioxane. The whole is placed for 10 minutes under microwave heating at 100° C. The reaction medium is hydrolyzed and then extracted with ethyl acetate several times. The aqueous phase is then basified with a 1 N soda solution and extracted with ethyl acetate and then with dichloromethane. The organic phases are collected, dried on magnesium sulfate, filtered and then evaporated under reduced pressure. With a silica gel chromatography of the residue (dichloromethane/ethanol: 98/2) 18 mg of the expected product may be obtained.

Yield: 34%
$^1$H NMR (CDCl$_3$, 300 MHz) δ (ppm): 10.05 et 9.83 (2s broad, 1H), 7.99 (s, 1H), 7.18 (m, 2H), 7.05 (m, 4H), 6.52 (d, 2H), 5.67 (s broad, 1H), 4.29 (d, 2H), 3.88 (s, 3H), 3.73 (m,s, 2H), 3.71 (s, 3H), 2.75 (m, 2H), 2.40 (m, 2H), 2.37 (s, 3H), 1.98 (s, 3H), 1.46 (m, 6H)
HPLC: 97.3%
MS: MH$^+$ 637/639

Stage 9: 4-{N-[4-(acetylamino-methyl)-phenyl]-N-(2-methyl-6-piperidin-1-yl-phenyl)-hydrazinocarbonyl-methyl}-5-bromo-2-methoxy-benzoic acid hydrochloride (29)

The product (13.8 mg) is obtained as a hydrochloride according to the method of stage 6 of Example 2, by using as a substrate the product obtained with the previous stage.

Yield: 75%
HPLC: 91%
MS: MH$^+$ 623/625

Example 30

4-[N-(4-benzoyl-phenyl)-N-(2-piperidin-1-yl-phenyl)-hydrazinocarbonylmethyl]-5-bromo-2-methoxy benzoic acid hydrochloride (30)

Stage 1: (4-benzoyl-phenyl)-(2-nitro-phenyl)-amine

The product (770 mg) is obtained according to the method of stage 1 of Example 4, by using 1.5 mL of 2-fluoro-nitrobenzene and 4.2 g of 4-aminobenzophenone in the presence of 2.54 g of potassium tert-butanolate in 40 mL of DMSO.

Yield: 17%
HPLC: 86%
MS: MH$^+$ 319

Stage 2: N-(4-Benzoyl-phenyl)-benzene-1,2-diamine

The product (880 mg) is obtained according to the method of stage 2 of Example 1, by using 770 mg of the previous derivative as a starting product and 2.73 g of tin chloride hydrate in 15 mL of ethanol.

Yield: quantitative
$^1$H NMR (CDCl$_3$, 300 MHz) δ (ppm): 7.74 (t, 4H), 7.36-7.53 (m, 3H), 7.13 (m, 2H), 6.70-6.85 (m, 4H), 5.63 (s broad, 1H), 3.80 (s broad, 1H)
HPLC: 82%
MS: MH$^+$ 289

Stage 3: (4-benzoyl-phenyl)-(2-piperidin-1-yl-phenyl)-amine

The product (530 mg) is obtained according to the method of stage 3 of Example 4, by using 697 mg of the previous derivative as a starting product, 330 µL of dibromopentane and 1.01 mL of DIPEA in 15 mL of toluene.

Yield: 62%
$^1$H NMR (CDCl$_3$, 300 MHz) δ (ppm): 7.80 (dd, 4H), 7.45-7.56 (m, 4H), 6.96-7.18 (m, 6H), 2.84 (m, 4H), 1.60-1.74 (m, 6H)
HPLC: 100%
MS: MH$^+$ 357

Stage 4: N-(4-benzoyl-phenyl)-N-(2-piperidin-1-yl-phenyl)-hydrazine (v)

To a solution of 100 mg of the previous compound in 10 mL of DMF are added 14 mg of sodium hydride (1.2 equivalents) and the whole is stirred at room temperature for 45 minutes. 2.3 mL of a freshly prepared 0.15 M solution in monochloramine ether (1.2 equivalents) (*J. Org. Chem.* 2004, 69, 1368-1371) is added. After 5 minutes, the medium is treated by a saturated solution of Na$_2$S$_2$O$_3$, taken up again with water and then extracted with ether several times. The organic phases are dried on magnesium sulfate, filtered and concentrated under reduced pressure. The obtained residue is purified by silica gel chromatography (petroleum ether/ethyl acetate: 95/5) leading to 75 mg of the expected product.

Yield: 72%
$^1$H NMR (CDCl$_3$, 250 MHz) δ (ppm): 7.73 (d, 4H), 7.48 (m, 3H), 7.25 (m, 2H), 7.05-7.17 (m, 4H), 4.89 (s broad, 2H), 2.91 (m, 4H), 1.57 (m, 6H)
HPLC: 100%
MS: MH$^+$ 372

Stage 5: methyl 4-[N-(4-benzoyl-phenyl)-N-(2-piperidin-1-yl-phenyl)-hydrazinocarbonylmethyl]-5-bromo-2-methoxy-benzoate The product (83 mg) is obtained according to the method of stage 3 of Example 6, by using 70 mg of the preceding hydrazine and 64 mg of the acid of preparation 2 in the presence of 41 mg of EDCI and 28 mg of HOBt in 1.5 mL of dimethylformamide.

Yield: 66%
$^1$H NMR (CDCl$_3$, 300 MHz) δ (ppm): 9.36 (s broad, 1H), 7.99 (s, 1H), 6.80-7.76 (bulk aromatic, 14H), 3.89 (s, 3H), 3.80 (s, 2H), 3.72 (s, 3H), 2.75 (m, 4H), 1.54 (m, 6H)
HPLC: 100%
MS: MH$^+$ 656/658

Stage 6: 4-[N-(4-benzoyl-phenyl)-N-(2-piperidin-1-yl-phenyl)-hydrazinocarbonylmethyl]-5-bromo-2-methoxy benzoic acid hydrochloride (30)

The product (31 mg) is obtained according to the method of stage 6 of Example 2, by using as a substrate the product obtained in the previous stage.

Yield: 37%
Elementary analysis calculated for C$_{34}$H$_{32}$BrN$_3$O$_5$.1HCl.1.5H$_2$O: C, 57.84; H, 5.14; N, 5.95. Found: C, 58.04; H, 5.13; N, 5.55.
HPLC: 100%
MS: MH$^+$ 642/644

Example 31

5-bromo-4-[N-cyano-phenyl)-N-(2-methyl-6-piperidin-1-yl-phenyl)-hydrazinocarbonylmethyl]-2-methoxy benzoic acid hydrochloride (31)

Stage 1: tert-butyl N-(4-cyano-phenyl)-N-(2-methyl-6-piperidin-1-yl-phenyl)-hydrazinocarboxylate To 280 mg of the product obtained in stage 5 of Example 29 in 2 mL of tetrahydrofurane are added 3.3 mL of a 1 M borane solution in tetrahydrofurane (5 equivalents). The whole is refluxed for 3 hrs. The reaction crude product is poured on a 1 N acid hydrochloric solution and extracted with ethyl acetate several times. The aqueous phase is basified by a 1 N soda solution and extracted with dichloromethane. The different organic phases are collected, washed with water and then with a saturated solution of NaCl, dried on magnesium sulfate, filtered and concentrated under reduced pressure. The obtained residue is purified by silica gel chromatography (dichloromethane/ethyl acetate: 98/2) leading to 82 mg of expected product.

Yield: 30%
$^1$H NMR (CDCl$_3$, 300 MHz) δ (ppm): 8.92 (s broad, 1H), 7.46 (d, 2H), 7.21 (m, 1H), 7.06 (t, 2H), 6.72 (m, 2H), 2.74 (m, 4H), 2.29 (s, 3H), 1.60 (m, 6H), 1.43 (s, 9H)

Stage 2: methyl 5-bromo-4-[N-(4-cyano-phenyl)-N-(2-methyl-6-piperidin-1-yl-phenyl)-hydrazino-carbonyl-methyl]-2-methoxy-benzoate The product (32 mg) is obtained according to the method of stage 8 of Example 31, by using 42 mg of the product obtained in the previous stage as a substrate and 94 mg of the acid of preparation 2 as a co-substrate.

Yield: 56%
$^1$H NMR (CDCl$_3$, 300 MHz) δ (ppm): 9.78 (s, 1H), 7.98 (s, 1H), 7.45 (d, 2H), 7.24 (m, 2H), 7.01 (m, 2H), 6.62 (m, 2H), 3.88 (s, 2H), 3.37 (s, 6H), 2.70 (m, 2H), 2.45 (m, 2H), 2.35 (s, 3H), 1.42 (m, 6H)
HPLC: 94%
MS: MH$^+$ 591/593

Stage 3: 5-bromo-4-[N-(4-cyano-phenyl)-N-(2-methyl-6-piperidin-1-yl-phenyl)-hydrazinocarbonylmethyl]-2-methoxy-benzoic acid hydrochloride (31)

The product (16.4 mg) is obtained as a hydrochloride according to the method of stage 6 of Example 2, by using as a substrate the product obtained in the previous stage.

Yield: 49%
HPLC: 98%
MS: MH$^+$ 577/579

Example 32

4-[N-(4'-acetyl-biphenyl-4-yl)-N-(2-methyl-6-piperidin-1-yl-phenyl)-hydrazinocarbonylmethyl]-5-bromo-2-methoxy-benzoic acid hydrochloride (32)

Stage 1: (4'-acetyl-biphenyl-4-yl)-(2-methyl-6-piperidin-1-yl-phenyl)-amine

The product (1.35 g) is obtained according to the method of stage 4 of Example 11, by using 2.6 g of the derivative obtained in stage 3 of Example 28 as a starting product, 248 g of 4-acetyl-phenylboronic acid, 307 mg of [1,1'-bis(diphenylphosphino)ferrocene]-dichloropalladium (II) and 4.58 g of cesium fluoride in 150 mL of dioxane.

Yield: 470
$^1$H NMR (CDCl$_3$, 200 MHz) δ (ppm): 7.98 (d, 2H), 7.65 (d, 2H), 7.51 (d, 2H), 7.03 (m, 3H), 6.76 (d, 2H), 6.29 (s broad, 1H), 2.75 (m, 4H), 2.63 (s, 3H), 2.17 (s, 3H), 1.58 (m, 6H)
SM: MH$^+$ 385

Stage 2: [4'-(2-methyl-[1,3]dithian-2-yd)-biphenyl-4-yl]-(2-methyl-6-piperidin-1-yl-phenyl)-amine To a solution of 788 mg of the derivative obtained in the previous stage in 14 mL of dichloromethane are successively added 260 μL of propanedithiol (1.25 equivalents) and 380 μL of boron trifluoride complexed with diethyl ether. The whole is stirred for 2 days at room temperature until disappearance of the starting product. The reaction medium is poured on a 2 N soda solution and then extracted with dichloromethane several times. The organic phases are washed with a saturated solution of sodium chloride, dried on sodium sulfate, filtered and concentrated under reduced pressure leading to 970 mg of the expected product.

Yield: quantitative
$^1$H NMR (CDCl$_3$, 200 MHz) δ (ppm): 7.96 (d, 2H), 7.58 (d, 2H), 7.48 (d, 2H), 7.03 (m, 3H), 6.77 (d, 2H), 6.26 (s broad, 1H), 2.76 (m, 8H), 2.18 (s, 3H), 1.95 (m, 2H), 1.84 (s, 3H), 1.54 (m, 6H)

Stage 3: N-[4'-(2-methyl-[1,3]dithian-2-yl)-biphenyl-4-yl]-N-(2-methyl-6-piperidin-1-yl-phenyl)-hydrazine (w)

The product (835 mg) is obtained according to the method of stage 4 of Example 1, by using 970 mg of the previous derivative as a starting product and 1.11 g of sodium nitrite in 6 mL of acetic acid leading to the nitroso intermediate which is reduced by 8.2 mL of a 1 M lithium aluminium hydride solution in ether (4 equivalents) in 8 mL of ether with reflux.

Yield: 83%
$^1$H NMR (CDCl$_3$, 200 MHz) δ (ppm): 7.92 (d, 2H), 7.57 (d, 2H), 7.46 (d, 2H), 7.19 (d, 1H), 7.05 (t, 2H), 6.90 (d, 2H), 2.70-2.95 (m, 8H), 2.12 (s, 3H), 1.96 (m, 2H), 1.82 (s, 3H), 1.65 (m, 6H)

Stage 4: methyl 5-bromo-2-methoxy-4{N-[4'-(2-methyl-[1,3]dithian-2-yl)-biphenyl-4-yl]-N-(2-methyl-6-piperidin-1-yl-phenyl)-hydrazinocarbonyl-methyl}-benzoate The product (637 mg) is obtained according to the method of stage 3 of Example 6, by using 600 mg of the previous hydrazine and 406 mg of the acid of preparation 2 in the presence of 257 mg of EDCI and 181 mg of HOBt in 4 mL of dimethylformamide.

Yield: 67%
$^1$H NMR (CDCl$_3$, 200 MHz) δ (ppm): 9.87 (s broad, 1H), 7.96 (m, 3H), 7.50 (m, 5H), 7.20 (d, 1H), 7.03 (m, 2H), 6.65 (d, 2H), 3.88 (s, 3H), 3.70 (2s, 5H), 2.75 (m, 8H), 2.44 (s, 3H), 1.97 (m, 2H), 1.81 (s, 3H), 1.25-1.55 (m, 6H)
MS: MH$^+$ 774/776

Stage 5: methyl 4-[N-(4'-acetyl-biphenyl-4-yl)-N-(2-methyl-6-piperidin-1-yl-phenyl)-hydrazinocarbonyl-methyl]-5-bromo-2-methoxy-benzoate To a solution of 30 mg of the derivative obtained in the previous stage in 100 μL of a tetrahydrofurane/water mixture (1:1) are successively added 17 mg of mercury(II) oxide (2 equivalents) and 10 µL of boron trifluoride complexed with ether (2 equivalents). The whole is stirred at room temperature for 1 hour, until disappearance of the starting product. The reaction medium is poured in a 2 M soda bicarbonate solution and then extracted with ethyl acetate several times. The organic phases are washed with a saturated solution of sodium chloride, dried on sodium sulfate, filtered and concentrated under reduced pressure. Silica gel chromatography (cyclohexane/ethyl acetate: 70/30) is able to isolate 19.5 mg of the desired product.

Yield: 73% $^1$H NMR (CDCl$_3$, 200 MHz) δ (ppm): 9.88 (s broad, 1H), 7.97 (m, 3H), 7.62 (d, 2H), 7.48 (d, 2H), 7.21 (d, 1H), 7.03 (m, 2H), 6.67 (d, 2H), 3.89 (s, 3H), 3.77 (2s, 5H), 2.80 (m, 2H), 2.62 (s, 3H), 2.42 (m+s, 5H), 1.30-1.50 (m, 6H)

MS: MH$^+$ 684/686

Stage 6: 4-[N-(4'-acetyl-biphenyl-4-yl)-N-(2-methyl-6-piperidin-1-yl-phenyl)-hydrazinocarbonylmethyl]-5-bromo-2-methoxy-benzoic acid hydrochloride (32)

The product (115 mg) is obtained as a hydrochloride form according to the method of stage 6 of Example 2, by using as a substrate the product obtained in the previous stage.

Yield: 34%

$^1$H NMR (DMSO, 400 MHz) δ (ppm): 7.99 (m, 3H), 7.37-7.81 (m, 7H), 7.37 (s, 1H), 6.78 (m, 2H), 4.24 (d, 1H), 4.03 (d, 1H), 3.79 (s, 3H), 3.20-3.60 (m, 4H), 2.57 (s, 3H), 2.28 (s, 3H), 1.51-1.86 (m, 6H)

HPLC: 96%

MS: MH$^+$ 670/672

Example 33

5-bromo-2-methoxy-4-[N-(4'-methoxy-2-methyl-biphenyl-4-yl)-N-(2-methyl-6-piperidin-1-yl-phenyl)-hydrazinocarbonylmethyl]-benzoic acid hydrochloride (33)

Stage 1: (4-bromo-3-methyl-phenyl)-(2-methyl-6-nitro-phenyl)-amine

The product (3.90 g) is obtained according to the method of stage 1 of Example 4, by using 2.78 g of 2-fluoro-3-methyl-nitrobenzene and 5 g of 4-bromo-3-methyl-aniline in the presence of 3.22 g of potassium tert-butanolate in 70 mL of DMSO.

Yield: 68%

$^1$H NMR (CDCl$_3$, 200 MHz) δ (ppm): 8.15 (s broad), 7.96 (d, 1H), 7.43 (d, 1H), 7.37 (m, 1H), 7.10 (t, 1H), 6.65 (m, 1H), 6.42 (dd, 1H), 2.33 (s, 3H), 2.10 (s, 3H)

Stage 2: N$^2$-(4-bromo-3-methyl-phenyl)-3-methyl-benzene-1,2-diamine

The product (3.2 g) is obtained according to the method of stage 2 of Example 1, by using 3.9 g of the previous derivative as a starting product and 13.7 g of tin chloride hydrate in 60 mL of ethanol.

Yield: 90%

$^1$H NMR (CDCl$_3$, 200 MHz) δ (ppm): 7.29 (d, 1H), 7.03 (t, 1H), 6.68 (d, 2H), 6.47 (d, 1H), 6.28 (dd, 1H), 4.94 (s broad, 1H), 2.29 (s, 3H), 2.16 (s, 3H)

Stage 3: (4-bromo-3-methyl-phenyl)-(2-methyl-6-piperidin-1-yl-phenyl)-amine

The product (3.21 g) is obtained according to the method of stage 3 in Example 4, by using 3.2 g of the previous derivative as a starting product, 1.50 mL of dibromopentane and 4.30 mL of DIPEA in 50 mL of toluene.

Yield: 81%

$^1$H NMR (CDCl$_3$, 200 MHz) δ (ppm): 7.28 (d, 1H), 7.04 (m, 3H), 6.58 (d, 1H), 6.41 (dd, 1H), 6.13 (s broad, 1H), 2.72 (m, 4H), 2.32 (s, 3H), 2.11 (s, 3H), 1.57 (m, 6H)

Stage 4: (4'-methoxy-2-methyl-biphenyl-4-yl)-(2-methyl-6-piperidin-1-yl-phenyl-amine The product (1.921 g) is obtained according to the method of stage 4 of Example 11, by using 3 g of the previous derivative as a starting product, 1.904 g of 4-methoxyphenyl boronic acid, 392 mg of palladium tetrakis, 1.062 g of lithium chloride in the presence of 9 mL of a 1 M sodium carbonate solution in 60 mL of a methanol/toluene mixture (1:1).

Yield: 60%

$^1$H NMR (CDCl$_3$, 200 MHz) δ (ppm): 7.28 (d, 2H), 7.03 (m, 6H), 6.59 (m, 2H), 6.26 (s broad, 1H), 3.86 (s, 3H), 2.77 (m, 4H), 2.25 (s, 3H), 2.20 (s, 3H), 1.63 (m, 6H)

Stage 5: N-(4'-methoxy-2-methyl-biphenyl-4-yl)-N-(2-methyl-6-piperidin-1-yl-phenyl)-hydrazine (x)

The product (385 mg) is obtained according to the method of stage 4 of Example 1, by using 490 mg of the previous derivative as a starting product and 515 mg of sodium nitrite in 4 mL of acetic acid leading to the nitroso intermediate which is reduced with 4.8 mL of a 1 M lithium aluminium hydride solution in ether (4 equivalents) in 4.5 mL of ether with reflux.

Yield: 80%

$^1$H NMR (CDCl$_3$, 200 MHz) δ (ppm): 6.90-7.27 (bulk aromatic, 10H), 6.78 (s broad, 1H), 6.57 (d, 1H), 3.83 (s, 3H), 2.92 (m, 4H), 2.22 (s, 3H), 2.12 (s, 3H), 1.68 (m, 4H), 1.53 (m, 2H)

Stage 6: methyl 5-bromo-2-methoxy-4-[N-(4'-methoxy-2-methyl-biphenyl-4-yl)-N-(2-methyl-6-piperidin-1-yl-phenyl)-hydrazinocarbonylmethyl]-benzoate The product (450 mg) is obtained according to the method of stage 3 of Example 6, by using 381 mg of the previous hydrazine and 316 mg of the acid of preparation 2 in the presence of 200 mg of EDCI and 144 mg of HOBt in 3.8 mL of dimethylformamide.

Yield: 69%

$^1$H NMR (CDCl$_3$, 200 MHz) 10.06 et 9.84 (2 s broad, 1H), 8.01 (s, 1H), 7.20 (m, 4H), 6.89-7.02 (m, 5H), 6.50 (s, 1H), 6.38 (d, 1H), 3.89 (s, 3H), 3.84 (s, 3H), 3.76 (m, 2H), 3.72 (s, 3H), 2.80 (m, 2H), 2.45 (m, 5H), 2.18 (s, 3H), 1.30-1.58 (m, 6H)

Stage 7: 5-bromo-2-methoxy-4-[N-(4'-methoxy-2-methyl-biphenyl-4-yl)-N-(2-methyl-6-piperidin-1-yl-phenyl)-hydrazinocarbonylmethyl]-benzoic acid hydrochloride (33)

The product (264 mg) is obtained as a hydrochloride according to the method of stage 6 of Example 2, by using as a substrate the product obtained in the previous stage.

Yield: 67%

$^1$H NMR (DMSO, 200 MHz) δ (ppm): 11.79 (s broad, 1H), 11.44 (s broad, 1H), 7.96 (d, 1H), 7.81 (s, 1H), 7.70 (m, 2H), 7.34 (s, 1H), 7.23 (d, 2H), 6.99 (d, 1H), 6.75 (d, 2H), 6.44 (s, 1H), 6.42 (d, 1H), 4.10 (m, 2H), 3.78 (s, 6H), 3.40 (m, 4H), 2.27 (s, 3H), 2.19 (s, 3H), 1.53-1.86 (m, 6H)

HPLC: 98.5%

MS: MH$^+$ 672/674

RESULTS OF BIOLOGICAL ACTIVITY

Activity of molecules against the papilloma virus may be evaluated in different in vitro and cell tests such as those described by Chiang et al. (1992), *Proc. Natl. Acad. Sci. USA*, 89: 5799-5803 or further by White et al. (2003), *Journal of Biological Chemistry*, 278: 26765-26772.

Example 34

Pharmacological Studies of the Compounds of the Invention in Cell Tests for Replication of Viral DNA of HPVs These tests measure replication of viral genomic DNA in human cells. They are based on co-transfection of a reporter vector containing a viral replication origin (ori) and of expression vectors coding for the E1 and E2 proteins of HPV. With them, it is possible to follow the whole of the biological functions of E1 and E2 required for replicating the HPV genome.

A reporter 'replicon' vector containing the viral replication origin of HPV11/HPV6 (also called LCRs which bear sites for binding the E1 and E2 proteins of HPV) and the gene coding for firefly luciferase under the transcriptional control of the SV40 promoter were built. It was checked that the presence of the HPV replication origin does not have any transcriptional effect on expression of the gene of luciferase, this in the presence or in the absence of viral E1 or E2 proteins. Co-transfection of this replicon vector and of vectors for expressing HPV E1 and E2 proteins leads to an increase in luciferase activity depending on the presence of E1 and E2 and expresses the increase in the number of reporter vectors. This is due to the activity of the viral E1 and E2 proteins which allow replication, in mammal cells, of this replicon vector containing a viral replication origin.

The chemical compounds were evaluated for their activity inhibiting viral replication dependent on E1 and E2 of HPV11/HPV6 in these cell tests by co-transfecting, in human cell lines derived from kidney epithelial or cervical carcinoma cells, the replicon-reporter vector and pairs of HPV11/HPV6 E1 and E2 expression vectors. Various doses of the compounds were incubated for 2-6 days after transfection in the cell medium and luciferase activity was determined by means of a luminometer in order to evaluate IC$_{50}$ of the compounds on replication of the HPV genome.

All the compounds shown in the examples above inhibit replication dependent on E1 and E2 of HPV11/HPV6 in cells with an IC$_{50}$ less than 20 µM. The preferred compounds are those for which IC$_{50}$ may be less than 750 nM.

With complementary cell tests, it was possible to show that the compounds shown in the examples above inhibit HPV11 and HPV6 E1/E2 interaction.

The invention claimed is:

1. A method for treating an infection by the HPV 6 or HPV 11 papilloma virus comprising the administration to a patient in need thereof of an efficient quantity of a compound of formula (I):

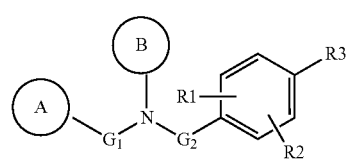

or a stereoisomer thereof, wherein:

G$_1$ is a methylene or ethylene bond,

G$_2$ is CH$_2$ or trans-ethylene,

R$_1$ is O—CH$_3$, and R$_2$ is H, F, Cl or Br at the 5-position,

R$_3$ is C(=O)OH wherein R$_3$ is at the 1-position,

A is a phenyl, each optionally substituted at the 4- and/or 3-position, and

B is a phenyl, substituted with piperidin-1-yl, at the 2- and/or 6-position, and optionally substituted with methyl at the other of the 2- or 6-position, or its pharmaceutically acceptable salt.

2. The method according to claim 1, wherein A is substituted with one or two groups, either identical or different, selected from:

a halogen atom, an alkoxy, alkylthio, haloalkoxy, haloalkylthio, hydroxyl, thio, cyano, amino, monoalkylamino, or dialkylamino group, an —SO$_n$R', —COR', —CO$_2$R', —OCOR', —CONR'R", —NR'COR" or —NR'SO$_2$R" group, wherein R' and R" each represent independently of each other an hydrogen atom, an alkyl, haloalkyl group, and n has the value 1 or 2, an alkyl or haloalkyl group, the alkyl group being optionally substituted with a cyano, amino, monoalkylamino, dialkylamino or acylamino group, an aryl, arylalkyl, —X-aryl, —X-arylalkyl or -Alk-X-aryl group wherein X is —O—, —NH—, —N(Alk)-, —N(COCH$_3$)—, —S—, —SO—, —SO$_2$—, —CO— or —CONH—, each substituted on the aryl portion with one or two substituents, either identical or different, selected from:

a halogen atom, an alkyl, haloalkyl, alkoxy, haloalkoxy, thio, alkylthio, haloalkylthio, hydroxyl, cyano, acyl, amino, monoalkylamino or dialkylamino, acid, ester, amide, mono- or di-alkylamide group, an —SO$_n$R', —COR', —CO$_2$R', —OCOR', —CONR'R", —NR'COR" or —NR'SO$_2$R" group, wherein R' and R" each represent independently of each other a hydrogen atom, an alkyl, haloalkyl group and n has the value 1 or 2, a heterocycle, -Alk-heterocycle, —X-heterocycle, —X-Alk-heterocycle, or -Alk-X-heterocycle group, wherein X is —O—, —NH—, —N(Alk)-, —N(COCH$_3$)—, —S—, —SO—, —SO$_2$—, —CO—, or —CONH—, each optionally substituted on the heterocycle portion with one or two substituents either identical or different, selected from:

a halogen atom, an alkyl, haloalkyl, alkoxy, haloalkoxy, thio, haloalkylthio, hydroxyl, cyano, acyl, amino, monoalkylamino or dialkylamino, acid, ester, amide, mono- or di-alkylamide group, or —SO$_n$R', —COR', —CO$_2$R', —OCOR', —CONR'R", —NR'COR" or NR'SO$_2$R" group, wherein R' and R"

each represent independently of each other a hydrogen atom, an alkyl, haloalkyl group and n has the value 1 or 2,
a cycloalkyl, -Alk-cycloalkyl, cycloalkenyl, -Alk-cycloalkenyl, —X-cycloalkyl, —X-Alk-cycloalkyl, —X-cycloalkenyl, —X-Alk-cycloalkenyl, -Alk-X-cycloalkyl, -Alk-X-cycloalkenyl group, wherein X is —O—, —NH—, —N(Alk)-, —N(COCH$_3$)—, —S—, —SO—, —SO$_2$—, —CO— or —CONH— each optionally substituted on the cyclic portion with one or two substituents, either identical or different, selected from:
a halogen atom,
an alkyl, haloalkyl, alkoxy, haloalkoxy, thio, alkylthio, haloalkylthio, hydroxyl, cyano, acyl, amino, mono-alkylamino or dialkylamino, acid, ester, amide, mono- or di-alkylamide, or oxo or
—SO$_n$R', —COR', —CO$_2$R', —OCOR', —CONR'R", —NR'COR" or NR'SO$_2$R" group, wherein R' and R" each represent independently of each other a hydrogen atom, an alkyl, haloalkyl group and n has the value 1 or 2.

3. The method according to claim 1 wherein the compound of formula (I) is selected from:
1) 5-bromo-2-methoxy-4-[N'-(4-methoxy-phenyl)-N'-(2-piperidin-1-yl-phenyl)-hydrazinocarbonylmethyl]-benzoic acid hydrochloride
2) 5-bromo-2-methoxy-4-[N'-(2-piperidin-1-yl-phenyl)-N'-(4-trifluoromethoxy-phenyl)-hydrazinocarbonylmethyl]-benzoic acid hydrochloride
3) 5-bromo-2-methoxy-4-[N'-(3-methoxy-benzyl)-N'-(2-piperidin-1-yl-phenyl)-hydrazinocarbonylmethyl]-benzoic acid hydrochloride
4) 4-[N'-(4-benzyloxy-phenyl)-N'-(2-piperidin-1-yl-phenyl)-hydrazinocarbonylmethyl]-5-bromo-2-methoxy-benzoic acid hydrochloride
5) 5-bromo-4-{N'-[4-(4-fluoro-phenoxy)-phenyl]-N'-(2-piperidin-1-yl-phenyl)-hydrazinocarbonylmethyl}-2-methoxy-benzoic acid hydrochloride
6) 5-bromo-2-methoxy-4-{N'-[2-(4-methoxy-phenyl)-ethyl]-N'-2-piperidin-1-yl-phenyl)-hydrazinocarbonylmethyl}-benzoic acid hydrochloride
7) 5-bromo-2-methoxy-4-[N'-(4-methoxy-phenyl)-N'-(2-methyl-6-piperidin-1-yl-phenyl)-hydrazinocarbonylmethyl]-benzoic acid hydrochloride
7a) Methyl 5-bromo-2-methoxy-4-[N'-(4-methoxy-phenyl)-N'-(2-methyl-6-piperidin-1-yl-phenyl)-hydrazinocarbonyl-methyl]-benzoate
8) 5-bromo-2-methoxy-4-[N'-(4-methoxy-benzyl)-N'-(2-piperidin-1-yl-phenyl)-hydrazinocarbonylmethyl]-benzoic acid hydrochloride
9) 5-bromo-4-[N'-(4-cyclohexyl-phenyl)-N'-(2-piperidin-1-yl-phenyl)-hydrazinocarbonylmethyl]-2-methoxy-benzoic acid hydrochloride
10) 5-bromo-2-methoxy-4-[N'-(2-methyl-6-piperidin-1-yl-phenyl)-N'-(4-trifluoromethoxy-phenyl)-hydrazinocarbonylmethyl]-benzoic acid hydrochloride
11) 5-bromo-2-methoxy-4-[N'-(4'-methoxy-biphenyl-4-yl)-N'-(2-piperidin-1-yl-phenyl)-hydrazinocarbonylmethyl]-benzoic acid hydrochloride
12) 5 bromo-4-[N'-(4-cyclohexyloxy-phenyl)-N'-(2-piperidin-1-yl-phenyl)-hydrazinocarbonylmethyl]-2-methoxy-benzoic acid hydrochloride
13) 5-bromo-2-methoxy-4-[N'-(4-phenoxy-phenyl)-N'-(2-piperidin-1-yl-phenyl)-hydrazinocarbonylmethyl]-benzoic acid hydrochloride
14) 5-bromo-4-{N'-[4-(4-chloro-phenoxy)-phenyl]-N'-(2-piperidin-1-yl-phenyl)-hydrazinocarbonylmethyl}-2-methoxy-benzoic acid hydrochloride
15) 4-{N'-[4-(4-fluoro-phenoxy)-phenyl]-N'-(2-methyl-6-piperidin-1-yl-phenyl)-hydrazinocarbonylmethyl}-2-methoxy-benzoic acid hydrochloride
16) 5-bromo-4-{N'-[4-(4-fluoro-phenoxy)-phenyl]-N'-(2-methyl-6-piperidin-1-yl-phenyl)-hydrazino-carbonylmethyl}-2-methoxy-benzoic acid hydrochloride
16a) Methyl 5-bromo-4-{N'-[4-(4-fluoro-phenoxy)-phenyl]-N'-(2-methyl-6-piperidin-1-yl-phenyl)-hydrazinocarbonyl-methyl}-2-methoxy-benzoate
17) 4-[N'-(4-benzyl-phenyl)-N'-(2-piperidin-1-yl-phenyl)-hydrazinocarbonylmethyl]-5-bromo-2-methoxy-benzoic acid hydrochloride
18) 4-[N'-(4-bromo-phenyl)-N'-(2-piperidin-1-yl-phenyl)-hydrazinocarbonylmethyl]-5-chloro-2-methoxy-benzoic acid hydrochloride
19) 4-[N'-(3'-acetyl-biphenyl-4-yl)-N'-(2-piperidin-1-yl-phenyl)-hydrazinocarbonylmethyl]-5-chloro-2-methoxy-benzoic acid hydrochloride
20) 4-[N'-(4'-acetyl-biphenyl-4-yl)-N'-(2-piperidin-1-yl-phenyl)-hydrazinocarbonylmethyl]-5-chloro-2-methoxy-benzoic acid hydrochloride
21) 5-bromo-2-methoxy-4-[N'-(3-phenoxy)-phenyl]-N'-(2 piperidin-1-yl-phenyl)-hydrazinocarbonylmethyl]-benzoic acid hydrochloride
22) 5-bromo-2-methoxy-4-[N'-(4-phenylsulfanyl)-phenyl]-N'-(2-piperidin-1-yl-phenyl)-hydrazinocarbonylmethyl]-benzoic acid hydrochloride
23) 4-[N'-(4-benzenesulfonyl-phenyl)-N'-(2-piperidin-1-yl-phenyl)-hydrazinocarbonylmethyl]-5-bromo-2-methoxy-benzoic acid hydrochloride
24) 4-[N'-(4-benzenesulfinyl-phenyl)-N'-(2-piperidin-1-yl-phenyl)-hydrazinocarbonylmethyl]-5-bromo-2-methoxy-benzoic acid hydrochloride
25) 2-methoxy-4-{(E)-2-[N'-(4-methoxy-phenyl)-N'-(2-methyl-6-piperidin-1-yl-phenyl)-hydrazinocarbonyl]-vinyl}-benzoic acid hydrochloride
26) 5-bromo-2-methoxy-4-{(E)-2-[N'-(4-methoxy-phenyl)-N'-(2-methyl-6-piperidin-1-yl-phenyl)-hydrazinocarbonyl]-vinyl}-benzoic acid hydrochloride
27) 4-[N'-(4-benzyl-phenyl)-N'-(2-methyl-6-piperidin-1-yl-phenyl)-hydrazinocarbonylmethyl]-5 bromo-2-methoxy-benzoic acid hydrochloride
28) 5-bromo-2-methoxy-4-[N'-(4'-methoxy-biphenyl-4-yl)-N'-(2-methyl-6-piperidin-1-yl-phenyl)-hydrazinocarbonyl-methyl]-benzoic acid hydrochloride
29) 4-[N'-(acetylamino-methyl)-phenyl]-N'-(2-methyl-6-piperidin-1-yl-phenyl)-hydrazinocarbonylmethyl]-5-bromo-2-methoxy-benzoic acid hydrochloride
30) 4-[N'-(4-benzoyl-phenyl]-N'-(2piperidin-1-yl-phenyl)-hydrazinocarbonylmethyl]-5-bromo-2-methoxy-benzoic acid hydrochloride
31) 5-bromo-4-[N'-(4-cyano-phenyl)-N'-(2-methyl-6-piperidin-1-yl-phenyl)-hydrazinocarbonylmethyl]-2-methoxy-benzoic acid hydrochloride
32) 4-[N'-(4'-acetyl-biphenyl-4-yl)-N'-(2-methyl-6-piperidin-1-yl-phenyl)-hydrazinocarbonylmethyl]-5-bromo-2-methoxy-benzoic acid hydrochloride
33) 5-bromo-2-methoxy-4-[N'-(4'-methoxy-2-methyl-biphenyl 4-yl)-N'-(2-methyl-6-piperidin-1-yl-phenyl)-hydrannocarbonytmethyl]-benzoic acid hydrochloride.

4. The method according to claim 1, wherein the patient has a lesion associated with an infection by the papilloma virus.

5. The method according to claim 1, wherein the patient has an ano-genital wart, laryngeal, conjunctive or buccal papilloma or an epithelial lesion.

6. The method according to claim 5, wherein the said ano-genital wart is an acuminated condyloma or a plane condyloma.

7. The method according to claim 5, wherein the said other epithelial lesion is a recurrent respiratory papillonatoses or a low grade or a high grade intra-epithelial neoplasia, a bowenoid papulosis, wart, epidermodysplasia verruciformis, carcinoma, or a lesion associated with the papilloma virus.

8. The method according to claim 7, wherein the said wart is a verruca vulgaris, a verruca plantaris, a myrnecia wart, a surface wart or a verruca plana.

9. The method according to claim 7, wherein the said carcinoma is an ano-genital carcinoma.

10. A method for treating an infection by the HPV 6 or HPV 11 papilloma virus comprising administering to a patient in need thereof a compound selected from the group consisting of:
  1) 5-bromo-2-methoxy-4-[N'-(-4-methoxy-phenyl)-N'-(2-piperidin-1-yl-phenyl)-hydrazinocarbonylmethyl]-benzoic acid hydrochloride
  2) 5-bromo-2-methoxy-4-[N'-(2-piperidin-1-yl-phenyl)-N'-(4-trifluoromethoxy-phenyl)-hydrazinocarbonylmethyl]-benzoic acid hydrochloride;
  3) 5-bromo-2-methoxy-4-[N'-(3-methoxy-benzyl)-N'-(2-piperidin-1-yl-phenyl)-hydrazinocarbonylmethyl]-benzoic acid hydrochloride;
  4) 4-[N'-(4-benzyloxy-phenyl)-N'-(2-piperidin-1-yl-phenyl)-hydrazinocarbonylmethyl]-5-bromo-2-methoxy-benzoic acid hydrochloride;
  5) 5-bromo-4-{N'-[4-(4-fluoro-phenoxy)-phenyl]-N'-(2-piperidin-1-yl-phenyl)-hydrazinocarbonylmethyl}-2-methoxy-benzoic acid hydrochloride;
  6) 5-bromo-2-methoxy-4-{N'-[2-(4-methoxy-phenyl)-ethyl]-N'-2-piperidin-1-yl-phenyl)-hydrazinocarbonylmethyl}-benzoic acid hydrochloride;
  7) 5-bromo-2-methoxy-4-[N'-(4-methoxy-phenyl)-N'-(2-methyl-6-piperidin-1-yl-phenyl)-hydrazinocarbonylmethyl]-benzoic acid hydrochloride;
  7a) Methyl 5-bromo-2-methoxy-4-[N'-(4-methoxy-phenyl)-N'-(2-methyl-6-piperidin-1-yl-phenyl)-hydrazinocarbonyl-methyl]-benzoate;
  8) 5-bromo-2-methoxy-4-[N'-(4-methoxy-benzyl)-N'-(2-piperidin-1-yl-phenyl)-hydrazinocarbonylmethyl]-benzoic acid hydrochloride;
  9) 5-bromo-4-[N'-(4-cyclohexyl-phenyl)-N'-(2-piperidin-1-yl-phenyl)-hydrazinocarbonylmethyl]-2-methoxy-benzoic acid hydrochloride;
  10) 5-bromo-2-methoxy-4-[N'-(2-methyl-6-piperidin-1-yl-phenyl)-N'-(4-trifluoromethoxy-phenyl)-hydrazinocarbonylmethyl]-benzoic acid hydrochloride;
  11) 5-bromo-2-methoxy-4-[N'-(4'-methoxy-biphenyl-4-yl)-N'-(2-piperidin-1-yl-phenyl)-hydrazinocarbonylmethyl]-benzoic acid hydrochloride;
  12) 5-bromo-4-[N'-(4-cyclohexyloxy-phenyl)-N'-(2-piperidin-1-yl-phenyl)-hydrazinocarbonylmethyl]-2-methoxy-benzoic acid hydrochloride;
  13) 5-bromo-2-methoxy-4-[N'-(4-phenoxy-phenyl)-N'-(2-piperidin-1-yl-phenyl)-hydrazinocarbonylmethyl]-benzoic acid hydrochloride;
  14) 5-bromo-4-{N'-[4-(4-chloro-phenoxy)-phenyl]-N'-(2-piperidin-1-yl-phenyl)-hydrazinocarbonylmethyl}-2-methoxy-benzoic acid hydrochloride;
  15) 4-{N'-[4-(4-fluoro-phenoxy)-phenyl]-N'-(2-methyl-6-piperidin-1-yl-phenyl)-hydrazinocarbonylmethyl}-2-methoxy-benzoic acid hydrochloride;
  16) 5-bromo-4-{N'-[4-(4-fluoro-phenoxy)-phenyl]-N'-(2-methyl-6-piperidin-1-yl-phenyl)-hydrazino-carbonyl-methyl}-2-methoxy-benzoic acid hydrochloride;
  16a) Methyl 5-bromo-4-{N'-[4-(4-fluoro-phenoxy)-phenyl]-N'-(2-methyl-6-piperidin-1-yl-phenyl)-hydrazinocarbonyl-methyl}-2-methoxy-benzoate;
  17) 4-[N'-(4-benzyl-phenyl)-N'-(2-piperidin-1-yl-phenyl)-hydrazinocarbonylmethyl]-5-bromo-2-methoxy-benzoic acid hydrochloride;
  18) 4-[N'-(4-bromo-phenyl)-N'-(2-piperidin-1-yl-phenyl)-hydrazinocarbonylmethyl]-5-chloro-2-methoxy-benzoic acid hydrochloride;
  19) 4-[N'-(3'-acetyl-biphenyl-4-yl)-N'-(2-piperidin-1-yl-phenyl)-hydrazinocarbonylmethyl]-5-chloro-2-methoxy-benzoic acid hydrochloride;
  20) 4-[N'-(4'-acetyl-biphenyl-4-yl)-N'-(2-piperidin-1-yl-phenyl)-hydrazinocarbonylmethyl]-5-chloro-2-methoxy-benzoic acid hydrochloride;
  21) 5-bromo-2-methoxy-4-[N'-(3-phenoxy)-phenyl]-N'-(2 piperidin-1-yl-phenyl)-hydrazinocarbonylmethyl]-benzoic acid hydrochloride;
  22) 5-bromo-2-methoxy-4-[N'-(4-phenylsulfanyl)-phenyl]-N'-(2-piperidin-1-yl-phenyl)-hydrazinocarbonylmethyl]-benzoic acid hydrochloride;
  23) 4-[N'-(4-benzenesulfonyl-phenyl)-N'-(2-piperidin-1-yl-phenyl)-hydrazinocarbonylmethyl]-5-bromo-2-methoxy-benzoic acid hydrochloride;
  24) 4-[N'-(4-benzenesulfinyl-phenyl)-N'-(2-piperidin-1-yl-phenyl)-hydrazinocarbonylmethyl]-5-bromo-2-methoxy-benzoic acid hydrochloride;
  25) 2-methoxy-4-{(E)-2-[N'-(4-methoxy-phenyl)-N'-(2-methyl-6-piperidin-1-yl-phenyl)-hydrazinocarbonyl]-vinyl}-benzoic acid hydrochloride;
  26) 5-bromo-2-methoxy-4-{(E)-2-[N'-(4-methoxy-phenyl)-N'-(2-methyl-6-piperidin-1-yl-phenyl)-hydrazinocarbonyl]-vinyl}-benzoic acid hydrochloride;
  27) 4[N"-(4-benzyl-phenyl)-N'-(2-methyl-6-piperidin 1-yl-phenyl)-hydrazinocarhonylmethyl]-5-bromo-2-methoxy-benzoic acid hydrochloride;
  28) 5-bromo-2-methoxy-4[N'-(4'-methoxy-biphenyl-4yl)-N'-(2-methyl-6-piperidin-1-yl-phenyl)-hydrazino-carbonyl-methyl]-benzoic acid hydrochloride;
  29) 4-[N'-(acetylamino-methyl)-phenyl]-N'-(2-methyl-6-piperidin-1-yl-phenyl)-hydrazinocarhonylmethyl]-5-bromo-2-methoxy-benzoic acid hydrochloride;
  30) 4-[N'-(4-benzoyl)-phenyl]-N'-(2-piperidin-yl-phenyl)-hydrazinocarbonylmethyl]-5-bromo-2-methoxy-benzoic acid hydrochloride;
  31) 5-bromo-4[N'-(4-cyano-phenyl)-N'-(2-methyl-6-piperidin-1-yl-phenyl)-hydrazinocarbonylmethyl]-2-methoxy-benzoic acid hydrochloride;
  32) 4-[N'-(4'-acetyl-biphenyl-4-yl)-N'-(2-methyl-6-piperidin-1-yl-phenyl)-hydrazinocarbonylmethyl]-5-bromo-2-methoxy-benzoic acid hydrochloride; and
  33) 5-bromo-2-methoxy-4-[N'-(4-methoxy-2-methyl-biphenyl-4-yl)-N'-(2-methyl-6-piperidin-1-yl-phenyl)-hydrazinocarbonylmethyl]-benzoic acid hydrochloride.

11. The method according to claim 10, wherein the compound treats a lesion associated with an infection by the papilloma virus.

12. The method according to claim 10, wherein the compound treats an ano-genital wart, a laryngeal, conjunctive or buccal papilloma or an epithelial lesion.

13. The method according to claim 12, wherein the ano-genital wart is an acuminated condyloma or a plane condyloma.

* * * * *